(12) United States Patent
Djamgoz et al.

(10) Patent No.: US 7,759,078 B2
(45) Date of Patent: Jul. 20, 2010

(54) DIAGNOSIS AND TREATMENT OF CANCER

(75) Inventors: Mustafa Bilgin Ali Djamgoz, London (GB); Scott Paton Fraser, London (GB); James Kenneth Joseph Diss, London (GB)

(73) Assignee: Imperial College Innovations Limited, London (GB)

( * ) Notice: Subject to any disclaimer, the term of this patent is extended or adjusted under 35 U.S.C. 154(b) by 0 days.

(21) Appl. No.: 11/980,978

(22) Filed: Oct. 31, 2007

(65) Prior Publication Data
US 2008/0145859 A1 Jun. 19, 2008

Related U.S. Application Data

(62) Division of application No. 10/362,747, filed on Sep. 22, 2003, now abandoned.

(51) Int. Cl.
G01N 33/574 (2006.01)
(52) U.S. Cl. .............................. 435/7.23; 435/7.1; 435/6
(58) Field of Classification Search ....................... None
See application file for complete search history.

(56) References Cited

U.S. PATENT DOCUMENTS 6,110,672 A 8/2000 Mandel et al.

OTHER PUBLICATIONS

Greenbaum et al., Genome Biology, 2003, vol. 4, Issue 9, pp. 117.1-117.8.*
Brennan et al., J. Autoimmunity, 1989, 2 (suppl.): 177-186.*
Zimmer, Cell Motility and the Cytoskeleton, 1991. 20:325-337.*
Hell et al., Laboratory Investigation, 1995, 73: 492-496.*
Fu et al., EMBO J., 1996, 15:43982-4401.*
Vallejo et al., Biochimie, 2000 82:1129-1133.*
Jang et al, Clinical Exp. Metastasis, 1997, 15: 469-483.*
Taber's Cyclopedic Medical Dictionary, 1985, F.A. Davis Company, Philadelphia, p. 274.*
Kaiser, Science, 2006, 313, 1370.*
Tockman et al, Cancer Res., 1992, 52:2711s-2718s.*
(PCT) International Preliminary Examination Report.
Laniado et al, American Journal of Pathology, "*Expression and Functional Analysis of Voltage-Activated Na+ Channels in Human Prostate Cancer Cell Lines and Their Contribution to Invastion in Vitro*" vol. 150, No. 4, (Apr. 1997), pp. 1213-1221.
Smith et al, Federation of European Biochemical Societies, "*Sodium Channel Protein Expression Enhances the Invasiveness of Rat and Human Prostate Cancer Cells*", vol. 423, (1998), pp. 19-24.
Diss et al, Federation of European Biochemical Societies, "*Expression of Skeletal Muscle-type Voltage-gated Na+ Channel in Rat and Human Prostate Cancer Cell Lines*", vol. 427 (1998), pp. 5-10.
Grimes et al, Federation of European Biochemical Societies, *Differential Expression of Voltage-activated Na+ Currents in two Prostatic Tumour Cell Lines: Contribution to Invasiveness in Vitro*, vol. 369, (1995), pp. 290-294.

Isaacs et al, The Prostate, "*Establishment and Characterization of Seven Dunning Rat Prostatic Cancer Cell Lines and Their Use in Developing Methods for Predicting Metastatic Abilities of Prostatic Cancers*", vol. 9, (1986) pp. 261-281.
Abdul and Hoosein, Anticancer Research, "*Inhibition by Anticonvulsants of Prostate-Specific Antigen and Interleukin-6 Secretion by Human Prostate Cancer Cells*", vol. 21, (2001), pp. 2045-2048.
Akopian et al., Federation of European Biochemical Societies, "*Structure and Distribution of a Broadly Expressed Atypical Sodium Channel*", vol. 400, (1997), pp. 183-187.
Anthony di Sant'Agnese, The Prostate Supplement, "*Neuroendoctrine Differentiation in Prostatic Carcinoma: An Update*", vol. 8, (1998), pp. 74-79.
Bartolomei et al, Journal of Neurocytology, "*Changes in the mRNAs Encoding Subtypes I, II, and III Sodium Channel Alpha Subunits Following Kainate-Induced Seizures in Rat Brain*", vol. 26, (1997), pp. 667-678.
Baumann et al, EMBO Journal, "*Molecular Organization of the Maternal Effect Region of the Shaker Complex of Drosophila: Characterization of an $I_A$ Channel Transcript with Homology to Vertebrate Na+ Channel*", vol. 6, No. 11, (1987), pp. 3419-3429.
Beckers et al, Genomics, *A New Sodium Channel a-Subunit Gene ((Scn9a) from Schwann Cells Maps to the Scn1a, Scn3a Cluster of Mouse Chromosome 2*, vol. 36, (1996), pp. 202-205.
Belcher et al, Proc. Natl. Acad. Sci., "*Cloning of a Sodium Channel a Subunit from Rabbit Schwann Cells*", vol. 92 (Nov. 1995), pp. 11034-11038.
Black et al, Molecular Brain Research, "*Sodium Channel mRNAs in Cultured Spinal Cord Astrocytes: in situ Hydridization in Identified Cell Types*", vol. 23, (1994), pp. 235-245.
Bonhaus et al, Neuropharmacolgy, "*The β1 Sodium Channel Subunit Modifies the Interactions of Neurotoxins and Local Anesthetics with the Rat Brain IIA a Sodium Channel in Isolated Membranes but Not In Intact Cells*", vol. 35, No. 5, (1996), pp. 605-613.

(Continued)

*Primary Examiner*—Misook Yu
*Assistant Examiner*—Mark Halvorson
(74) *Attorney, Agent, or Firm*—Nikolai & Mersereau, P.A.; C. G. Mersereau

(57) ABSTRACT

A method of diagnosing cancer in a human patient comprising the steps of (i) obtaining a sample containing nucleic acid and/or protein from the patient; and (ii) determining whether the sample contains a level of hNe—Na voltage-gated Na+ channel nucleic acid or protein associated with cancer.

Figure 1:
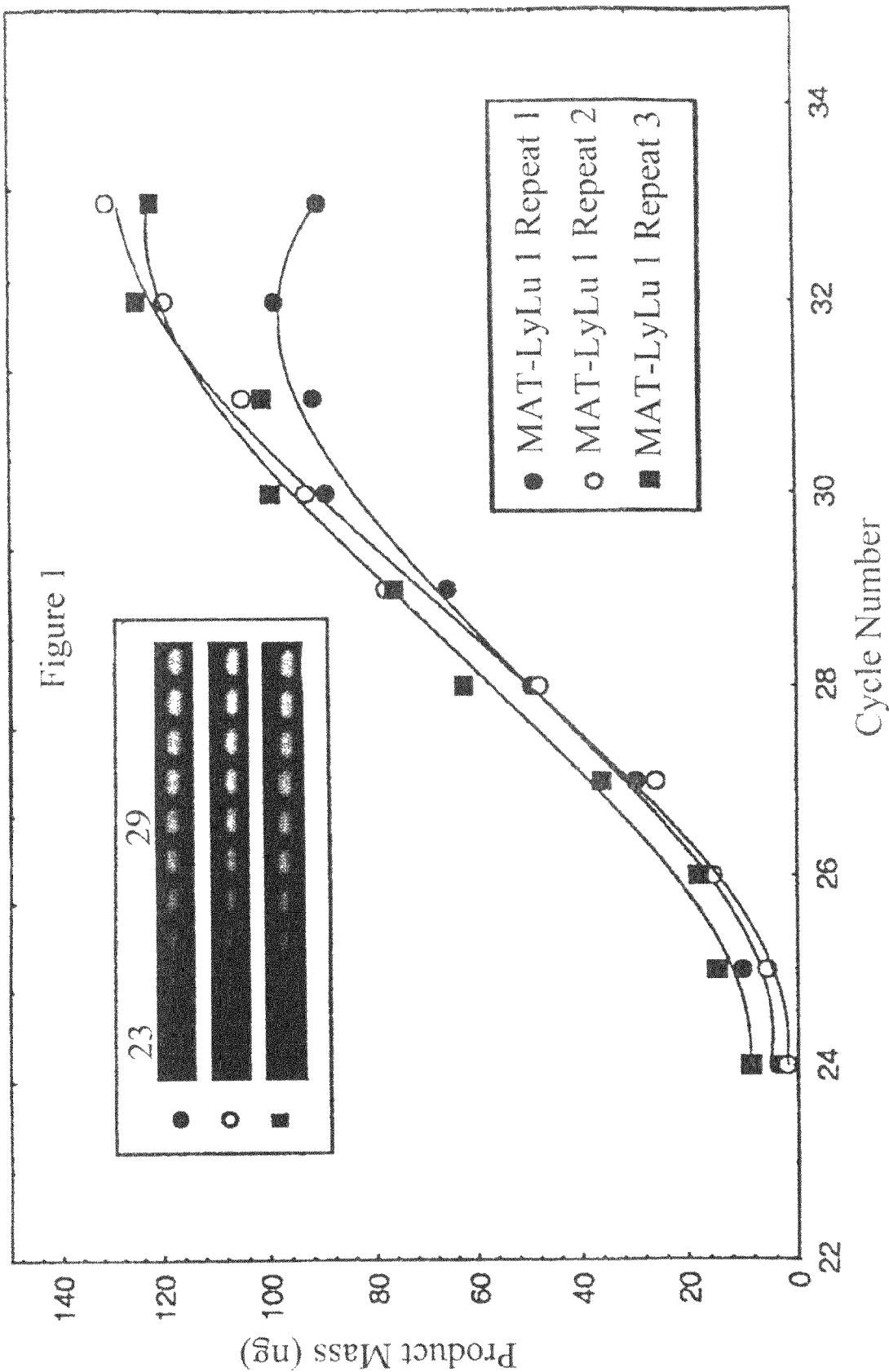

A method of treating cancer comprising the step of administering to the patient an agent which selectively prevents the function of hNe—Na voltage-gated Na+ channel.

A genetic construct comprising a nucleic acid encoding a molecule capable of preventing the function of hNe—Na voltage-gated Na+ channel expressed in a cell.

The methods and compositions are particularly suited to prostate cancer.

13 Claims, 10 Drawing Sheets

OTHER PUBLICATIONS

Bonkhoff et al, Virchows Archiv. A. Pathological Anatomy and Histopathology, "*Androgen Receptor Status in Endocrine-Paracrine Cell types of the Normal, Hyperplastic, and Neoplastic Human Prostate*", vol. 423, (1993), pp. 291-294.

Helmut Bonkhoff, The Postate Supplement, *Neuroendocrine Cells in Benign and Malignant Prostate Tissue: Morphogenesis, Proliferation, and Androgen Receptor Status*, vol. 8, (1998), pp. 18-22.

Dennis Bulman, Human Molecular Genetics, "*Phenotypoe Variation and Newcomers in Ion Channel Disorders*", vol. 6, No. 10, (1997), pp. 1679-1685.

Burgess et al, Nature Genetics, "*Mutation of a New Sodium Channel Gene, Scn8a, in the Mouse Mutant 'Motor Endplate Disease'*", vol. 10, (Aug. 1995), pp. 461-465.

Stephen Cannon, Molecular Neurology (JB Martin, Ed) Scientific American Inc, NY, "*Ion Channel Defects in the Hereditary Myotonias and Periodic Paralyses*", pp. 257-277.

Cannon et al, European Journal of Physiology, "*Modification of the $Na^{30}$ Current Conducted by the Rat Skeletal Muscle α Subunit by Coexpresssion with a Human Brain β subunit*", vol. 423, (1993), pp. 155-157.

Catalano and Shatz, Science, "*Activity-Dependent Cortical Target Selection by Thalamic Axons*", vol. 281, (Jul. 24, 1998), pp. 559-562.

William Catterall, Ann. Rev. Biochem., "*Molecular Properties of Voltage-Sensitive Sodium Channels*", vol. 55, (1986), pp. 953-985.

Chan and Sulmasy, American Journal of Medicine, "*What Should Men Know about Prostate-Specific Antigen Screening Before Giving Informed Consent?*", vol. 105, (1998), pp. 266-274.

Cummins et al, Journal of Neuroscience, *Slow Closed-State Inactivation: A Novel Mechanism Underlying Ramp Currents in Cells Expressing the hNE/PN1 Sodium Channel*, vol. 18, (1998), pp. 9607-9619.

Chomczynski and Sacchi, Analytical Biochemistry, "*Single-Step Method of RNA Isolation by Acid Guanidinium Thiocyanate-Phenol-Chloroform Extraction*", vol. 162, (1987), pp. 156-159.

Cohen et al, Cancer, "*Neuroendocrine Differentiation in Prostatic Adenocarcinoma and Its Relationship to Tumor Progression*", vol. 74, (1994), pp. 1899-1903.

Cooper et al, Journal of Membrane Biology, "*Electrophysiology of Cultured Human Lens Epithelial Cells*", vol. 117, (1990), pp. 285-298.

Dawes et al, Visual Neuroscience, "*Identification of Sodium Channel Subtypes Induced in Cultured Retinal Pigment Epithelium Cells*", vol. 12, (1995), pp. 1001-1005.

Dib-Hajj et al, Pro. Natl. Acad. Science USA, "*Down-Regulation of Transcripts for Na Channel a-SNS in Spinal Sensory Neurons Following Axotomy*", vol. 93, (Dec. 1996), pp. 14950-14954.

Dib-Hajj et al, Pro. Natl. Acad. Science USA, "*NaN, a Novel Voltage-gated Na Channel, is Expressed Preferentially in Peripheral Sensory Neurons and Down-Regulated After Axotomy*", vol. 95, (Jul. 1998), pp. 8963-8968.

Dib-Hajj et al, Federation of European Biochemical Societies, "*Sodium Channel mRNA in the B104 Neuroblastoma Cell Line*", vol. 284, (1996), pp. 78-82.

Dib-Hajj et al, Journal of Neurophysiology, "*Rescue of a-SNS Sodium Channel Expression in Small Dorsal Root Ganglion Neurons After Axotomy by Nerve Growth Factor in Vivo*", vol. 79, (1998), pp. 2668-2676.

Dib-Hajj et al, Genomics, "*Coding Sequence, Genomic Organization, and Conserved Chromosomal Localization of the Mouse Gene Scn11a Encoding the Sodium Channel NaN*", vol. 59, (1999), pp. 309-318.

Fjell et al, Molecular Brain Research, *Differential Role of GDNF and NGF in the Maintenance of Two TTX-Resistant Sodium Channels in Adult DRG Neurons*, vol. 67, (1999), pp. 267-282.

Foster et al, British Journal of Urology, "*The Cellular and Molecular Basis of Prostate Cancer*", vol. 83, (1999), pp. 171-194.

Fozzard and Hanck, Physiological Reviews, "*Structure and Function of Voltage-Dependant Sodium Channels: Comparison of Brain II and Cardiac Isoforms*", vol. 76, No. 3, (Jul. 1996), pp. 887-926.

Fraser et al, In: Electrophysiology, "*Electrophysiology of Xenopus Oocytes: and Expression System in Molecular Neurobiology*", (1993), pp. 65-86.

Fraser et al, Journal of Physiology, "*Voltage-gated $Na^+$ Channel Activity Contributes to Rodent Prostate Cancer Cell Migration in Vitro*", vol. 513.P, (1998), pp. 131P.

Fraser et al, Cell Tissue Res., "*Tetrodotoxin Suppresses Morphological Enhancement of the Metastatic MAT-LyLu Rat Prostate Cancer Cell Line*", vol. 295, (1999) pp. 505-512.

George et al, Genomics, "*Genomic Organization of the Human Skeletal Muscle Sodium Channel Gene*", vol. 15, (1993), pp. 598-606.

George et al, Genomics, "*Assignment of a Human Voltage-Dependent Sodium Channel a-Subunit Gene (SCN6A) to 2q21-q23*", vol. 19, (1994), pp. 395-397.

George et al, Proc. Natl. Aca. Sci. USA, "*Molecular Cloning of an atypical Voltage-grated Sodium Channel Expressed in Human Heart and Uterus: Evidence for a Distinct Gene Family*", vol. 89, (Jun. 1992), pp. 4893-4897.

Goldin et al, Proc. Natl. Aca. Sci. USA, "*Messinger RNA Coding for only the α Subunit of the Rat Brain Na Channel is Sufficient for Expression of Functional Channels in Xenopus Oocytes*", vol. 83, (Oct. 1986), pp. 7503-7507.

Greene and Tischler, Proc. Natl. Aca. Sci. USA, "*Establishment of a Noradrenergic Clonal Line of Rat Adrenal Pheochromocytoma Cells Which Respond to Nerve Growth Factor*", vol. 73, No. 7, (Jul. 1976), pp. 2424-2428.

Grimes and Djangoz, Journal of Cellular Physiology, "*Electrphysiological Characterization of Voltage-Gated $Na^+$ Current Expressed in the Highly Metastatic Mat-LyLu Cell Line of Rat Prostate Cancer*", vol. 175, (1998), pp. 50-58.

Gustafson et al, Journal of Biological Chemistry, "*Mutually Exclusive Exon Splicing of Type III Brain Sodium Channel a Subunit RNA Generates Developmentally Regulated Isoforms in Rat Brain*", vol. 268, No. 25, (Sep. 1993), pp. 18648-18653.

Isom et al, Science, "*Primary Structure and Functional Expression of the $β_1$ Subunit of the Rat Brain Sodium Channel*", vol. 256, (May 8, 1992), pp. 839-842.

Isom et al, Cell, "*Structure and Function of the β2 Subunit of Brain Sodium Channels, a Transmembrane Glycoprotein with a CAM Motif*", vol. 83, (Nov. 3, 1995), pp. 433-442.

Kallen et al, Neuron, "*Primary Structure and Expression of a Sodium Channel Characteristic of Denervated and Immature Rat Skeletal Muscle*", vol. 4, (Feb. 1990), pp. 233-242.

Kamb et al, Neuron, "*Multiple Products of the Drosophila Shaker Gene May Contribute to Potassium Channel Diversity*", vol. 1, (Jul. 1988), pp. 421-430.

Kanazirska et al, Biochemical and Biophysical Research Communications, "*Voltage-Dependent Effect of $Al^{3+}$ on Channel Activities in Hippocampal Neurons*", vol. 232, (1997), pp. 84-87.

Kayano et al, Federation of European Biochemical Societies, "*Primary Structure of Rat Brain Sodium Channel III Deduced From the cDNA Sequence*", vol. 228, No. 1, (Feb. 1988), pp. 187-194.

Klugbauer et al, EMBO Journal, "*Structure and Functional Expression of a New Member of the Tetrodotoxin-Sensitive Voltage-Activated Sodium Channel Family From Human Neuroendoctrine Cells*", vol. 14, No. 6, (1995), pp. 1084-1090.

Krijnen et al, Histochemistry, "*Do Neuroendocrine Cells in Human Prostate Cancer Express Androgen Receptor?*", vol. 100, (1993), pp. 393-398.

Lai et al, Methods in Enzymology, "*Blockade of Neuropathic Pain by Antisense Targeting of Tetrodotoxin-Resistant Sodium Channels in Sensory Neurons*", vol. 314, (1999), pp. 201-213.

Lee et al, Cancer and Metastasis Reviews, "*In Vivo and In Vitro Approaches to Study Metastasis in Human Prostatic Cancer*", vol. 12 (1993), pp. 21-28.

London et al, Proc. Natl. Acad. Sci. USA, "*Long QT and Ventricular Arrhythmias in Transgenic Mice Expressing the N Terminus and First Transmembrane Segment of a Voltage-gated Potassium Channel*", vol. 95, (Mar. 1998), pp. 2926-2931.

Loughey et al, Cell, "*Molecular Analysis of the para Locus, a Sodium Channel Gene in Dropsophila*", vol. 58, (Sep. 22, 1989), pp. 1143-1154.

Malo et al, Cytogen. Cell Genet., "*Localization of a Putative Human Brain Sodium Channel Gen (SCN1A) to Chromosome Band 2q24*", vol. 67, (1994), pp. 178-186.

Malo et al, Proc. Natl. Acad. Sci. USA, "*Targeted Gene Walking by Low Stringency Polymerase Chain Reaction: Assignment of a Putative Human Brain Sodium Channel Gene (SCN3A) to Chromosome 2q24-31*", vol. 91, (Apr. 1994), pp. 2975-2979.

Mandelson et al, Ann. Rev. Public Health, "*PSA Screening: A Public Health Dilemma*", vol. 16, (1995), pp. 283-306.

Marban et al, Journal of Physiology, "*Structure and Function of Voltage-gated Sodium Channels*", vol. 508.3, (1998), pp. 647-657.

Noda et al, Nature, "*Expression of Functional Sodium Channels From Cloned cDNA*", vol. 322, (Aug. 28, 1986), pp. 826-828.

Oh and Waxman, Neuroreport, "*Novel Splice Variants of the Voltage-Sensitive Sodium Channel Alpha Subunit*", vol. 9, (1998), pp. 1267-1272.

Okamura et al, Neuron, "*Neural Expression of a Sodium Channel Gene Requires Cell-Specific Interactions*", vol. 13, (Oct. 1994), pp. 937-948.

Penn et al, Science, "*Competition in retinogeniculate Patterning Driven by Spontaneous Activity*", vol. 279, (Mar. 27, 1998), pp. 2108-2112.

Plummer and Meisler, Genomics, "*Evolution and Diversity of Mammalian Sodium Channel Genes*", vol. 57, (1999), pp. 323-331.

Plummer et al, Genomics, "*Exon Organization, Coding Sequence, Physical Mapping and Polymorphic Intragenic Markers for the Human Neuronal Sodium Channel Gene SCN8A*", vol. 54, (1998), pp. 287-296.

Pongs et al, EMBO Journal, "*Shaker Encodes a Family of Putative Potassium Channel Proteins in the Nervous System of Drosophila*", vol. 7, No. 4, (1988), pp. 1087-1096.

Rich et al, Neurobiology of Disease, "*Altered Gene Expression in Steroid-Treated Denervated Muscle*", vol. 6, (1999), pp. 515-522.

Roy et al, Glia, "*Manipulation of the Delayed Rectifier Kv1.5 Potassium Channel in Glial Cells by Antisense Oligodeoxynucleotides*", vol. 18 (1996) pp. 177-184.

Safo et al, Society for Neuroscience Abstract, "*Conotoxins Distinguish Among Voltage-Dependent Sodium Channel Types*", vol. 24, (1998) p. 1324.

Sangameswaran et al, Journal of Biological Chemistry, "*A Novel Tetrodotoxin-Sensitive, Voltage-gated Sodium Channel Expressed in Rat and Human Dorsal Root Ganglia*", vol. 272, No. 23, (Jun. 6, 1997), pp. 14805-14809.

Sarao et al, Nucleic Acids Research, "*Developmentally Regulated Alternative RNA Splicing of Rat Brain Sodium Channel mRNAs*" vol. 19 No. 20 (1991) pp. 5673-5679.

Schlief et al, Eur. Biophys., "*Pore Properties of Rat Brain II Sodium Channels Mutated in the Selectivity Filter Domain*", vol. 25 (1996), pp. 75-91.

Carla Shatz, Neuron, "*Impulse Activity and the Patterning of Connections During CNS Development*", vol. 5, (1990), pp. 745-756.

Shevrin et al, Prostate, "*Patterns of Metastasis by the Human Prostate Cancer Cell Line PC-3 in Athymic Nude Mice*", vol. 15 (1989) pp. 187-194.

Skaper et al, FASEB J. "*Melatonin Prevents the Delayed Death of Hippocampal Neurons Induced by Enhanced Excitatory Neurotransmission and the Nitridergic Pathway*", vol. 12 (1998) pp. 725-731.

Sontheimer et al, Journal of Neuroscience, "*Astrocyte $Na^+$ Channels Are Required for Maintenance of $Na^+$-ATPase Activity*", vol. 14 (5), (May 1994), pp. 2464-2475.

Souslova et al, Genomics, "*Cloning and Characterization of a Mouse Sensory Neuron Tetrodotoxin-Resistant Voltage-Gated Sodium Channel Gene, Scn10a*", vol. 41, (1997), pp. 201-209.

Stephenson et al, J Nat'l Cancer Inst, "*Metastatic Model for Human Prostate Cancer Using Orthotopic Implantation in Nude Mice*", vol. 84, No. 12, (Jun. 17, 1992), pp. 951-957.

Tabb et al, Journal of Neuroscience, "*Suppression of Sodium Channel Function in Differentiating C2 Muscle Cells Stably Overexpressing Rat Androgen Receptors*", vol. 14, (Feb. 1994), pp. 763-773.

Tanaka et al, Neuroreport, "*SNS $Na^+$ Channel Expression Increases in Dorsal Root Ganglion Neurons in the Carrageenan Inflammatory Pain Model*", vol. 9, (1998), pp. 967-972.

Toledo-Aral et al, Proc. Nat'l Adad. Sci. USA, "*Identification of PN1, a Predominant Voltage-Dependent Sodium Channel Expressed Principally in Peripheral Neurons*", vol. 94, (Feb. 1997), pp. 1527-1532.

Tu et al, Biophysical Journal, "*Truncated $K^+$ Channel DNA Sequences Specifically Suppress Lymphocyte $K^+$ Channel Gene Expression*"38 , vol. 68, (Jan. 1995), pp. 147-156.

Wang et al, Genomics, "*Genomic Organization of the Human SCN5A Gene Encoding the Cardiac Sodium Channel*", vol. 34, (1996), pp. 9-16.

Wang et al, Biophysical Journal, "*Comparison of Heterologously Expressed Human Cardiac and Skeletal Muscle Sodium Channels*", vol. 70 (1996) pp. 238-245.

Waters et al, Prostate, "*Spontaneous Metastasis of PC-3 Cells in Athymic Mice After Implantation in Orthotopic or Ectopic Microenvironments*", vol. 26, (1995), pp. 227-234.

Watsky et al, Pfuger Arch., "*Sodium Channels in Ocular Epithelia*", vol. 419, (1991), pp. 454-459.

Zhou and Hoffman, Journal of Biological Chemistry, "*Pathophysiology of Sodium Channelopathies*", vol. 269, No. 28, (Jul. 15, 1994), pp. 18563-18571.

Kohrman et al, Journal of Neuroscience, "*A Missense Mutation in the Sodium Channel Scn8a Is Responsible for Cerebellar Ataxia in the Mouse Mutant Jolting*", vol. 16, (1996), pp. 5993-5999.

Raman et al, Neuron, "*Altered Subthreshold Sodium Currents and Disrupted Firing Patterns in Purkinje Neurons of Scn8a Mutant Mice*", vol. 19, (1997), pp. 881-891.

Yamamoto et al, Journal of Neurochemistry, "*Up-Regulation of Functional Voltage-Dependent Sodium Channels by Insulin in Cultured Bovine Adrenal Chromaffin Cells*", vol. 67, (1996), pp. 1401-1408.

Grimes and Djamgoz, Journal of Physiology, "*Voltage-gated $K^+$ Current in the Highly Metastic MAT-LyLu Rat Prostate Cancer Cell Line: Electrophysiological and Pharmacological Characteristics*", vol. 495, (1996), p. 76P.

Grimes and Djamgoz, Journal of Physiology, "*Electrophysiological Characterization of a TTX-Sensitive $Na^+$ Current in the Highly Metastic MAT-LyLu Rat Prostate Cancer Cell Line*", vol. 489, (1995), p. 50P.

Stewart et al, Society for Neuroscience, "*Expression of Voltage-Gated $Na^+$ Channels in Human Prostate Cancer*", vol. 25, (1999), p. 208.

Barton et al, Urology, "*Growth Factors and Their Receptors: New Targets for Prostate Cancer Therapy*", vol. 58, (2001), pp. 114-122.

Mendelsohn and Baselga, Oncogene, "*The EGF Receptor Family as Targets for Cancer Therapy*", vol. 19, (2000), pp. 6550-6565.

Diss et al, Prostate, "*Expression Profiles of Voltage-Gated $Na^+$ Channel a-Subunit Genes in Rat and Human Prostate Cancer Cell Lines*", vol. 48, (2001), pp. 165-178.

Toledo-Aral et al, Neuron, "*A Single Pulse of Nerve Growth Factor Triggers Long-Term Neuronal Excitability Through Sodium Channel Gene Induction*", vol. 14, (Mar. 1995), pp. 607-611.

Black et al, Developmental Neuroscience, "*Sodium Channel Expression: A Dynamic Process in Neurons and Non-Neuronal Cells*", vol. 18, (1996), pp. 139-152.

Pinar Uysal-Onganer et al., Molecular Cancer, "*Epidermal Growth Factor Potentiates in vitro Metastatic Behavior of Human Prostate Cancer PC-3M Cells: Involvement of Voltage-gated Sodium Channel*"vol. 6 (Nov. 24, 2007) 76.

Nakajima et al, British Journal of Pharmacology, "*Eicosapentaenoic Acid Inhibits Voltage-gated Sodium Channels and Invasiveness in Prostate Cancer Cells*", vol. 156, (2009), pp. 420-431.

Diss et al, Prostate Cancer and Prostatic Diseases, "*A Potential NOvel Marker for Human Prostate Cancer: Voltage-gated Sodium Channel Expression in vivo*", vol. 8(3) (2005) pp. 266-273.

\* cited by examiner

Figure 2:
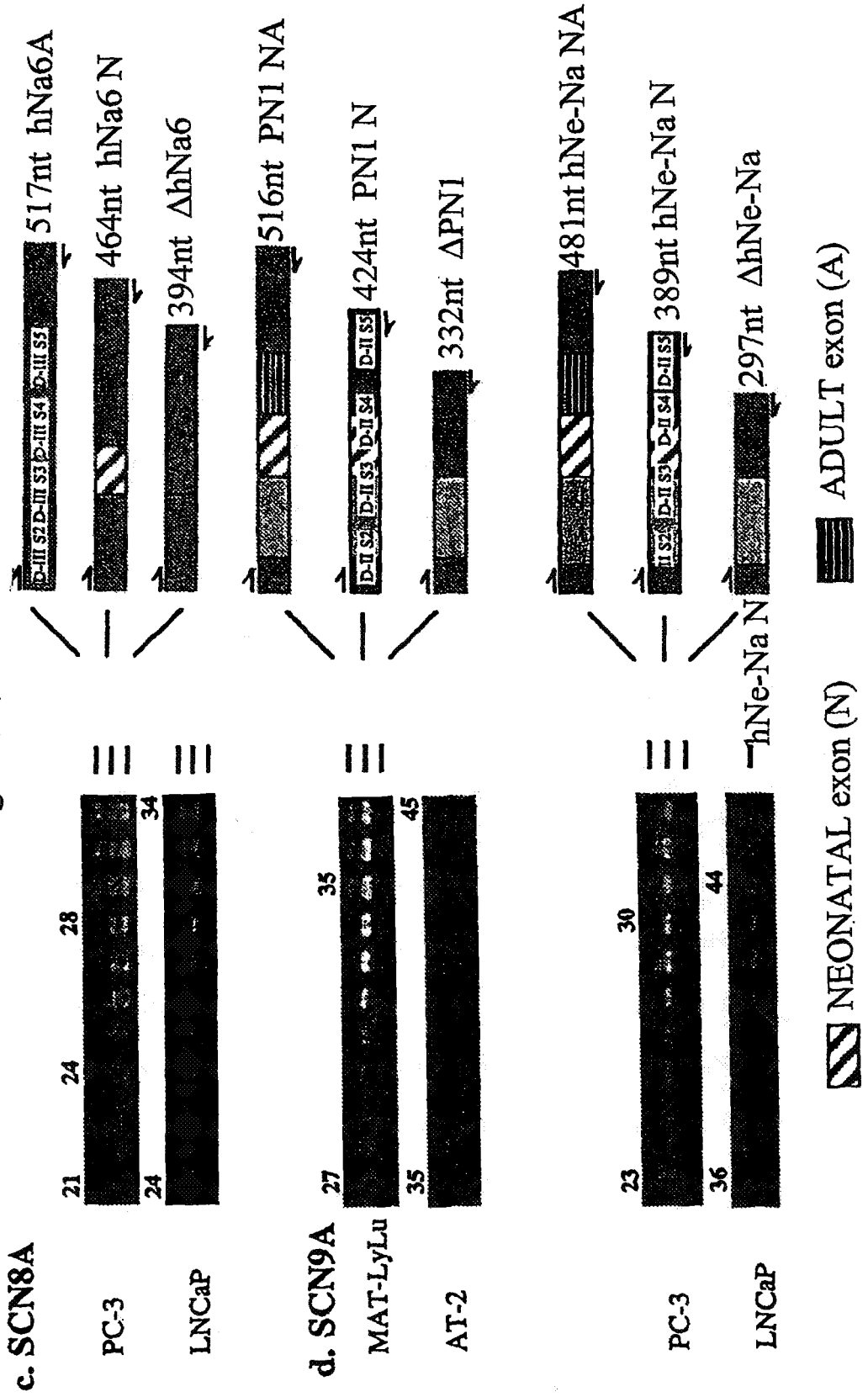

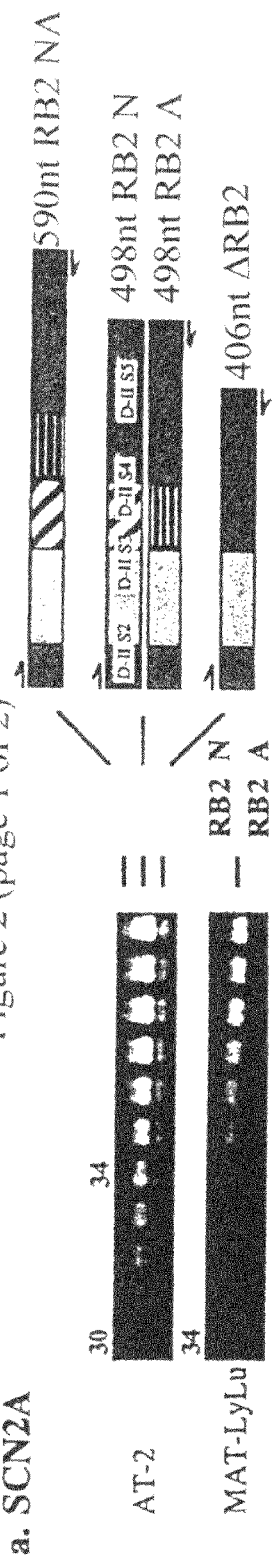 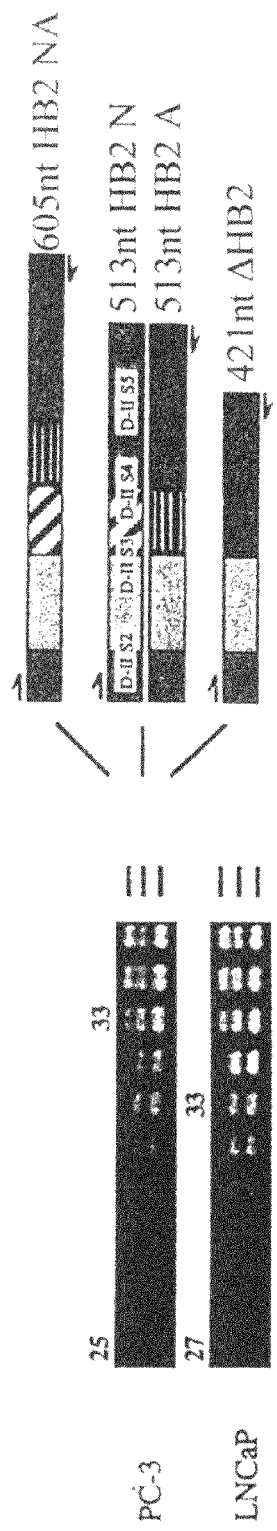
Figure 2 (page 1 of 2)

(A)

'Wild Type' VGSC α Transmembrane Domain 3

Mis-splicing at (a): removal of exon.

Alternative splicing at (a): Swapping of adult and neonatal exons

Δ hNa6 hNa6N (B)

'Wild Type' VGSC α Transmembrane Domain 1

Mis-splicing at (a): removal of exon.

ΔhNe-Na and Δ HB 2

A

B

DIAGNOSIS AND TREATMENT OF CANCER

This application is a divisional of application Ser. No. 10/362,747, filed Sep. 22, 2003 now abandoned, and entitled "DIAGNOSIS AND TREATMENT OF CANCER".

The present invention relates to methods of determining whether a patient has cancer and whether the cancer is likely to metastasise; and it relates to methods of treating cancer, particularly prostate cancer.

Cancer is a serious disease and a major killer. Although there have been advances in the diagnosis and treatment of certain cancers in recent years, there is still a need for improvements in diagnosis and treatment. Cancer is a genetic disease and in most cases involves mutations in one or more genes. There are believed to be around 60,000 genes in the human genome but only a handful of these genes have been shown to be involved in cancer. Although it is surmised that many more genes than have been presently identified will be found to be involved in cancer, progress in this area has remained slow despite the availability of molecular analytical techniques. This may be due to the varied structure and function of genes which have been identified to date which suggests that cancer genes can take many forms and have many different functions.

Carcinoma of the prostate has become a most significant disease in many countries and it is the most commonly diagnosed malignancy in men in the western world, its occurrence increasing significantly with age. Over the last 20 years the mortality rates have doubled and it is now the second commonest cause of male cancer deaths in the Western world (Wingo et al (1995) *Cancer J. Clin.* 45, 8-30; Mortality Statistics: Cause England and Wales. OPCS DH2 19, 1993, Her Majesty's Stationery Office). The prevalence of prostate cancer has increased by 28% in the last decade and this disease now accounts for 12% of the total cancers of men in England and Wales (Cancer Statistics: Registrations England and Wales. OPCS MBI No 22, 1994, Her Majesty's Stationery Office; Foster et al (1999) *Br. J. Urol.* 83, 171-194). By the year 2018 it is expected to be the biggest killer with 50% of the male population suffering from it (80% by age 80 years). Recent evidence suggests that prostate cancer is also increasing amongst younger men as well (*Br J Cancer* (1999) 79, 13-17). These increases and the recent deaths of many public figures from prostatic cancer have served to highlight the need to do something about this cancer. It has been suggested that the wider availability of screening may limit mortality from prostate cancer.

Prostate cancer screening currently consists of a rectal examination and measurement of prostate specific antigen (PSA) levels. These methods lack specificity as digital rectal examination has considerable inter-examiner variability (Smith & Catalona (1995) *Urology* 45, 70-74). Measurement of serum prostate specific antigen (PSA), synthesised by the epithelial cells of the prostatic acini and ducts and secreted as a normal constituent of seminal fluid, is currently the most commonly applied diagnostic marker of the cancer (e.g. Gao et al (1997) *The Prostate* 31, 264-281). However, PSA measurements can give inconsistent information so that some patients with prostate cancer have low levels of PSA, while PSA levels may be elevated in the presence of non-malignant prostatic disease, for example benign prostatic hyperplasia (BPH), prostatic inflammation and other conditions (e.g. Mandelson et al (1995) *Annu. Rev. Public Health* 16, 283-306; Flood et al (1996) *J. Gen. Int. Med.* 11, 342-349; Morgan et al (1996) *The Prostate* 57, 58-63; Chan & Sulmasy (1998) *Am. J. Med.* 108, 226-274. The comparative failure of PSA as a diagnostic test was shown in 366 men who developed prostate cancer while being included in the Physicians Health Study, a prospective study of over 22,000 men. PSA levels were measured in serum, which was stored at the start of the study, and elevated levels were found in only 47% of men developing prostate cancer within the subsequent four years (Gann et al (1995) *JAMA* 273, 289-294).

Present screening methods are therefore unsatisfactory; there is no reliable method for diagnosing the cancer, or predicting or preventing its possible metastatic spread, which is the main cause of death for most patients.

Grimes et al (1995) *FEBS Lett.* 369, 290-294 describes the differential expression of voltage-activated $Na^+$ currents in two prostatic tumour cell lines and discusses their contribution to invasiveness in vitro. The cell lines studied were rat cell lines and there is no indication of which particular $Na^+$ channels may be involved.

Laniado et al (1997) *Am. J. Pathol.* 150, 1213-1221 describes the expression and functional analysis of voltage-activated $Na^+$ channels in human prostate cancer cell lines and discusses their contribution to invasion in vitro. There is no indication of which particular $Na^+$ channels may be involved.

Smith et al (1998) *FEBS Lett.* 423, 19-24 suggests that $Na^+$ channel protein expression enhances the invasiveness of rat and human prostate cancer cell lines.

Grimes & Djamgoz (1998) *J. Cell. Physiol.* 175, 50-58 describes the electrophysiological and pharmacological characterisation of voltage-gated $Na^+$ current expressed in the highly metastatic Mat-LyLu cell line of rat prostate cancer.

Dawes et al (1995) *Visual Neuroscience* 12, 1001-1005 describes the identification of $Na^+$ channel subtypes induced in cultured retinal pigment epithelium cells.

Reviews of $Na^+$ channels may be found in, for example, Black & Waxman (1996) *Develop. Neurosci.* 18, 139-152; Fozzard & Hanck (1996) *Physiol. Rev.* 76, 887-926; Bullman (1997) *Hum. Mol. Genet.* 6, 1679-1685; Cannon (1999); and Marban et al (1998) *J. Physiol.* 508, 647-657. Some $Na^+$ and other ion channels are well known to underly certain genetic defects as is described in Bullman (1997) *Hum. Mol. Genet.* 6, 1679-1685; Burgess et al (1995) *Nature Genet.* 10, 461-465; and Cannon (1998) *Mol Neurology* (JB Martin, Ed) Scientific American Inc., NY. However, no $Na^+$ channel sequence is used presently for diagnostic purposes.

Thus, although previous work may have suggested some general role for voltage-gated $Na^+$ channels (VGSCs) in prostate cancer and its metastasis based on work in cell lines, until now it has not been possible to make use of this information effectively since the involvement of VGSCs in prostate cancer in vivo has not been demonstrated, and the particular VGSC(s) involved in human prostate cancer have not been identified.

We have now found, surprisingly, that VGSC expression correlates with pathological progression and that the VGSC which is associated with human cancer, particularly prostate cancer and its metastases, is hNe—Na (also termed $Na_v1.7$). As noted above, this is a known VGSC (although not previously known to be associated with human cancer or cancer cell lines, in particular human prostate cancer) and an amino acid sequence of the protein, and cDNA of the mRNA encoding it has been reported (Klugbauer et al (1995) *EMBO J.* 14, 1084-1090). hNe—Na (human) and PN1(rat) correspond to the SCN9A gene, as discussed in Example 1. Recently, a new VGSC nomenclature has been adopted (Goldin et al (2000) *Neuron* 28(2), 365-368). In this system hNe—Na and PN1 are the human and rat orthologs, respectively, of $Na_v1.7$.

The chromosomal location of hNe—Na has not yet been determined. However, the mouse equivalent has been located to the voltage-gated Na⁺ channel cluster on mouse chromosome 2 (Beckers et al (1997) *Genomics* 36, 202-205). This cluster is also present in human chromosome 2 where hNe—Na may similarly be present (Malo et al (1994) *Cytogen. Cell. Genet.* 67, 178-186; Malo et al (1994) *Proc. Natl. Acad. Sci. USA* 91, 2975-2979; George et al (1994) *Genomics* 19, 395-397). The hNe—Na gene (human SCN9A) intron/exon organisation has not yet been determined but could be inferred from other known, conserved VGSC intron positions (Loughey et al (1989) *Cell* 58, 1143-1154; George et al (1993) *Genomics* 15, 598-606; Wang et al (1996) *Genomics* 34, 9-16; and Sonslova et al (1997) *Genomics* 41, 201-209).

The brain-type Na⁺ channels (rat brain 1-111 (Noda et al (1986) *Nature* 322, 826-828; Kayano et al (1988) *FEBS Lett.* 228, 187-194) that are most similar to hNe—Na are 20% different over the whole sequence (human skeletal, 30%; heart 34% different). However, (i) if sequence comparison is made within specific structural/functional domains this homology is much reduced (eg first one-third of DII-DIII cytoplasmic linker region is only 45% homologous to the most similar channel (RBII/HBII); (ii) hNe—Na has sufficiently different regions (eg residues 446-460: EYT-SIRRSRIMGLSE) to make specific antibodies (see, for example, Toledo-Aral et al (1997) *Proc. Natl. Acad. Sci. USA* 94, 1527-1532).

It is an object of the invention to provide methods useful in providing diagnoses and prognoses of cancer, especially prostate cancer, and for aiding the clinician in the management of cancer, particularly prostate cancer. In particular, an object of the invention is to provide a method of assessing the metastatic potential of cancer, in particular prostate cancer.

Further objects of the invention include the provision of methods of treatment of cancer, in particular prostate cancer, and methods of identifying compounds which selectively inhibit the VGSC associated with human cancer, particularly prostate cancer, since these may be useful in treating cancer.

A first aspect of the invention provides a method of determining the susceptibility of a human patient to cancer comprising the steps of (i) obtaining a sample containing nucleic acid and/or protein from the patient; and (ii) determining whether the sample contains a level of hNe—Na voltage-gated Na⁺ channel nucleic acid or protein associated with cancer.

A second aspect of the invention provides a method of diagnosing cancer in a human patient comprising the steps of (i) obtaining a sample containing nucleic acid and/or protein from the patient; and (ii) determining whether the sample contains a level of hNe—Na voltage-gated Na⁺ channel nucleic acid or protein associated with cancer.

It will be appreciated that determining whether the sample contains a level of hNe—Na VGSC nucleic acid or protein associated with cancer may in itself be diagnostic of cancer or it may be used by the clinician as an aid in reaching a diagnosis.

For example, in relation to prostate cancer, it is useful if the clinician undertakes a histopathological examination of biopsy tissue or measures plasma PSA level or carries out external digital examination or carries out imaging. Recently, the possibility of using the blood IGF-1 level has also been suggested (Chan et al (1998) *Science* 279, 563-566). It will be appreciated that the clinician will wish to take in to account these or other factors, as well as consider the level of said VGSC, before making a diagnosis.

A third aspect of the invention provides a method of predicting the relative prospects of a particular outcome of a cancer in a human patient comprising the steps of (i) obtaining a sample containing nucleic acid and/or protein from the patient; and (ii) determining whether the sample contains a level of hNe—Na voltage-gated Na⁺ channel nucleic acid or protein associated with cancer.

Thus, the method of the third aspect of the invention may be useful in prognosis or aiding prognosis. The method may be used as an adjunct to known prognostic methods such as histopathological examination of biopsy tissue, or measurement of plasma PSA levels, external digital examination or imaging.

It will be appreciated that determination of the level of the said VGSC in the sample will be useful to the clinician in determining how to manage the cancer in the patient. For example, since elevated levels of the said VGSC are associated with metastatic potential, particularly in a prostate cancer, and may be associated with androgen-insensitivity, the clinician may use the information concerning the levels of the said VGSC to facilitate decision making regarding treatment of the patient. Thus, if the level of said VGSC is indicative of a low metastatic potential of said prostate cancer, unnecessary radical surgery may be avoided. Similarly, if the level of said VGSC is indicative of a high metastatic potential of said prostate cancer, radical surgery (ie prostatectomy) may be the preferred treatment.

It will be appreciated from the foregoing, and from the Examples below, that the determination of the levels of the said VGSC may be exploited diagnostically to predict whether a given cancer, particularly cancer of the prostate, would metastasise since expression of said VGSC is believed to correspond to possible future spread of a tumour.

It is particularly preferred if the cancer under consideration is prostate cancer.

It is also particularly preferred if the method of the invention is employed to predict whether a given cancer of the prostate would metastasise.

The level of said VGSC which is indicative of cancer or metastatic potential may be defined as the increased level present in known cancerous or metastatic prostate cells over known non-cancerous or non-metastatic prostate cells. The level of said VGSC protein may be, for example, at least 1½ fold higher in cancerous cells or metastatic cells, or it may be at least 2-fold or 3-fold higher. Quantitative analysis by micro-densitometry of immunohistochemically processed tissue sections has shown that VGSC expression in cancerous regions of prostatic ducts is three times higher than the corresponding benign region (see Example 3). The antibody used is believed to react with all VGSCs, but our findings in Example 1 indicate that the hNe—Na Na⁺ channel is likely to be the predominant form in human prostate cancer cells, and it is therefore likely that it is mainly the hNe—Na Na⁺ channel which is being recognised. The level of mRNA encoding said VGSC may be, for example, at least 1½ fold higher in cancerous cells or metastatic cells, or it may be at least 2-fold or 3-fold higher, or at least 10, 50, 100, 500 or 1000-fold higher. Measurements by semi-quantitative PCR indicates that the level of mRNA is about 1000-fold higher in the highly metastatic cell lines than in the lowly-metastatic cell lines, as described in the Examples.

In one preferred embodiment of the invention it is determined whether the level of said VGSC nucleic acid, in particular mRNA, is a level associated with cancer. Preferably, the sample contains nucleic acid, such as mRNA, and the level of said VGSC is measured by contacting said nucleic acid with a nucleic acid which hybridises selectively to said VGSC nucleic acid.

By "selectively hybridising" is meant that the nucleic acid has sufficient nucleotide sequence similarity with the said human nucleic acid that it can hybridise under moderately or highly stringent conditions. As is well known in the art, the stringency of nucleic acid hybridization depends on factors such as length of nucleic acid over which hybridisation occurs, degree of identity of the hybridizing sequences and on factors such as temperature, ionic strength and CG or AT content of the sequence. Thus, any nucleic acid which is capable of selectively hybridising as said is useful in the practice of the invention.

Nucleic acids which can selectively hybridise to the said human nucleic acid include nucleic acids which have >95% sequence identity, preferably those with >98%, more preferably those with >99% sequence identity, over at least a portion of the nucleic acid with the said human nucleic acid. As is well known, human genes usually contain introns such that, for example, a mRNA or cDNA derived from a gene would not match perfectly along its entire length with the said human genomic DNA but would nevertheless be a nucleic acid capable of selectively hybridising to the said human DNA. Thus, the invention specifically includes nucleic acids which selectively hybridise to said VGSC mRNA or cDNA but may not hybridise to a said VGSC gene. For example, nucleic acids which span the intron-exon boundaries of the said VGSC gene may not be able to selectively hybridise to the said VGSC mRNA or cDNA.

Typical moderately or highly stringent hybridisation conditions which lead to selective hybridisation are known in the art, for example those described in *Molecular Cloning, a laboratory manual,* 2nd edition, Sambrook et al (eds), Cold Spring Harbor Laboratory Press, Cold Spring Harbor, N.Y., USA, incorporated herein by reference.

An example of a typical hybridisation solution when a nucleic acid is immobilised on a nylon membrane and the probe nucleic acid is ⅂500 bases or base pairs is:
6×SSC (saline Na⁺ citrate)
0.5% Na⁺ dodecyl sulphate (SDS)
100:g/ml denatured, fragmented salmon sperm DNA The hybridisation is performed at 68EC. The nylon membrane, with the nucleic acid immobilised, may be washed at 68° C. in 1×SSC or, for high stringency, 0.1×SSC.

20×SSC may be prepared in the following way. Dissolve 175.3 g of NaCl and 88.2 g of Na⁺ citrate in 800 ml of H$_2$O. Adjust the pH to 7.0 with a few drops of a 10 N solution of NaOH. Adjust the volume to 1 litre with H$_2$O. Dispense into aliquots. Sterilize by autoclaving.

An example of a typical hybridisation solution when a nucleic acid is immobilised on a nylon membrane and the probe is an oligonucleotide of between 15 and 50 bases is:
3.0 M trimethylammonium chloride (TMACl)
0.01 M Na⁺ phosphate (pH 6.8)
1 mm EDTA (pH 7.6)
0.5% SDS
100 μg/ml denatured, fragmented salmon sperm DNA
0.1% nonfat dried milk The optimal temperature for hybridization is usually chosen to be 5EC below the T$_i$ for the given chain length. T$_i$ is the irreversible melting temperature of the hybrid formed between the probe and its target sequence. Jacobs et al (1988) *Nucl. Acids Res.* 16, 4637 discusses the determination of T$_i$s. The recommended hybridization temperature for 17-mers in 3 M TMACl is 48-50EC; for 19-mers, it is 55-57EC; and for 20-mers, it is 58-66EC.

By "nucleic acid which selectively hybridises" is also included nucleic acids which will amplify DNA from the said VGSC mRNA by any of the well known amplification systems such as those described in more detail below, in particular the polymerase chain reaction (PCR). Suitable conditions for PCR amplification include amplification in a suitable 1× amplification buffer:

10× amplification buffer is 500 mM KCl; 100 mM Tris.Cl (pH 8.3 at room temperature); 15 mM MgCl$_2$; 0.1% gelatin.

A suitable denaturing agent or procedure (such as heating to 95° C.) is used in order to separate the strands of double-stranded DNA. Suitably, the annealing part of the amplification is between 37° C. and 60° C., preferably 50° C.

Although the nucleic acid which is useful in the methods of the invention may be RNA or DNA, DNA is preferred. Although the nucleic acid which is useful in the methods of the invention may be double-stranded or single-stranded, single-stranded nucleic acid is preferred under some circumstances such as in nucleic acid amplification reactions.

The nucleic acid which is useful in the methods of the invention may be any suitable size. However, for certain diagnostic, probing or amplifying purposes, it is preferred if the nucleic acid has fewer than 10 000, more preferably fewer than 1000, more preferably still from 10 to 100, and in further preference from 15 to 30 base pairs (if the nucleic acid is double-stranded) or bases (if the nucleic acid is single stranded). As is described more fully below, single-stranded DNA primers, suitable for use in a polymerase chain reaction, are particularly preferred.

The nucleic acid for use in the methods of the invention is a nucleic acid capable of hybridising to the said VGSC mRNAs. Fragments of the said VGSC genes and cDNAs derivable from the mRNA encoded by the said VGSC genes are also preferred nucleic acids for use in the methods of the invention.

It is particularly preferred if the nucleic acid for use in the methods of the invention is an oligonucleotide primer which can be used to amplify a portion of the said VGSC nucleic acid, particularly VGSC mRNA.

The hNe—Na mRNA is similar to, but distinct from other VGSC mRNAs. Nucleic acids for use in the invention may hybridise to more than one, for example all, substantially all or a particular subset of VGSC mRNAs. This is discussed further in Examples 1 and 2. Thus the nucleic acid for use in the invention may hybridise to a part of VGSC mRNAs that encodes a region of the VGSC polypeptide that is conserved between VGSCs, for example has the same amino acid sequence in all, substantially all or a particular subset of VGSCs. Preferred nucleic acids for use in the invention are those that selectively hybridise to the hNe—Na mRNA and do not hybridise to other VGSC mRNAs. Such selectively hybridising nucleic acids can be readily obtained, for example, by reference to whether or not they hybridise to the said VGSC mRNA and not to other VGSC mRNAs.

Methods and nucleic acids as described, for example, in Example 1, may be used. In particular, a semi-quantitative PCR technique, for example as described in Example 1, may be used.

The methods are suitable in respect of any cancer but it is preferred if the cancer is cancer of the prostate.

It is preferred if the nucleic acid is derived from a sample of the tissue in which cancer is suspected or in which cancer may be or has been found. For example, if the tissue in which cancer is suspected or in which cancer may be or has been found is prostate, it is preferred if the sample containing nucleic acid is derived from the prostate of the patient. Samples of prostate may be obtained by surgical excision, laproscopy and biopsy, endoscopy and biopsy, and image-guided biopsy. The image may be generated by ultrasound or technetium-99-labelled antibodies or antibody fragments which bind or locate selectively at the prostate.

Although any sample containing nucleic acid derived from the patient is useful in the methods of the invention, it is preferred if the sample is selected from the group consisting of prostate tissue, blood, urine or semen. Prostate tissue can be obtained from a patient using standard surgical techniques. Cells derived from the prostate are found in small numbers in the urine and in the blood. Although it is preferred that the sample containing nucleic acid from the patient is, or is derived directly from, a cell of the patient, such as a prostate cell, a sample indirectly derived from a patient, such as a cell grown in culture, is also included within the invention. Equally, although the nucleic acid derived from the patient may have been physically within the patient, it may alternatively have been copied from nucleic acid which was physically within the patient. The tumour tissue may be taken from the primary tumour or from metastases, and particularly may be taken from the margins of the tumour.

It will be appreciated that the aforementioned methods may be used for presymptomatic screening of a patient who is in a risk group for cancer. For example, men older than about 60 years may be at greater risk of prostate cancer than men below the age of 35. Similarly, the methods may be used for the pathological classification of tumours such as prostate tumours.

It is preferred that if blood, semen, lymphatic circulation or urine is the source of the said sample containing nucleic acid derived from the patient that the sample is enriched for prostate-derived tissue or cells. Enrichment for prostate cells may be achieved using, for example, cell sorting methods such as fluorescent activated cell sorting (FACS) using a prostate-selective antibody such as one directed to prostate-specific antigen (PSA). Alternatively, enrichment may be achieved using magnetic beads or other solid support, for example a column, coated with such a prostate-specific antibody, for example an anti-PSA antibody. The source of the said sample also includes biopsy material and tumour samples, also including fixed paraffin mounted specimens as well as fresh or frozen tissue.

Conveniently, the nucleic acid capable of selectively hybridising to the said human nucleic acid such as mRNA and which is used in the methods of the invention further comprises a detectable label.

By "detectable label" is included any convenient radioactive label such as $^{32}P$, $^{33}P$ or $^{35}S$ which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Conveniently, the nucleic acid probe may occupy a certain position in a fixed array and whether the nucleic acid hybridises to the said VGSC nucleic acid can be determined by reference to the position of hybridisation in the fixed array.

Primers which are suitable for use in a polymerase chain reaction (PCR; Saiki et al (1988) *Science* 239, 487-491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artifactual product called "primer dimer". When the 3' ends of the two primers hybridize, they form a "primed template" complex, and primer extension results in a short duplex product called "primer dimmer".

Internal secondary structure should be avoided in primers. For symmetric PCR, a 40-60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37-55° C. region, so primer extension will occur during the annealing step and the hybrid will be stabilized. The concentrations of the primers are equal in conventional (symmetric) PCR and, typically, within 0.1- to 1-µM range.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991) *Nature* 350, 91-92 and *AIDS* (1993), Vol 7 (Suppl 2), S108 or SDA (strand displacement amplification) can be used as described in Walker et al (1992) *Nucl. Acids Res.* 20, 1691-1696. The polymerase chain reaction is particularly preferred because of its simplicity.

When a pair of suitable nucleic acids of the invention are used in a PCR it is convenient to detect the product by gel electrophoresis and ethidium bromide staining. As an alternative to detecting the product of DNA amplification using agarose gel electrophoresis and ethidium bromide staining of the DNA, it is convenient to use a labelled oligonucleotide capable of hybridising to the amplified DNA as a probe. When the amplification is by a PCR the oligonucleotide probe hybridises to the interprimer sequence as defined by the two primers. The oligonucleotide probe is preferably between 10 and 50 nucleotides long, more preferably between 15 and 30 nucleotides long. The probe may be labelled with a radionuclide such as $^{32}P$, $^{33}P$ and $^{35}S$ using standard techniques, or may be labelled with a fluorescent dye. When the oligonucleotide probe is fluorescently labelled, the amplified DNA product may be detected in solution (see for example Balaguer et al (1991) "Quantification of DNA sequences obtained by polymerase chain reaction using a bioluminescence adsorbent" *Anal. Biochem.* 195, 105-110 and Dilesare et al (1993) "A high-sensitivity electrochemiluminescence-based detection system for automated PCR product quantitation" *BioTechniques* 15, 152-157.

PCR products can also be detected using a probe which may have a fluorophore-quencher pair or may be attached to a solid support or may have a biotin tag or they may be detected using a combination of a capture probe and a detector probe.

Fluorophore-quencher pairs are particularly suited to quantitative measurements of PCR reactions (eg RT-PCR). Fluorescence polarisation using a suitable probe may also be used to detect PCR products.

In a further preferred embodiment, the level of said VGSC protein is measured. Preferably, the level of said protein is measured by contacting the protein with a molecule which selectively binds to hNe—Na VGSC.

The sample containing protein derived from the patient is conveniently a sample tissue.

The sample containing protein derived from the patient is conveniently a sample of the tissue in which cancer is suspected or in which cancer may be or has been found. These methods may be used for any cancer, but they are particularly suitable in respect of cancer of the prostate. Methods of obtaining suitable samples are described in relation to earlier methods.

The methods of the invention involving detection of the said VGSC proteins are particularly useful in relation to historical samples such as those containing paraffin-embedded sections of tumour samples.

The level of said VGSC protein may be determined in a sample in any suitable way. Example 2 describes the detection of VGSC protein, including hNe—Na VGSC protein, in tissue sections of human prostate.

It is particularly preferred if the molecule which selectively binds to hNe—Na VGSC is an antibody.

Antibodies which can selectively bind to VGSCs or a particular form or forms of VGSC can be made, for example, by using peptides which are respectively conserved in all or in particular VGSCs, or which encompass the differences between one form of VGSC and the other forms.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

The level of said VGSC which is indicative of cancer or metastatic potential may be defined as the increased level present in known cancerous or metastatic prostate cells over known non-cancerous or non-metastatic prostate cells. The level may be, for example, at least 1½ fold higher in cancerous or metastatic cells, or it may be at least 2-fold or 3-fold higher. By "the relative amount of said VGSC protein" is meant the amount of said VGSC protein per unit mass of sample tissue or per unit number of sample cells compared to the amount of said VGSC protein per unit mass of known normal tissue or per unit number of normal cells. The relative amount may be determined using any suitable protein quantitation method. In particular, it is preferred if antibodies are used and that the amount of said VGSC protein is determined using methods which include quantitative western blotting, enzyme-linked immunosorbent assays (ELISA) or quantitative immunohistochemistry.

Other techniques for raising and purifying antibodies are well known in the art and any such techniques may be chosen to achieve the preparations useful in the methods claimed in this invention. In a preferred embodiment of the invention, antibodies will immunoprecipitate said VGSC proteins from solution as well as react with said VGSC protein on western or immunoblots of polyacrylamide gels. In another preferred embodiment, antibodies will detect said VGSC proteins in paraffin or frozen tissue sections, using immunocytochemical techniques.

Preferred embodiments relating to methods for detecting said VGSC protein include enzyme linked immunosorbent assays (ELISA), radioimmunoassay (RIA), immunoradiometric assays (IRMA) and immunoenzymatic assays (EEMA), including sandwich assays using monoclonal and/or polyclonal antibodies. Exemplary sandwich assays are described by David et al in U.S. Pat. Nos. 4,376,110 and 4,486,530, hereby incorporated by reference.

It will be appreciated that other antibody-like molecules may be used in the method of the inventions including, for example, antibody fragments or derivatives which retain their antigen-binding sites, synthetic antibody-like molecules such as single-chain Fv fragments (ScFv) and domain antibodies (dAbs), and other molecules with antibody-like antigen binding motifs.

In a further embodiment the level of hNe—Na VGSC is measured by selectively assaying its activity in the sample. The activity of VGSC, for example hNe—Na VGSC, in a sample may be assayed by dissociating a biopsy into single cells and in culture assaying (i) the effect of $Na^+$ channel blockers on their motility and (ii) detecting $Na^+$ channel activity by electrophysiological recording.

Preferred diagnostic methods of the invention include what can broadly be described as "invasive" methods and "non-invasive" methods. Invasive methods include, for example, the taking of a biopsy for detection of $Na^+$ channel expression by, for example, (a) immunohistochemical application of a sequence-specific antibody, (b) in situ PCR on tissue sections, or (c) reverse transcription (RT)-PCR of epithelial cells after separating them from the biopsy. Non-invasive methods include obtaining prostate-derived cells from urine, ejaculate or blood, which may be separated by affinity to PSA, and assayed for $Na^+$ channel expression by PCR.

A further aspect of the invention provides use of an agent which is capable of use in determining the level of hNe—Na voltage-gated $Na^+$ channel protein or nucleic acid in a sample in the manufacture of a reagent for diagnosing cancer. The agent may suitably be a nucleic acid which selectively hybridises to hNe—Na VGSC nucleic acid or the agent may be a molecule which selectively binds to hNe—Na VGSC protein or the agent may be an agent useful in selectively assaying the activity of hNe—Na VGSC.

The agents as defined are therefore useful in a method of diagnosing cancer.

A further aspect of the invention comprises a kit of parts useful for diagnosing cancer, especially prostate cancer, comprising an agent which is capable of use in determining the level of hNe—Na VGSC protein or nucleic acid in a sample. The agent may be a nucleic acid which selectively hybridises to hNe—Na VGSC nucleic acid or the agent may be a molecule which selectively binds to hNe—Na VGSC protein or the agent may be an agent useful in selectively assaying the activity of heNe-Na VGSC.

Preferably, the kit further comprises a control sample containing hNe—Na VGSC nucleic acid or protein wherein the control sample may be a negative control (which contains a level of VGSC protein or nucleic acid which is not associated with cancer or a high metastatic potential for cancer) or it may be a positive control (which contains a level of VGSC protein or nucleic acid which is associated with cancer or a high metastatic potential for cancer). The kit may contain both negative and positive controls. The kit may usefully contain controls of hNe—Na VGSC protein or nucleic acid which correspond to different amounts such that a calibration curve may be made.

Suitably, the kit further comprises means for separating prostatic epithelial cells from a sample in order to carry out said VGSC assay. Preferably, the means for separating prostatic epithelial cells includes anti PSA-antibody-coated micro-beads or columns.

A further aspect of the invention provides a method of treating cancer comprising the step of administering to the patient an agent which selectively prevents the function of hNe—Na voltage-gated Na+ channel.

As will be apparent to the skilled person, the term "prevents" encompasses partial prevention of the function ie reduction of the function. Thus, the effect of the agent may appear as reduction, preferably marked reduction, of the observed function.

By "an agent which selectively prevents the function of hNe—Na VGSC" we include agents that (a) inhibit the expression of said VGSCs or (b) inhibit the activity of said VGSCs.

Agents that prevent the function of hNe—Na VGSC may include antagonists of epidermal growth factor (EGF) (which antagonist may be an antibody reactive with EGF or its receptor (EGFR)) and antagonists of other growth factors (for example nerve growth factor) and hormones (including androgens) (which antagonist may similarly be an antibody). Thus, an EGF receptor kinase inhibitor or an EGF receptor antibody may inhibit VGSC function (which is predominantly hNe—Na) in a prostate cancer cell line, as discussed in Example 4. These agents may act as agents that prevent the expression of hNe—Na VGSCs.

EGF antagonists may include monoclonal antibodies (for example cetuximab [IMC-C225]) directed against the extracellular binding domain of the EGF receptor; Trastuzumab (a monoclonal antibody binding to the HER2 receptor (human EGF receptor 2); an EGF receptor kinase inhibitor, for example OSI-774, PD182905, PKI-166, CI-1033 or ZD1839.

Agents that prevent the expression of said VGSCs include but are not limited to antisense agents and ribozymes.

Antisense oligonucleotides are single-stranded nucleic acid, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A) addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci. (USA)* 85(15), 5507-11). The Goodchild study showed that oligonucleotides that were most effective were complementary to the poly(A) signal; also effective were those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079-7083 showed increased inhibition in tissue culture of HIV-1 using oligonucleotide phosphoramidates and phosphorothioates. Sarin et al (1988) *Proc. Natl. Acad. Sci. USA* 85, 7448-7451 demonstrated increased inhibition of HIV-1 using oligonucleotide methylphosphonates. Agrawal et al (1989) *Proc. Natl. Acad. Sci. USA* 86, 7790-7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430-3434 report inhibition in tissue culture of influenza virus replication by oligonucleotide phosphorothioates.

Oligonucleotides having, artificial linkages have been shown to be resistant to degradation in vivo. For example, Shaw et al (1991) in *Nucleic Acids Res.* 19, 747-750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesizing oligonucleoside phosphorothioates is provided in Agrawal and Tang (1990) *Tetrahedron Letters* 31, 7541-7544, the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) Tetrahedron Letters 28, 3401; Bannwarth (1988) *Helv. Chim. Acta.* 71, 1517; Crosstick and Vyle is (1989) *Tetrahedron Letters* 30, 4693; Agrawal et al (1990) *Proc. Natl. Acad. Sci. USA* 87, 1401-1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesized and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747-750 and Agrawal et al (1991) *Proc. Natl. Acad. Sci. USA* 88(17), 7595-7599, the teachings of which are hereby incorporated herein by reference.

A further method of making oligonucleotides resistant to nuclease attack is for them to be "self-stabilized" as described by Tang et al (1993) *Nucl. Acids Res.* 21, 2729-2735 incorporated herein by reference. Self-stabilized oligonucleotides have hairpin loop structures at their 3' ends, and show increased resistance to degradation by snake venom phosphodiesterase, DNA polymerase I and fetal bovine serum. The self-stabilized region of the oligonucleotide does not interfere in hybridization with complementary nucleic acids, and pharmacokinetic and stability studies in mice have shown increased in vivo persistence of self-stabilized oligonucleotides with respect to their linear counterparts.

In accordance with the invention, the inherent binding specificity of antisense oligonucleotides characteristic of base pairing is enhanced by limiting the availability of the antisense compound to its intend locus in vivo, permitting lower dosages to be used and minimizing systemic effects. Thus, oligonucleotides are applied locally to achieve the desired effect. The concentration of the oligonucleotides at the desired locus is much higher than if the oligonucleotides were administered systemically, and the therapeutic effect can be achieved using a significantly lower total amount. The local high concentration of oligonucleotides enhances penetration of the targeted cells and effectively blocks translation of the target nucleic acid sequences.

The oligonucleotides can be delivered to the locus by any means appropriate for localized administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus.

The oligonucleotides may be administered via a hydrogel material. The hydrogel is noninflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10 to about 80% by weight ethylene oxide and from about 20 to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warms, it solidifies to form a gel, and the oligonucleotides diffuse out of the gel into the surrounding cells over a period of time defined by the exact composition to of the gel.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerized or solidified, using melt or solvent evaporation techniques, or mechanically mixed with the material. In one embodiment, the oligonucleotides are mixed into or applied onto coatings for implantable devices such as dextran coated silica beads, stents, or catheters. Polymeric nanoparticles/biodegradable drug carriers may also be used (Mader (1998) *Radiol. Oncol.* 32, 89-94).

The dose of oligonucleotides is dependent on the size of the oligonucleotides and the purpose for which it is administered. In general, the range is calculated based on the surface area of tissue to be treated. The effective dose of oligonucleotide is somewhat dependent on the length and chemical composition of the oligonucleotide but is generally in the range of about 30 to 3000 µg per square centimetre of tissue surface area.

The oligonucleotides may be administered to the patient systemically for both therapeutic and prophylactic purposes. The oligonucleotides may be administered by any effective method, for example, parenterally (eg intravenously, subcutaneously, intramuscularly) or by oral, nasal or other means which permit the oligonucleotides to access and circulate in the patient's bloodstream. Oligonucleotides administered systemically preferably are given in addition to locally administered oligonucleotides, but also have utility in the absence of local administration. A dosage in the range of from about 0.1 to about 10 grams per administration to an adult human generally will be effective for this purpose.

It will be appreciated that it may be desirable to target the antisense oligonucleotides to the prostate. This may be achieved by administering the antisense oligonucleotides to the prostate, or it may be achieved by using antisense oligonucleotides which are in association with a molecule which selectively directs the antisense oligonucleotide to the prostate. For example, the antisense oligonucleotide may be associated with an antibody or antibody like molecule which selectively binds a prostate-related antigen such as PSA. By "associated with" we mean that the antisense oligonucleotide and the prostate-directing entity are so associated that the prostate-directing entity is able to direct the antisense oligonucleotide to the prostate cells.

It will be appreciated that antisense agents also include larger molecules, for example of around one hundred to several hundred bases which bind to said VGSC mRNA or genes and substantially prevent expression of said VGSC mRNA or genes and substantially prevent expression of said VGSC protein. Thus, expression of an antisense molecule which is substantially complementary to said VGSC mRNA is envisaged as part of the invention.

Thus, in this approach, synthetic oligonucleotides with antisense sequence to specific regions of (i) hNe—Na channels or (ii) VGSCs generally are administered to block channel activity. Details of particular synthetic oligonucleotides are given in Example 2. It is noteworthy that antisense oligonucleotide technology has already been used to manipulate potassium channels in vitro (Roy et al (1996) Glia 18, 174-188) and VGSCs in vitro (*Biochem Biophys Res Comm* (1997) 234, 235-241) and in blocking neuropathic pain (Lai et al (1999) "Blockade of neuropathic pain by antisense targeting of tetrodotoxin-resistant sodium channels in sensory neurons" *Methods in Enzymol* 314, 201-213).

A further method for blocking said VGSC activity includes dominant negative suppression. In this technique, a mutated VGSC gene product suppresses or eliminates the activity of the corresponding normal gene product when the two are co-expressed. In the case of voltage-gated potassium channels (VGPCs) which comprise 4 alpha subunits, such an approach making use of a highly truncated gene product, has been used successfully to suppress functional expression of VGPCs in vitro (Tu et al (1995) *Biophys. J* 68, 147-156) and in vivo (London et al (1998) *Proc. Natl. Acad. Sci. USA* 95, 2926-2931). The truncated subunit is capable of binding to other VGPC subunits but does not contain the residues required for channel functioning. Thus, the activity of the "combined" VGPC is blocked. A number of naturally occurring alternatively spliced channel subunits have been detected which may function to suppress VGPC activity by a similar mechanism in vivo (Baumann et al (1987) *EMBO J.* 6, 3419-3429; Kamb et al (1988) *Neuron* 1, 421-430; and Pongs et al (1988) *EMBO J.* 7, 1087-1096). We believe that VGSC may similarly be suppressed by interfering with functional channel formation. Although VGSCs are formed from a single alpha subunit (comprising four functional domains), recent studies have demonstrated the specific expression (during development in human, mouse and fish) of truncated VGSC proteins possessing only two domains which might function in a dominant negative manner to control VGSC activity (Plummer et al (1997) *J. Biol. Chem.* 272, 24008-24015; and Oh & Waxman (1998) *NeuroReport* 9, 1267-1271).

The larger molecules may be expressed from any suitable genetic construct as is described below and delivered to the patient. Typically, the genetic construct which expresses the antisense molecule comprises at least a portion of the said VGSC cDNA or gene operatively linked to a promoter which can express the antisense molecule in the cell, preferably prostate cell, which is or may become cancerous.

Although the genetic construct can be DNA or RNA it is preferred if it is DNA.

Preferably, the genetic construct is adapted for delivery to a human cell.

Means and methods of introducing a genetic construct into a cell in an animal body are known in the art. For example, the constructs of the invention may be introduced into the tumour cells by any convenient method, for example methods involving retroviruses, so that the construct is inserted into the genome of the tumour cell. For example, in Kuriyama et al (1991) *Cell Struc. and Func.* 16, 503-510 purified retroviruses are administered. Retroviruses provide a potential means of selectively infecting cancer cells because they can only integrate into the genome of dividing cells; most normal cells surrounding cancers are in a quiescent, non-receptive stage of cell growth or, at least, are dividing much less rapidly than the tumour cells. Retroviral DNA constructs which encode said antisense agents may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo gene). Independent colonies are isolated and expanded and the culture supernatant removed, filtered through a 0.45:m pore-size filter and stored at −70°. For the introduction of the retrovirus into the tumour cells, it is convenient to inject directly retroviral supernatant to which 10 μg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992) *Science* 256, 1550-1552, cells which produce retroviruses are injected into the tumour. The retrovirus-producing cells so introduced are engineered to actively produce retroviral vector particles so that continuous productions of the vector occurred within the tumour mass in situ. Thus, proliferating tumour cells can be successfully transduced in vivo if mixed with retroviral vector-producing cells.

Targeted retroviruses are also available for use in the invention; for example, sequences conferring specific binding affinities may be engineered into preexisting viral env genes (see Miller & Vile (1995) *Faseb J.* 9, 190-199 for a review of this and other targeted vectors for gene therapy).

Other methods involve simple delivery of the construct into the cell for expression therein either for a limited time or, following integration into the genome, for a longer time. An example of the latter approach includes (preferably tumour-cell-targeted) liposomes (Nassander et al (1992) *Cancer Res.* 52, 646-653).

Immunoliposomes (antibody-directed liposomes) are especially useful in targeting to cancer cell types which over-express a cell surface protein for which antibodies are available. For example, the immunoliposomes may be targeted by means of antibodies binding to the said VGSC, as discussed further below. For the preparation of immuno-liposomes MPB-PE (N-[4-(p-maleimidophenyl)butyryl]-phosphatidylethanolamine) is synthesised according to the method of Martin & Papahadjpoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 μm and 0.2 μm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour.

Other methods of delivery include adenoviruses carrying external DNA via an antibody-polylysine bridge (see Curiel

*Prog. Med. Virol.* 40, 1-18) and transferrin-polycation conjugates as carriers (Wagner et al (1990) *Proc. Natl. Acad. Sci. USA* 87, 3410-3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalized into the cell and carries into the cell with it the DNA construct of the invention. It is preferred if the polycation is polylysine.

The DNA may also be delivered by adenovirus wherein it is present within the adenovirus particle, for example, as described below.

In the second of these methods, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) *Proc. Natl. Acad. Sci. USA* 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It may be desirable to locally perfuse a tumour with the suitable delivery vehicle comprising the genetic construct for a period of time; additionally or alternatively the delivery vehicle or genetic construct can be injected directly into accessible tumours.

It will be appreciated that "naked DNA" and DNA complexed with cationic and neutral lipids may also be useful in introducing the DNA of the invention into cells of the patient to be treated. Non-viral approaches to gene therapy are described in Ledley (1995) *Human Gene Therapy* 6, 1129-1144.

Alternative targeted delivery systems are also known such as the modified adenovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Mutant adenoviruses which replicate selectively in p53-deficient human tumour cells, such as those described in Bischoff et al (1996) *Science* 274, 373-376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

In a further embodiment the agent which selectively prevents the function of hNe—Na VGSC is a ribozyme capable of cleaving targeted VGSC RNA or DNA. A gene expressing said ribozyme may be administered in substantially the same way and using substantially the same vehicles as for the antisense molecules.

Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

It will be appreciated that it may be desirable that the antisense molecule or ribozyme is expressed from a prostate cell-specific promoter element. Prostate-specific antigen (PSA) is one of the major protein constituents of the human prostate secretion. It has become a useful marker for the detection and monitoring of prostate cancer. The gene encoding PSA and its promoter region which directs the prostate-specific expression of PSA have been described (Lundwall (1989) *Biochem. Biophys. Res. Comm.* 161, 1151-1159; Riegman et al (1989) *Biochem. Biophys. Res. Comm.* 159, 95-102; Brawer (1991) *Acta Oncol.* 30, 161-168). Thus, suitably, the promoter is the PSA promoter.

The genetic constructs of the invention can be prepared using methods well known in the art.

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487-491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The present invention also relates to a host cell transformed with a genetic (preferably DNA construct) construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25 pFD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the molecule as defined in the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the molecule, for example a protein, in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

When the genetic construct is a plasmid DNA construct it can be purified. The DNA construct of the invention is purified from the host cell using well known methods.

For example, plasmid vector DNA can be prepared on a large scale from cleaved lysates by banding in a CsCl gradient according to the methods of Clewell & Helinski (1970) *Biochemistry* 9, 4428-4440 and Clewell (1972) *J. Bacteriol.* 110, 667-676. Plasmid DNA extracted in this way can be freed from CsCl by dialysis against sterile, pyrogen-free buffer through Visking tubing or by size-exclusion chromatography.

Alternatively, plasmid DNA may be purified from cleared lysates using ion-exchange chromatography, for example those supplied by Qiagen. Hydroxyapatite column chromatography may also be used.

A further aspect of the invention provides use of an agent which selectively prevents the function of hNe—Na voltage-gated $Na^+$ channel in the manufacture of a medicament for treating cancer.

A still further aspect of the invention provides a genetic construct comprising a nucleic acid encoding a molecule capable of preventing the function of hNe—Na voltage-gated $Na^+$ channel expressed in a cell.

As noted above, the genetic construct may be RNA or DNA. The molecule capable of preventing the function of hNe—Na VGSC is conveniently an antisense molecule or a ribozyme as disclosed above.

The genetic constructs are adapted for delivery to a human cell, in particular a cell which is cancerous or in which cancer may occur, and more particularly the genetic construct is adapted for delivery to a prostate cell. The genetic constructs of this aspect of the invention include the viral and non-viral delivery systems described above.

Suitably, the molecule is capable of preventing the function of VGSC, for example hNe—Na VGSC, such as a ribozyme or antisense molecule, is selectively expressed in a cancer cell. For example, expression of said molecule by the genetic construct may be via a cancer cell- or tissue-selective promoter which, in the case of prostate cancer, may be the PSA promoter or any other prostate-selective promoter.

A further aspect of the invention provides the genetic constructs for use in medicine. Thus, the genetic constructs are packaged and presented for use in medicine.

A further aspect of the invention provides a pharmaceutical composition comprising a genetic construct of the invention and a pharmaceutically acceptable carrier. The carriers must be "acceptable" in the sense of being compatible with the genetic construct of the invention and not deleterious to the recipients thereof. Typically, the carriers will be water or saline which will be sterile and pyrogen free.

For the avoidance of doubt, the genetic constructs of the invention specifically include virus or virus-like particles.

A further aspect of the invention provides a method of identifying a compound which selectively inhibits a hNe—Na voltage-gated Na$^+$ channel, the method comprising (a) contacting a test compound with any one of the said voltage-gated Na$^+$ channels and determining whether said compound is inhibitory; (b) contacting the test compound with other voltage-gated Na$^+$ channels and determining whether said compound is inhibitory; and (c) selecting a compound which is substantially inhibitory in (a) but is not substantially inhibitory in (b).

Typically, a range of compounds, including pharmacological agents with known effects upon Na$^+$ channels (for example compounds with effects similar to terodotoxin) or physiological (for example growth factors or hormones, for example epidermal growth factor or androgens), will be screened for their effectiveness in a number of assays. Suitable assay formats include electrophysiological recording from cells in long-term culture as cell-lines and short term culture of cells dissociated from biopsies (see, for example Grimes & Djamgoz (1998) *J. Cell Physiol.* 175, 50-58); electrophysiological recording from oocytes functionally expressing recombinant said VGSC following injection of cRNAs (see, for example, Fraser et al (1993) *In Electrophysiology, A practical approach* (D. Willis, ed) IRL Press); and in vitro (Boyden chamber) invasion assays (see, for example, Grimes et al (1995) *FEBS Lett* 369, 290-294; and Smith et al (1998) *FEBS Lett.* 423, 19-24). Suitable assays may also include measurement of effects on PSA secretion from prostate cancer cell lines, for example as described in Abdul & Hoosein (2001) *Anticancer Res* 21, 2045-2048.

The present invention also provides methods in which treatment is targeted to cancer cells by means of targeting to cells expressing the said VGSC, as noted above in relation to targeting of genetic constructs to such cells. For example, anti-said VGSC antibodies (VGSC-Abs) conjugated with a dye substance may be applied to the prostate gland in vivo (eg Yasmuch et al (1993) "Antibody targeted photolysis" *Critical Review Revue Ther. Drug Carrier System* 10, 197-252; Pogrebniak et al (1993) "Targetted phototherapy with sensitizer-monoclonal antibody conjugate and light" *Surgical Onoclogy* 2, 31-42). The gland is then irradiated locally with a wavelength of light/laser matching the absorption peak of the 'attached' dye. Absorption of the light energy by the dye leads to local heating and cell death. In this way, only the labelled (ie metastatic) cells will be ablated. VGSC-Abs labelled with the following dyes may be used: fluorescein (Pelegrin et al (1991) "Antibody fluorescein conjugates for photoimmunodiagnosis of human colon-carcinoma in nude-mice" *Cancer* 67, 2529-2537); rhodamine (Haghighat et al (1992) "Laser-dyes for experimental phototherapy of human cancer—comparison of 3 rhodamines" *Laryngoscope* 102, 81-87); cyanins (Folli et al (1994) "Antibody-indocyanin conjugates for immunophotodetection of human squamous-cell carcinoma in nude-mice" *Cancer Research* 54, 2643-2649; Lipshutz et al (1994) "Evaluation of 4 new carbocyanine dyes for photodynamic therapy with lasers" *Laryngoscope* 104, 996-1002; Haddad et al (1998) "In vitro and in vivo effects of photodynamic therapy on murine malignant melanoma" *Annals of Surgical Oncology* 5, 241-247).

Thus, a further aspect of the invention provides a compound comprising a moiety which selectively binds hNe—Na voltage-gated Na$^+$ channel protein and a further moiety.

By "a moiety which selectively binds hNe—Na voltage-gated Na$^+$ channel protein" we mean any suitable such moiety which binds the said VGSC but does not substantially bind other molecules, for example other VGSCs. The compound comprising the binding moiety is one which preferably, in use, is able to localise to areas of cancerous cells, particularly metastatic cancer cells, but not localise substantially to other areas where there are no cancerous cells.

Preferably the binding moiety is able to bind to the said VGSC with high affinity. For example, the binding constant for the binding of the binding moiety to the said VGSC is preferably between $10^{-7}$ and $10^{-10}$ M. Typically the binding moiety is an anti-hNe—Na antibody. Such antibodies and methods of preparing suitable antibodies are discussed above.

The further moiety may be any further moiety which confers on the compound a useful property with respect to the treatment or imaging or diagnosis of cancer. In particular, the further moiety is one which is useful in killing or imaging cancer cells, particularly metastatic cancer cells. Preferably, the further moiety is one which is able to kill the cancer cells to which the compound is targeted.

In a preferred embodiment of the invention the further moiety is directly or indirectly cytotoxic. In particular the further moiety is preferably directly or indirectly toxic to cancer cells, particularly metastatic cancer cells.

By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it.

In one embodiment the cytotoxic moiety is a cytotoxic chemotherapeutic agent. Cytotoxic chemotherapeutic agents are well known in the art.

Cytotoxic chemotherapeutic agents, such as anticancer agents, include: alkylating agents including nitrogen mustards such as mechlorethamine (HN$_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2-□-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p□-DDD) and aminoglutethimide; taxol and analogues/ derivatives; and hormone agonists/antagonists such as flutamide and tamoxifen.

Various of these agents have previously been attached to antibodies and other target site-delivery agents, and so compounds of the invention comprising these agents may readily be made by the person skilled in the art. For example, carbodiimide conjugation (Bauminger & Wilchek (1980) *Methods Enzymol.* 70, 151-159; incorporated herein by reference) may be used to conjugate a variety of agents, including doxorubicin, to antibodies or peptides.

Carbodiimides comprise a group of compounds that have the general formula R—N=C=N—R', where R and R' can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups.

The water soluble carbodiimide, 1-ethyl-3-(3-dimethylaminopropyl) carbodiimide (EDC) is particularly useful for conjugating a functional moiety to a binding moiety and may be used to conjugate doxorubicin to tumor homing peptides. The conjugation of doxorubicin and a binding moiety requires the presence of an amino group, which is provided by doxorubicin, and a carboxyl group, which is provided by the binding moiety such as an antibody or peptide.

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger & Wilchek, supra, 1980).

Other methods for conjugating a functional moiety to a binding moiety also can be used. For example, sodium periodate oxidation followed by reductive alkylation of appropriate reactants can be used, as can glutaraldehyde crosslinking. However, it is recognised that, regardless of which method of producing a conjugate of the invention is selected, a determination must be made that the binding moiety maintains its targeting ability and that the functional moiety maintains its relevant function.

In a further embodiment of the invention, the cytotoxic moiety is a cytotoxic peptide or polypeptide moiety by which we include any moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. The use of ricin as a cytotoxic agent is described in Burrows & Thorpe (1993) *Proc. Natl. Acad. Sci. USA* 90, 8996-9000, incorporated herein by reference, and the use of tissue factor, which leads to localised blood clotting and infarction of a tumour, has been described by Ran et al (1998) *Cancer Res.* 58, 4646-4653 and Huang et al (1997) *Science* 275, 547-550. Tsai et al (1995) *Dis. Colon Rectum* 38, 1067-1074 describes the abrin A chain conjugated to a monoclonal antibody and is incorporated herein by reference. Other ribosome inactivating proteins are described as cytotoxic agents in WO 96/06641. *Pseudomonas* exotoxin may also be used as the cytotoxic polypeptide moiety (see, for example, Aiello et al (1995) *Proc. Natl. Acad. Sci. USA* 92, 10457-10461; incorporated herein by reference).

Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the binding moiety in known ways. For example EDTA or another chelating agent may be attached to the binding moiety and used to attach $^{111}$In or $^{90}$Y. Tyrosine residues may be labelled with $^{125}$I or $^{131}$I.

The cytotoxic moiety may be a suitable indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody this type of system is often referred to as ADEPT (Antibody-Directed Enzyme Prodrug Therapy). The system requires that the targeting moiety locates the enzymatic portion to the desired site in the body of the patient (ie the site expressing the said VGSC, such as metastatic cancer cells) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (see Senter, P. D. et al (1988) "Anti-tumor effects of antibody-alkaline phosphatase conjugates in combination with etoposide phosphate" *Proc. Natl. Acad. Sci. USA* 85, 4842-4846; Bagshawe (1987) *Br. J. Cancer* 56, 531-2; and Bagshawe, K. D. et al (1988) "A cytotoxic agent can be generated selectively at cancer sites" *Br. J. Cancer.* 58, 700-703.)

Clearly, any said VGSC-binding moiety may be used in place of an anti-hNe—Na antibody in this type of directed enzyme prodrug therapy system.

The enzyme and prodrug of the system using a said VGSC-targeted enzyme as described herein may be any of those previously proposed. The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include: a phenol mustard prodrug activated by an *E. coli* β-glucuronidase (Wang et al, 1992 and Roffler et al, 1991); a doxorubicin prodrug activated by a human β-glucuronidase (Bosslet et al, 1994); further doxorubicin prodrugs activated by coffee bean α-galactosidase (Azoulay et al, 1995); daunorubicin prodrugs, activated by coffee bean α-D-galactosidase (Gesson et al, 1994); a 5-fluorouridine prodrug activated by an *E. coli* β-D-galactosidase (Abraham et al, 1994); and methotrexate prodrugs (eg methotrexate-alanine) activated by carboxypeptidase A (Kuefner et al, 1990, Vitols et al, 1992 and Vitols et al, 1995). These and others are included in the following table.

| Enzyme | Prodrug |
|---|---|
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate<br>Mitomycin phosphate |
| Beta-glucuronidase | p-Hydroxyaniline mustard-glucuronide<br>Epirubicin-glucuronide |
| Penicillin-V-amidase | Adriamycin-N phenoxyacetyl |
| Penicillin-G-amidase | N-(4'-hydroxyphenyl acetyl) palytoxin<br>Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-glucopyranosiduronic acid |
| Nitroreductase | 5-(Aziridin-1-yl-)-2,4-dinitrobenzamide |
| Cytosine deaminase | 5-Fluorocytosine |
| Carboxypeptidase A | Methotrexate-alanine |

(This table is adapted from Bagshawe (1995) *Drug Dev. Res.* 34, 220-230, from which full references for these various systems may be obtained; the taxol derivative is described in Rodrigues, M. L. et al (1995) *Chemistry & Biology* 2, 223).

Suitable enzymes for forming part of the enzymatic portion of the invention include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as eg thrombolysin (for thrombin prodrugs); hydrolases, such as phosphatases (eg alkaline phosphatase) or sulphatases (eg aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB 1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

The prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

When each moiety of the compound is a polypeptide, the two portions may be linked together by any of the conventional ways of cross-linking polypeptides, such as those generally described in O'Sullivan et al (1979) *Anal. Biochem.* 100, 100-108. For example, the said VGSC binding moiety may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, the compound may be produced as a fusion compound by recombinant DNA techniques whereby a length of DNA comprises respective regions encoding the two moieties of the compound of the invention either adjacent one another or separated by a region encoding a linker peptide which does not destroy the desired properties of the compound. Conceivably, the two portions of the compound may overlap wholly or partly.

The DNA is then expressed in a suitable host to produce a polypeptide comprising the compound of the invention.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst.* 88, 1193-11203; Shewach & Lawrence (1996) *Invest. New Drugs* 14, 257-263; Horsman (1995) *Acta Oncol.* 34, 571-587; Shenoy & Singh (1992) *Clin. Invest.* 10, 533-551; Mitchell et al (1989) *Int. J. Radiat. Biol.* 56, 827-836; Iliakis & Kurtzman (1989) *Int. J. Radiat. Oncol. Biol. Phys.* 16, 1235-1241; Brown (1989) *Int. J. Radiat. Oncol. Biol. Phys.* 16, 987-993; Brown (1985) *Cancer* 55, 2222-2228).

Also, delivery of genes into cells can radiosensitise them, for example delivery of the p53 gene or cyclin D (Lang et al (1998) *J. Neurosurg.* 89, 125-132; Coco Martin et al (1999) *Cancer Res.* 59, 1134-1140).

The further moiety may be one which becomes cytotoxic, or releases a cytotoxic moiety, upon irradiation. For example, the boron-10 isotope, when appropriately irradiated, releases α particles which are cytotoxic (see for example, U.S. Pat. No. 4,348,376 to Goldenberg; Primus et al (1996) *Bioconjug. Chem.* 7, 532-535).

Similarly, the cytotoxic moiety may be one which is useful in photodynamic therapy such as photofrin (see, for example, Dougherty et al (1998) *J. Natl. Cancer Inst.* 90, 889-905).

The further moiety may comprise a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis.

Examples of suitable oligonucleotides include those directed at bcl-2 (Ziegler et al (1997) *J. Natl. Cancer Inst.* 89, 1027-1036), and DNA polymerase α and topoisomerase IIa (Lee et al (1996) *Anticancer Res.* 16, 1805-1811.

Peptide nucleic acids may be useful in place of conventional nucleic acids (see Knudsen & Nielsen (1997) *Anticancer Drugs* 8, 113-118).

In a further embodiment, the binding moiety may be comprised in a delivery vehicle for delivering nucleic acid to the target, for example a nucleic acid as discussed in relation to earlier aspects of the invention. The delivery vehicle may be any suitable delivery vehicle. It may, for example, be a liposome containing nucleic acid, or it may be a virus or virus-like particle which is able to deliver nucleic acid. In these cases, the moiety which selectively binds to the said VGSC is typically present on the surface of the delivery vehicle. For example, the moiety which selectively binds to the said VGSC, such as a suitable antibody fragment, may be present in the outer surface of a liposome and the nucleic acid to be delivered may be present in the interior of the liposome. As another example, a viral vector, such as a retroviral or adenoviral vector, is engineered so that the moiety which selectively binds to the said VGSC is attached to or located in the surface of the viral particle thus enabling the viral particle to be targeted to the desired site. Targeted delivery systems are also known, such as the modified adenovirus system discussed above.

Immunoliposomes (antibody-directed liposomes) may be used in which the moiety which selectively binds to the said VGSC is an antibody. The preparation of immunoliposomes is described above.

The nucleic acid delivered to the target site may be any suitable DNA which leads, directly or indirectly, to cytotoxicity. For example, the nucleic acid may encode a ribozyme which is cytotoxic to the cell, or it may encode an enzyme which is able to convert a substantially non-toxic prodrug into a cytotoxic drug (this latter system is sometime called GDEPT: Gene Directed Enzyme Prodrug Therapy).

Ribozymes which may be encoded in the nucleic acid to be delivered to the target are described in references cited above. Suitable targets for ribozymes include transcription factors such as c-fos and c-myc, and bcl-2. Durai et al (1997) *Anticancer Res.* 17, 3307-3312 describes a hammerhead ribozyme against bcl-2.

EP 0 415 731 describes the GDEPT system. Similar considerations concerning the choice of enzyme and prodrug apply to the GDEPT system as to the ADEPT system described above.

The nucleic acid delivered to the target site may encode a directly cytotoxic polypeptide.

In a further embodiment of the invention, the further moiety comprised in the compound of the invention is a readily detectable moiety.

By a "readily detectable moiety" we include the meaning that the moiety is one which, when located at the target site following administration of the compound of the invention into a patient, may be detected, typically non-invasively from outside the body and the site of the target located. Thus, the compounds of this embodiment of the invention are useful in imaging and diagnosis.

Typically, the readily detectable moiety is or comprises a radioactive atom which is useful in imaging. Suitable radioactive atoms include technetium-99m or iodine-123 for scinitgraphic studies. Other readily detectable moieties include, for example, spin labels for magnetic resonance imaging (MRI) such as iodine-123 again, iodine-131, indium-111, fluorine-19, carbon-13, nitrogen-15, oxygen-17, gadolinium, manganese or iron. Clearly, the compound of the invention must have sufficient of the appropriate atomic isotopes in order for the molecule to be readily detectable.

The radio- or other labels may be incorporated in the compound of the invention in known ways. For example, if the binding moiety is a polypeptide it may be biosynthesized or may be synthesized by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{11}$In can, for example, be attached via cysteine residues in the binding moiety. Yttrium-90 can be attached via a lysine residue. The IODOGEN method (Fraker er al (1978) Biochem. *Biophys. Res. Comm.* 80, 49-57) can be used to incorporate iodine-123. Reference ("Monoclonal Antibodies in Immunoscintigraphy", J-F Chatal, CRC Press, 1989) describes other methods in detail.

In a further preferred embodiment of the invention the further moiety is able to bind selectively to a directly or indirectly cytotoxic moiety or to a readily detectable moiety. Thus, in this embodiment, the further moiety may be any moiety which binds to a further compound or component which is cytotoxic or readily detectable.

The further moiety may, therefore be an antibody which selectively binds to the further compound or component, or it may be some other binding moiety such as streptavidin or biotin or the like. The following examples illustrate the types of molecules that are included in the invention; other such molecules are readily apparent from the teachings herein.

A bispecific antibody wherein one binding site comprises the moiety which selectively binds to the said VGSC and the second binding site comprises a moiety which binds to, for example, an enzyme which is able to convert a substantially non-toxic prodrug to a cytotoxic drug.

The compound may be an antibody which selectively binds to the said VGSC, to which is bound biotin. Avidin or streptavidin which has been labelled with a readily detectable label may be used in conjunction with the biotin labelled antibody in a two-phase imaging system wherein the biotin labelled antibody is first localised to the target site in the patient, and then the labelled avidin or streptavidin is administered to the patient. Bispecific antibodies and biotin/streptavidin (avidin) systems are reviewed byRosebrough (1996) *Q J Nucl. Med.* 40, 234-251.

In a preferred embodiment of the invention, the moiety which selectively binds to the said VGSC and the further moiety are polypeptides which are fused.

A further aspect of the invention comprises a nucleic acid molecule encoding a compound of the preceding aspect of the invention.

A further aspect of the invention provides a compound of the invention for use in medicine. Typically, the compound is packaged and presented as a medicament or as an imaging agent or as a diagnostic agent for use in a patient.

A still further aspect of the invention provides a pharmaceutical composition comprising a compound according to the invention and a pharmaceutically acceptable carrier.

Typically the pharmaceutical compositions or formulations of the invention are for parenteral administration, more particularly for intravenous administration.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

A still further aspect of the invention provides the use of a compound of the invention in the manufacture of a medicament for the treatment and/or diagnosis of a human patient with or at risk of cancer.

A still further aspect of the invention comprises a method of treating cancer the method comprising administering to the human patient an effective amount of a compound of the invention wherein the further moiety of the compound is one which either directly or indirectly is of therapeutic benefit to the patient.

A still further aspect of the invention comprises a method of imaging cancer (which may be useful in determining the susceptibility of a human patient to cancer, or of diagnosing cancer in a human patient, or of predicting the relative prospects of a particular outcome of a cancer) in a human patient, comprising administering to the patient an effective amount of a compound of the invention wherein the further moiety of the compound is one which comprises a readily detectable moiety.

It will readily be appreciated that, depending on the particular compound used in treatment, imaging or diagnosis, the timing of administration may vary and the number of other components used in therapeutic systems disclosed herein may vary.

For example, in the case where the compound of the invention comprises a readily detectable moiety or a directly cytotoxic moiety, it may be that only the compound, in a suitable formulation, is administered to the patient. Of course, other agents such as immunosuppressive agents and the like may be administered.

In respect of compounds which are detectably labelled, imaging takes place once the compound has localised at the target site.

However, if the compound is one which requires a further component in order to be useful for treatment, imaging or diagnosis, the compound of the invention may be administered and allowed to localise at the target site, and then the further component administered at a suitable time thereafter.

For example, in respect of the ADEPT and ADEPT-like systems above, the binding moiety-enzyme moiety compound is administered and localises to the target site. Once this is done, the prodrug is administered.

Similarly, for example, in respect of the compounds wherein the further moiety comprised in the compound is one which binds a further component, the compound may be administered first and allowed to localise at the target site, and subsequently the further component is administered.

Thus, in one embodiment a biotin-labelled anti-hNe—Na antibody is administered to the patient and, after a suitable period of time, detectably labelled streptavidin is administered. Once the streptavidin has localised to the sites where the antibody has localised (ie the target sites) imaging takes place.

It is believed that the compounds of the invention wherein the further moiety is a readily detectable moiety may be useful in determining the metastatic state of cancer cells. This may be an important factor influencing the nature and outcome of future therapy.

A further aspect of the invention provides a kit of parts (or a therapeutic system) comprising (1) a compound of the invention wherein the further moiety is a cytotoxic moiety which is able to convert a relatively non-toxic prodrug into a cytotoxic drug and (2) a relatively non-toxic prodrug. The kit of parts may comprise any of the compounds of the invention and appropriate prodrugs as herein described.

A still further aspect of the invention provides a kit of parts (or a therapeutic system) comprising (1) a compound of the invention wherein the further moiety is able to bind selectively to a directly or indirectly cytotoxic moiety or to a readily detectable moiety and (2) any one of a directly or indirectly cytotoxic moiety or a readily detectable moiety to which the further moiety of the compound is able to bind.

For example, a kit of parts may contain an anti-hNe—Na antibody labelled with biotin and streptavidin labelled with a readily detectable label as defined above.

The invention will now be described by reference to the following, non-limiting Example and Figures.

FIG. 1: Third-order polynomial fits to the PN1 VGSCα image analysis data. Fits for the three repeats performed on the first MAT-LyLu extract are shown. PCR product mass (in nanograms) is plotted against PCR cycle number. Top inset shows the gel images from which the data was derived. Representative PCR cycle numbers for given bands are indicated above the gels.

FIG. 2: Details of the VGSCA splice variants found in the prostate cancer cells. Splice variants of (a) SCN2A, (b) SCN3A, (c) SCN8A and (d) SCN9A gene products, determined from specific PCR tests, found in rat (RB2 and PN1) and human (1B2, HB3, hNa6 and hNe—Na) cell lines, are shown. Typical SQT-PCR gel images are displayed on the left; idealised bands representing each PCR product are indicated on the side. A schematic representation of the structural features corresponding to each product is shown to the right, and product size indicated (in nucleotides). The locations of intron positions (differently shaded regions represent different exons) and PCR primer positions (arrows), in relation to the normal domain structure of the VGSCαs, are also shown. Representative PCR cycle numbers for given bands are indicated above the gels. N and A denote neonatal and adult alternatively spliced exons, respectively. Δ indicates products with both alternatively spliced exons missing.

Figure 3:
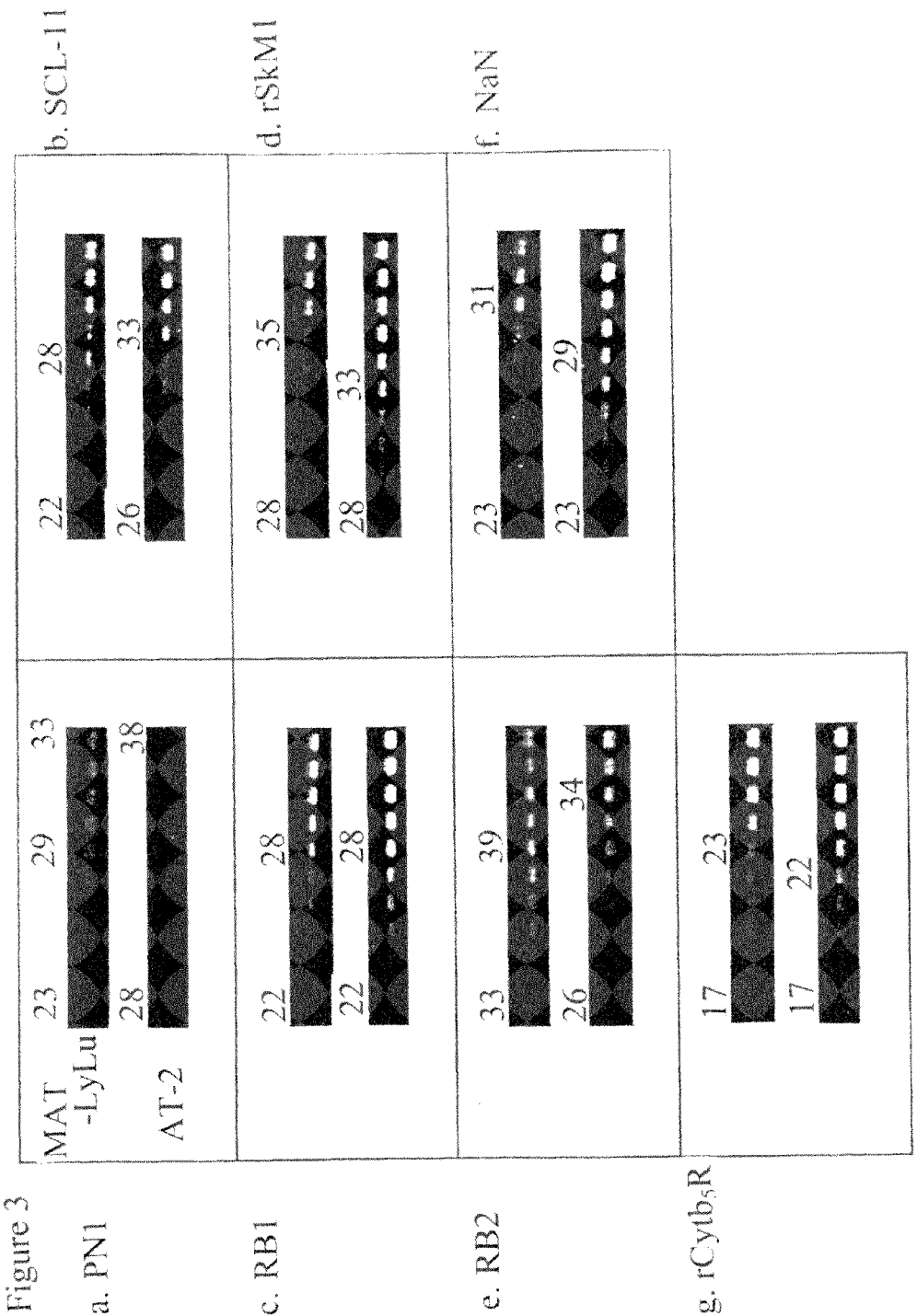

FIG. 3: SQT-PCR gel images for the rat VGSCαs. SQT-PCRs for (a) PN1, (b) SCL-11, (c) RB1, (d) rSkM1, (e) RB2 and (f) NaN/SNS2; and (g) the rCytb$_5$R control are shown. Representative PCR cycle numbers for given bands are indicated above the gels. In each panel, the top image was derived from MAT-LyLu cell extracts; the bottom image, from AT-2 extracts.

Figure 4:
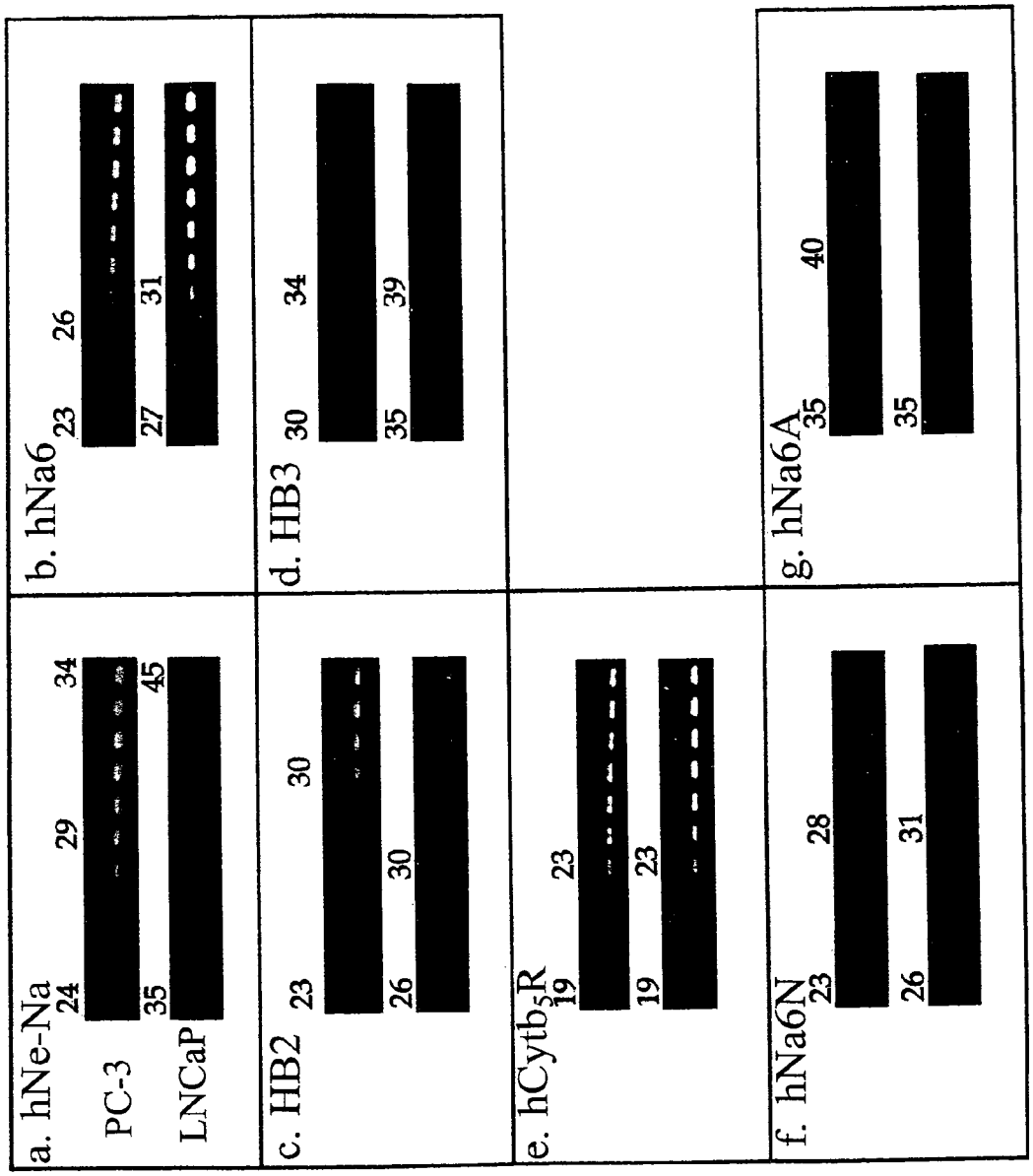

FIG. 4: SQT-PCR gel images for the human VGSCαs. SQT-PCRs for (a) hNe—Na, (b) hNa6, (c) 1HB2 and (d) HB3; and (e) the hCytb$_5$R control; and the hNa6 (f) neonatal and (g) adult splice variants are shown. Representative PCR cycle numbers for given bands are indicated above the gels. In each panel, the top image was derived from PC-3 cell extracts; the bottom image, from LNCaP cell extracts.

Figure 5:
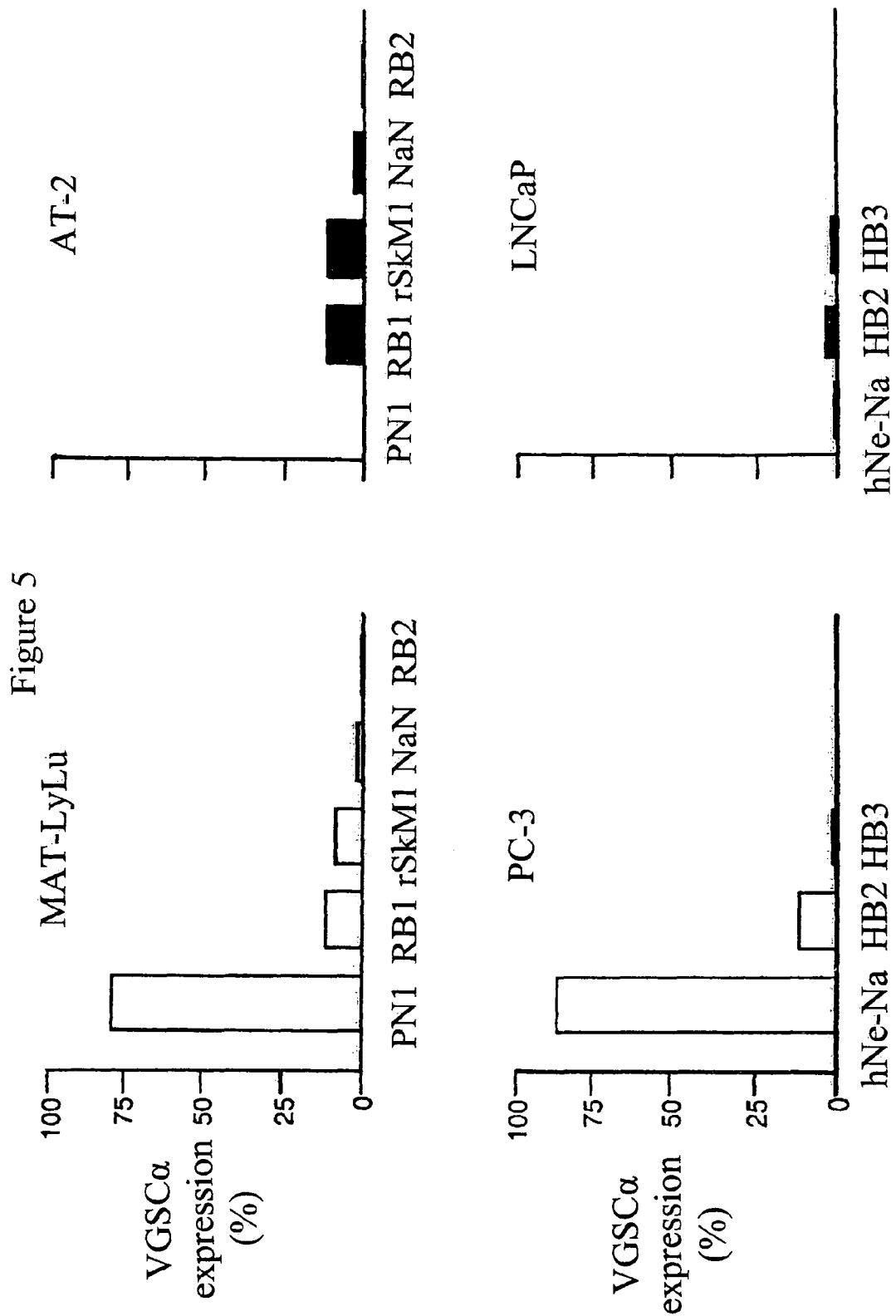

FIG. 5. Proposed expression levels of the various "functional VGSCα" mRNAs in the strongly (white bars) and weakly (black bars) metastatic prostate cancer cell lines. In each case, the vertical axis denotes the approximate level of expression with respect to functional VGSCα levels in the strongly metastatic counterpart (MAT-LyLu and PC-3 for rat and human cells, respectively). Expression levels were determined from degenerate screens using RB1 (rat) and hCytb$_5$R (human) as standards. The relative abundance of functional VGSCα mRNAs may be slightly over-estimated for VGSCαs expressed in multiple splice forms (most notably HB2, a high proportion of which is present in the ΔHB2 form).

Figure 6:
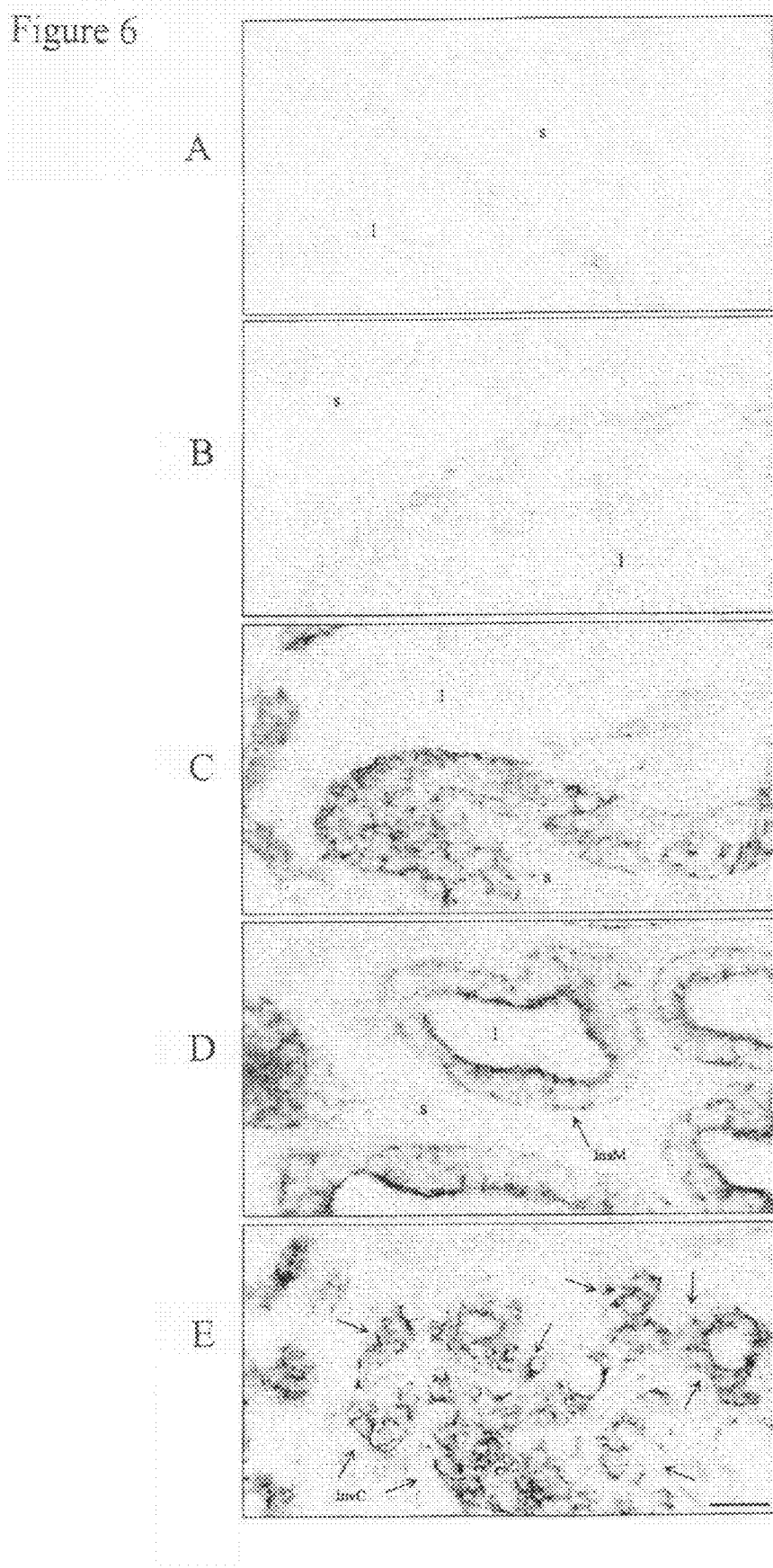

FIG. 6. Sections of human prostate at various pathological stages stained immunohistochemically with VGSC antibody. A. Benign prostatic hyperplasia. B. Low-grade PIN. l, lumen. s, stroma. C. High-grade PIN. D. In situ malignancy—InsM. E. Invasive cancer cells—InvCs (several examples indicated by the arrows are shown). Immunohistochemistry methods were applied to clinical tissues, which had been fixed in 10% formalin and embedded in paraffin. Sections from 10 different patients varying in age and Gleason grading were used. The tissues, after being treated in the microwave oven to retrieve the antigens, were incubated with a Na$^+$ channel antibody (Upstate BioTechnology Inc.) which is a peptide antibody recognising any type of vertebrate VGSC (England et al (1991) *Brain Res.* 548, 334-337). Sections were first treated with this antibody (2 μg/ml) at 4° C. overnight. For the detection of the signal, biotinylated secondary antibody, avidin-biotin complex and diaminobenzidine as the chromogen were utilised. For blocking the secondary binding sites, serum of the host of the secondary antibody was applied. Two different types of negative controls were done: (1) the primary antibody was skipped; (2) the primary antibody was pre-absorbed with the immunising peptide. In either case, no VGSC staining was seen. For quantitative analysis, the images were acquired with a 3-colour coded digital camera (Pixera Corporation, Los Gatos, Calif., USA), utilising a Nikon microscope and Apple Mac computer. Optical density measurements were made by using image analysis program (OPTIMAS, version 5.2 (Stemmer, Germany). Scale bar, 13.5 μm.

Figure 7:
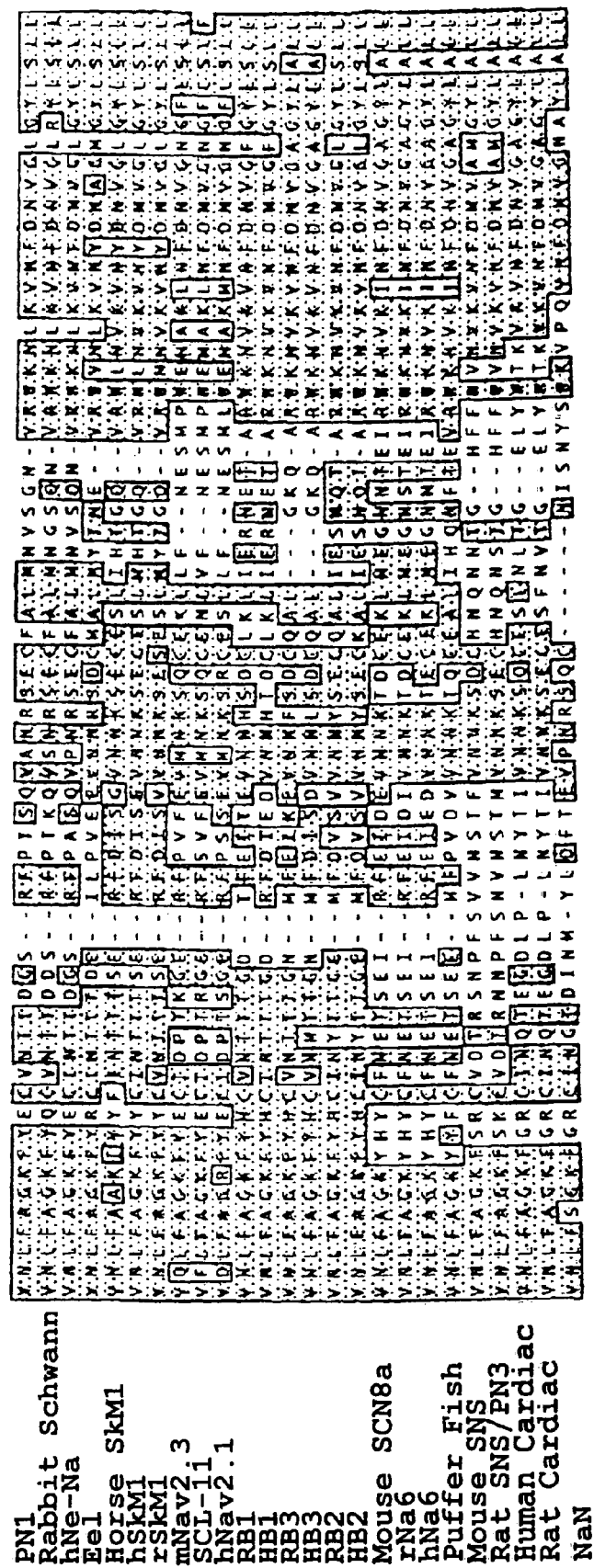

FIG. 7. Alignment of the amino acid sequences of the YJ1/YJ2C region of vertebrate VGSCαs. The alignment was generated using Lasergene's MEGALIGN software. All sequences were aligned using the Clustal method with the PAM 250 weight table. Conserved residues are boxed and shaded. Sequence accession numbers are as follows: PN1 (GB: U79568); Rabbit Schwann cell (GB: U35238); hNe—Na (PIR: S54771); Eel (GB: X01119); Horse SkM1 (GB: U25990); hSkM1 (GB: M81758); rSkM1 (GB: M26643); Mouse mNav2.3 (PIR: A55138); SCL-11 (GB: Y09164); hNav2.1 (GB: M91556); RB1 (SW: P04774); HB1 (GB: 571446); RB3 (SW: P08104); HB3 (GB: S69887); RB2 (PIR: B25019); HB2 (GB: M94055); Mouse SCN8a (GB: U26707); rNa6 (GB: L39018); Puffer Fish (GB: D37977); Mouse SNS (GB: Y09108); Rat SNS/PN3 (GB: X92184); Human Cardiac (PIR: A38195); Rat Cardiac (SW: P15389); NaN (GB: AF059030).

Figure 8:
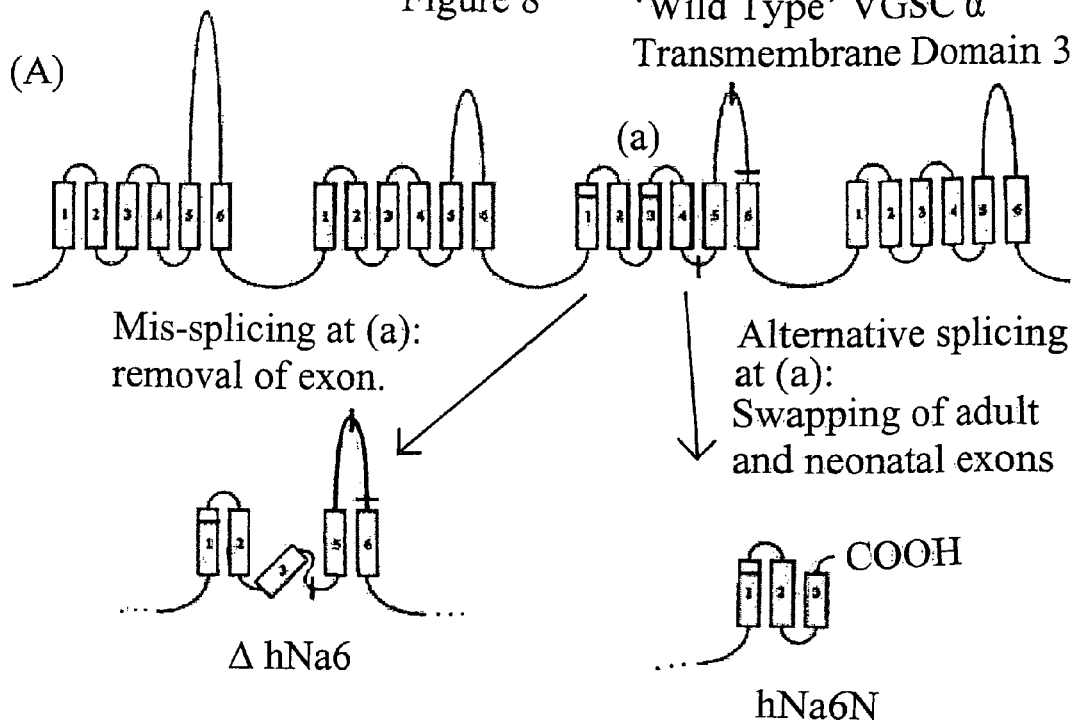
Figure 8:
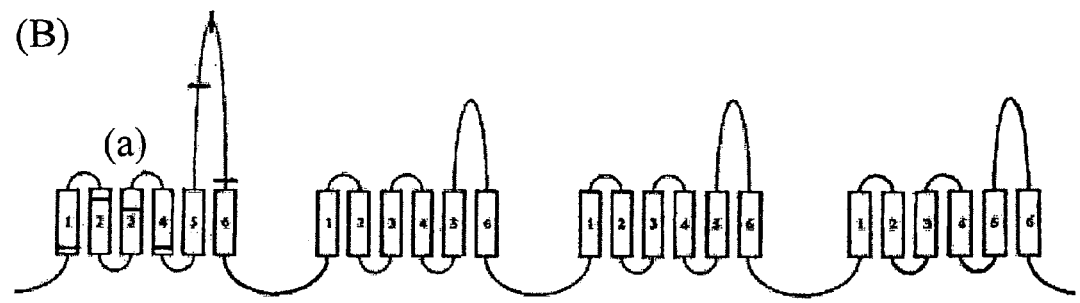

FIG. 8. Predicted topography of splice variants of (A) hNa6 and (B) PN1, hNe—Na and IIB2 expressed in the rat and human prostate cancer cell lines, as determined from specific primer PCRs. Dark bars (-) indicate conserved intron positions in VGSCα genes. Adapted from Oh & Waxman (1998).

Figure 9:
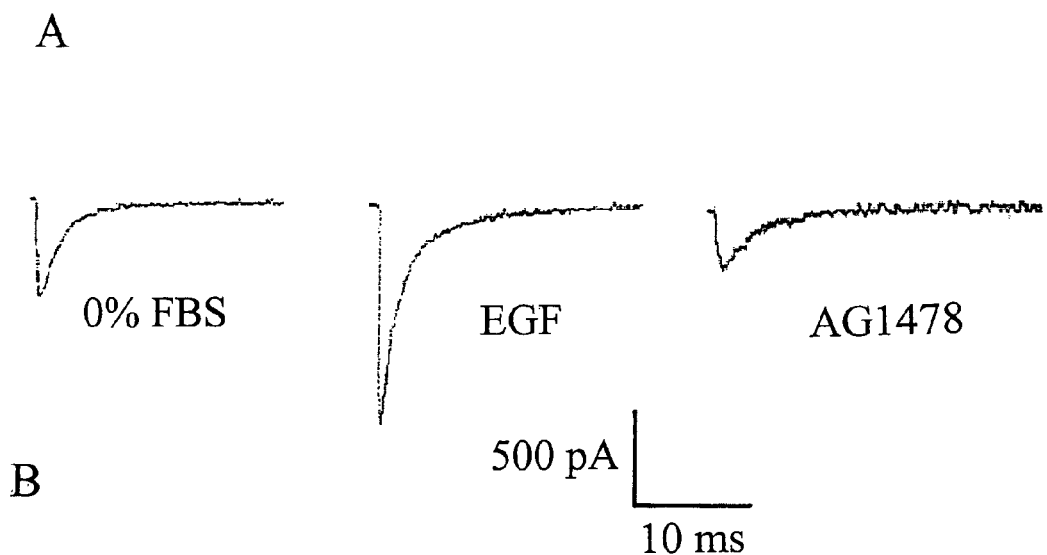
Figure 9:
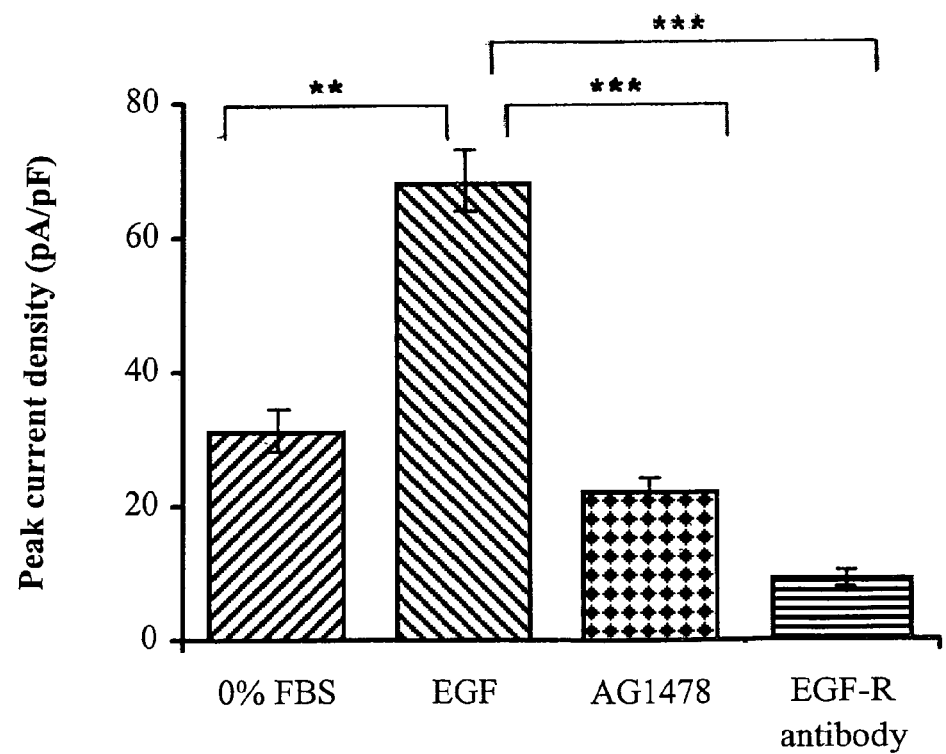

FIG. 9. (A) Current recordings from the MAT-LyLu rat prostatic cancer cell line elicited by depolarising the membrane from a holding potential of −100 mV to 0 mV following 24 h incubation in 0% FBS, 100 ng/ml EGF and 1 μM AG1478. Voltage gated Na$^+$ channel expression was upregulated in the presence of EGF. (B) Histograms showing mean peak Na$^+$ current density ± standard error following 24 h incubation in 0% FBS, 100 ng/ml EGF, 1 μM AG1478 and EGF receptor antibody (1 μg/ml). Statistical significance is indicated as =p<0.01 and *=p<0.001, respectively.

EXAMPLE 1

Expression Profiles of Voltage-Gated Na$^+$ Channel α-Subunit Genes in Rat and Human Prostate Cancer Cell Lines: Predominant Expression of PN1/hNe—Na Type Voltage-Gated Na$^+$ Channel and Subunits in Highly Metastatic Rat and Human Prostate Cancer Cell Lines Voltage-gated Na$^+$ channels (VGSCs) control a variety of cellular activities, and their dysfunction has been implicated in a number of pathophysiological conditions, including prostate cancer metastasis. Although VGSCs can occur as multiple-subunit assemblies, the α-subunits (VGSCαs) alone can encode functional channels. We have developed two new reverse transcription polymerase chain reaction (RT-PCR) methods, degenerate primer screening and a novel semi-quantitative PCR technique. These enabled a detailed qualitative and quantitative investigation of VGSCα mRNA expression in rat (MAT-LyLu/AT-2) and human (PC-3/LNCaP) prostate cancer cells of markedly different metastatic potential, and produced highly consistent results. Only the strongly metastatic cells (MAT-LyLu and PC-3) were shown previously to possess functional VGSC activity. VGSCα degenerate primer PCR screens identified eight different VGSCα genes: SCN1A-4A, SCN7A-9A and SCN11A. Specific primer PCRs demonstrated that most VGSCαs were expressed as multiple splice variants which would code for both functional and non-functional (highly truncated) proteins. Semi-quantitative PCR (SQT-PCR) results were consistent with a basal level of VGSCα mRNA expression occurring in weakly metastatic (AT-2/LNCaP) cells and this being greatly elevated in cells of stronger metastatic potential (MAT-LyLu/PC-3). The marked increase in expression of the SCN9A gene specifically (also termed PN1/hNe—Na) was largely responsible for this elevation in VGSCα mRNA levels in both rat and human cells. Thus, SCN9A is highly likely to be the main source of the functional VGSC detected.

Abbreviations: VGSCs, voltage-gated Na$^+$ channels; VGSCα, voltage-gated Na$^+$ channel α-subunit; VGSCβ, voltage-gated Na$^+$ channel β-subunit; DRG, dorsal root ganglion; RT-PCR, reverse transcription polymerase chain reaction; S, transmembrane segment; D, transmembrane domain; ID, inter-domain; TTX, tetrodotoxin; sscDNA, single-stranded cDNA; R6, random hexamer primers; nt, nucleotides; SQT-PCR, semi-quantitative polymerase chain reaction; TBE, trizma-borate-EDTA buffer; Cytb$_5$R, NADH-cytochrome b5 reductase; NGF, nerve growth factor.

Background

Voltage-gated Na$^+$ channels (VGSCs)[1] are large membrane-spanning glycoproteins composed of a large (≅240 kD), four-transmembrane domain α-subunit (VGSCα) and up to two different auxiliary β-subunits (VGSCβs) (1). Expression of the VGSCα alone is sufficient for functional channel formation (2). The VGSCβ(s) serve a number of supporting roles such as facilitating functional channel availability (3), modulating channel kinetics (4,5) and perhaps even altering pharmacological characteristics (6).

VGSCαs constitute a family of at least eleven different genes in higher vertebrates (7), denoted SCN1A to SCN11A; their products have been cloned from a variety of excitable cell types. At least two subfamilies of VGSCα genes have been described based on sequence data: Na$_v$1 and Na$_v$2 (8). Although not yet experimentally determined, it is generally held that these subfamilies represent VGSCαs with markedly different electro-physiological properties (9). In fact the lack of conservation of landmark VGSCα sequences in Na$_v$2 VGSCαs implies that they may not even be voltage-gated or Na$^+$ selective (9, 10). The existence of a third subfamily, Na$_v$3, has recently been proposed with the cloning of a cDNA (NaN/SNS2) from rat dorsal root ganglion (DRG) cells. Although NaN/SNS2 shares less than 50% sequence homology with other VGSCαs, its deduced amino acid sequence possesses all the characteristic sequences of Na$_v$1 VGSCαs (11).

By utilizing RT-PCR and in situ hybridization methods, several studies have documented the simultaneous expression of multiple VGSCαs within diverse cell types (12-14). Particular VGSCαs have been found to be expressed at different levels, with expression under dynamic control (e.g. during development or injury). For example, mRNAs for at least eight different VGSCαs were found in adult rat DRG cells, with a wide range of expression levels: RB1, Na6, NaN/SNS2 and SCL-11 mRNAs were expressed at very high levels, PN1 and SNS/PN3 at intermediate levels, and RB2 and RB3 at very low levels (11, 15, 16). Following axonal injury SNS and NaN/SNS2 mRNAs were dramatically down-regulated, whilst expression of RB1, RB2 and RB3 was up-regulated (17, 18).

VGSCα genes can occur as a number of alternatively spliced isoforms, expression of which is also under dynamic control. Alternative splicing of exons coding for the third segment (S3) of the first transmembrane domain (D1) has been found to be developmentally regulated for SCN2A and SCN3A (19, 20), yielding "neonatal" and "adult" forms. These code for proteins which differ by only one amino acid, positioned at the extreme extracellular end of S3. The effect of this change on VGSCα function is presently unclear. Similar alternatively spliced exons exist at the corresponding position in SCN8A and SCN9A (21, 22) but not in SCN4A, SCN5A, SCN10A and SCN11A (23-26). To date, no evidence of such alternative splicing has been found for SCN1A or SCN7A. Alternative splicing also occurs in other regions of the VGSCα, particularly inter-domain (ID) 1-2 and D3.

The strict regulation of multiple VGSCα gene and splice product expression within the available VGSCα mRNA pool, among different tissue types and during development or following injury (e.g. 17, 18, 27) would suggest that different VGSCα gene products and their isoforms are likely to have significantly different functional roles, which, at present, are largely unknown.

The functional roles of VGSCs are best understood in the central nervous system where VGSC activity controls not only basic impulse generation and conduction but also directional and patterned growth, including target-specific axonal migration and regional synaptic connectivity (28-30). VGSCs have also been implicated in several hereditary diseases of excitable tissues (7, 31), and in more complicated pathological disorders, including chronic pain syndromes (32), epilepsy (33), ischaemic stroke (34) and Alzheimer's disease (35). There is increasing evidence that VGSC expression is also associated with strong metastatic potential in rat (MAT-LyLu) and human (PC-3) models of prostate cancer (36-38). Indeed, expression of functional VGSCs may have a direct, positive influence upon the metastatic process. Accordingly, blockage of VGS currents in these strongly metastatic cell lines, by application of tetrodotoxin (TTX), significantly (~30%) reduced the cells' invasive potential. Electro-physiological and pharmacological properties of the current in the rat were consistent with the channels being neuronal, TTX-sensitive ($Na_v1$) type (39). SCN4A gene expression was found in both strongly and weakly metastatic cell lines of human and rat (40). However, the pharmacological properties of the VGS currents in the rat MAT-LyLu cells were not consistent with those reported for this VGSCα. This could result from (1) the numerous differences determined in the MAT-LyLu/AT-2 rSkM1 primary sequence; (2) differences in post-translational mechanisms (eg association with auxiliary subunits, level of glycosylation/phosphorylation of the channel) in these cells; or (3) the presence of other VGSCαs in the MAT-LyLu cells that produce the recorded VGS currents.

In the present study, we extend our work to determine the expression of mRNAs of other VGSCαs in the highly (MAT-LyLu and PC-3) and lowly (AT-2 and LNCaP) metastatic prostate cancer cells using a comparative, quantitative RT-PCR approach.

Experimental Procedures

Cell cultures MAT-LyLu, AT-2, LNCaP and PC-3 cell lines were cultured and harvested as described previously (36, 37).

RNA extraction This was performed as in (41) or as described below. Briefly, cells were homogenized in a solution ("A"), using an IKA homogeniser, such that 1 ml of solution was used per 0.1 g of tissue. Solution A contained 4 M guanidinium thiocyanate, 25 mM $Na^+$ citrate (pH 7.0), 0.5% sarcosyl and 0.72% (v/v) β-mercaptoethanol. The following were then added and shaken vigorously for 10 seconds: 2 M $Na^+$ acetate, pH 4.0 (10% volume of solution A), phenol (equal volume of solution A) and chloroform (20% volume of solution A). Centrifugation was performed at 10,000×g for 20 mins at 4° C. The supernatant was taken and precipitated with isopropanol. Then, the samples were centrifuged as before and the pellet was resuspended in about 30% of the initial volume of solution A. A second isopropanol precipitate was performed, the pellet was washed with 75% ethanol, and resuspended in sterile distilled water.

Three different RNA extracts were obtained from three different cell batches of each of the rat cell lines (named: MLL.1, MLL.2, MLL.3, AT.1, AT.2, AT.4) and two extracts from the two different cell batches of the human cell lines (named PC. 1, PC.2, LN.1, LN.2).

VGSCα degenerate primer screening A PCR strategy capable of amplifying all known VGSCαs was used to amplify, and subsequently identify by cloning and sequencing, all VGSCαs expressed in the prostate cancer cell lines. Specific VGSCα primers were used, following initial sequencing results, to allow rapid PCR screening of numerous VGSCα clones derived from each cell line.

Briefly, DNA was removed from the extracts by digestion with DNase I and 5 µg of the total RNA was used as the template for single-stranded cDNA (sscDNA) synthesis (Superscript II, GIBCO BRL). sscDNA synthesis was primed with a random hexamer mix (R6) in a final volume of 20 µl. VGSCα cDNA was then amplified from the R6-sscDNA pool by PCR (Taq DNA polymerase, Amersham Pharmacia) using degenerate PCR primers (YJ1 and YJ2C) used previously to amplify both $Na_v1$ and $Na_v2$ VGSCαs from adult rat retinal pigment epithelial cells (42), and novel VGSCαs from a protochordate ascidian (43). PCR reactions were performed on 4 µl of the R6-sscDNA template, using 200 µM of each dNTP, 1 unit of Taq, 1× Taq buffer and 1 µM of each primer, in a final volume of 20 µl. Amplification was via: (i) initial denaturation at 94° C. for 5 min; (ii) addition of 1 U enzyme; (iii) 33-35 cycles of denaturation at 94° C. for 1 min, annealing at 40° C. for 1 min, and elongation at 72° C. for 1 min; and (iv) elongation at 72° C. for 10 min. For this and all PCRs performed, reactions with no sscDNA added were also carried out to control for cross-contamination from other DNA sources.

PCR products were analysed by electrophoresis and gel purified prior to ligation into the pGEM-T vector (pGEM-T Easy Vector System, Promega). These were then used to transform E. coli (pMosBlue, Amersham). Plasmid DNA was recovered from bacterial cultures using a modified version of the Vistra Labstation 625 miniprep procedure (Vistra DNA Systems, Amersham). Fifty clones with "inserts" were positively selected by gel electrophoresis for each of the ten RNA extracts. Following DNA sequencing of a subset of approximately 10 clones from each screen, performed using the Amersham Thermo Sequenase fluorescent cycle sequencing kit and the Vistra DNA 725 automated sequencer (Amersham International), specific PCR primers were designed to the most abundant VGSCαs found in the screens and used in conjunction with the universal vector primers, allowing for rapid PCR screening of clones without the need for extensive sequencing. Primers corresponded to nucleotides (nt) 4118-4137, 3406-3425, 4441-4460, 4066-4085, 4139-4158, 4265-4284 and 4325-4344 for PN1 (58° C.), SCL-11 (50° C.), RB1(46° C.), rSkM1 (64° C.), hNe—Na (54° C.), HB2 (56° C.) and hNa6 (54° C.) VGSCαs, respectively (numbering according to GenBank; reaction annealing temperature used indicated in parentheses). These primers were tested on sequenced clones to confirm that they yielded only specific products. Clones that did not test positive for these VGSCαs were identified by sequencing. The percentages of clones representing a given VGSCα (out of the 50 clones in each screen) were averaged. Data are presented as means ± standard errors.

VGSCα-specific PCR tests The region between the two degenerate primers contains no conserved intron sites in studied VGSCα genes (22-25). Consequently, PCRs across conserved VGSCα gene intron sites were performed to confirm that VGSCαs found in the screens were not amplified from contaminating genomic DNA. Additionally, several VGSCαs found in the degenerate primer screens (particularly SCN2A, SCN3A, SCN8A and SCN9A) have been found to exist in numerous splice forms. Thus, specific 20-mer primers were designed to amplify products spanning conserved introns between D1:S2 to D1:S5/S6, permitting identification of the expressed splice form(s) of SCN2A (rat and human), SCN3A (human) and SCN9A (rat and human), and controlling for genomic DNA contamination. Primers for hNa6 (SCN8A) and NaN/SNS2 (SCN11A) were designed to D3, however, where similar alternative splicing to that for D1:S3 occurs in the hNa6 VGSCα (22, 44). Reactions amplified nucleotides corresponding to 424-847; 386-879; 684-1160; 632-1129; 870-1347; 3353-3674; 474-862; 3855-4370; 512-1024; 493-897, for PN1 (60° C.), SCL-11 (58° C.), RB1 (58° C.), RB2 (59° C.), rSkM1 (58° C.), NaN/SNS2 (58° C.), hNe—Na (59° C.), hNa6 (60° C.), 1B2 (58° C.) and HB3 (60° C.), respectively.

Reactions were performed as above, using 2.5 µl of the R6-sscDNA mix and 0.5 µM of each primer, cycling 30-35 times. PCRs were carried out on both strongly and weakly metastatic cell line extracts, irrespective of whether these VGSCαs had previously been found in the screens. Observed products were cloned and sequenced, and a consensus sequence for each VGSCα in each cell line then produced (using at least three clones, each derived from different RNA extracts). For RB2, HB2, HB3, PN1 and hNe—Na at least four clones derived from each cell line extract were sequenced for the PCR products of 498 nt, 513 nt, 405 nt, 424 nt and 389 nt, respectively (illustrated in FIG. 2).

Semi-Quantitative PCRs (SQT-PCRs) Eight DNased RNA extracts (two extracts for each cell line) were used to produce three sets of R6-sscDNAs for each extract. 2.4 µl of these R6-sscDNAs was used as the template for VGSCα-specific PCRs (performed as above), in a final volume of 60 µl. To allow direct comparison of results obtained from strongly and weakly metastatic cell lines, all comparable R6-sscDNA and PCR reactions were performed simultaneously.

A kinetic observation approach (45; Hoof et al (1991) *Anal. Biochem.* 196, 161-169; Wiesner et al (1992) *Biochem. Biophys. Res. Comm.* 183, 553-559) was adopted such that an aliquot of 5 µl from the 60 µl reaction was taken at the end of each amplification cycle, for eleven cycles, while reactions were held at 72° C. The amplification cycle at which aliquots were first taken differed depending on the VGSCα studied. These aliquots were then electrophoresed (0.8% agarose gels) with DNA markers of known concentration. Gels were post-stained for 15 minutes (TBE buffer containing 0.8 µg/ml ethidium bromide), and digitally imaged (GDS 7500 Advanced Gel Documentation System, Ultra-Violet Products, Cambridge, UK). Total product mass (nanograms) in each aliquot was determined by image analysis (1D Image Analysis Software, Kodak Digital Science, NY). Two characteristic stages in each PCR reaction were quantified:

(1) Threshold PCR cycle number ($CN_t$) at which a given PCR product could just be detected by the image analysis software (default settings).

(2) PCR cycle number at which the exponential phase of the reaction finished ($CN_e$).

Accumulation of reaction product with increasing PCR cycle number follows a sigmoid curve (45). However, the two extremes of this curve were unknown or undetermined for the SQT-PCR data (i.e. the initial mass of cDNA at zero cycles was unknown, and the final product mass at the end of the PCR undetermined). Thus, a sigmoid curve could not be fitted to the data. Instead a third-order polynomial equation, which also has only one possible point of inflexion (here corresponding to the end of the exponential phase of the PCR), was used to approximate a sigmoid curve. Curve-fitting was performed using STATISTICA (SoftStat Inc., Tulsa, Okla.), and the second derivative then calculated, to give $CN_e$. This procedure could be performed successfully, with the calculated values of $CN_e$ falling within the data points obtained experimentally (FIG. 1). Data are presented as means and standard errors for each cell line (three repeats on two extracts for each VGSCα). The values of $CN_t$ and $CN_e$ were used directly to compare the levels of expression of each VGSCα in the strongly and weakly metastatic cell lines.

NADH-cytochrome b5 reductase ($Cytb_5R$), which is expressed at very similar levels in normal, cancerous and strongly metastatic cells derived from numerous tissue types (46, 47), was present in both rat and human degenerate primer screens as a major constituent of the non-specific products found (the "non-VGSCα" clones). Consequently, this was used as a control amplicon in SQT-PCRs. $Cytb_5R$ 20-mer primers amplified nucleotides 385-809 and 299-790 of rat and human homologues, respectively (annealing temperature, 60° C. for both).

The specific PCRs for PN1, hNe—Na, RB2, HB2, hNa6 and HB3 produced multiple VGSCα products, due to alternative splicing, making determination of the VGSCαs' levels of expression more difficult. In order to obtain single products for these VGSCαs different PCRs were performed using new 20-mer primers which amplified nucleotides 20-345; 172-544; 5941-6308; 3827-4344; 5914-6270; 1594-1875, for PN1 (60° C.), RB2 (60° C.), hNe—Na (56° C.), hNa6 (60° C.), HB2 (58° C.) and HB3 (59° C.), respectively. hNe—Na, hNa6, HB2 and HB3 products did not span conserved intron sites so control PCR reactions were performed in which the sscDNA template was replaced by an aliquot from a reverse transcription reaction which had no reverse transcriptase added. All products were cloned and sequenced.

Two additional 20-mer primers ("neonatal": nt 500-519, GenBank numbering, and "adult": nt 3996-4015), were used to determine the relative expression levels of the neonatal and adult splice forms of hNa6 in the prostate cancer cells. Reactions were performed on only one RNA extract of the PC-3 and LNCaP cells in conjunction with the 3' hNa6-specific primer used for the VGSCα-specific PCR tests ("neonatal" annealing temperature, 58° C.; "adult" PCR, 57° C.;).

GenBank Sequence Nucleotide Numbers Nucleotide numbering was according to accession numbers U79568, Y03639, X03638, X03639, Y17153, AF059030, X82835, AB027567, AF050730, M94055, AF035685, D00636, Y09501 for PN1, SCL-11, RB1, RB2, rSkM1, NaN/SNS2, hNe—Na, hNa6, hNa6 "neonatal", HB2, HB3, $rCytb_5R$ and $hCytb_5R$, respectively.

Results

VGSCα degenerate primer screening The combined results of the PCR and sequencing screens of the minipreped clones for the different cell lines are shown in Table I. Eight different VGSCα types were found in the screens, representing products from SCN1A-4A, SCN7A-9A and SCN11A genes. Of these, six different VGSCαs were found in the rat and four in the human; the homologues of two VGSCαs found in the human screens were also present in the rat cells (PN1 derived from SCN9A, and RB2 from SCN2A). All VGSCαs found were identical to the respective published sequence in the amplified region (delineated by the degenerate primers).

TABLE I

Summary of the VGSCα degenerate primer screen results

| VGSCα | | Rat cell lines | | Human cell lines | |
|---|---|---|---|---|---|
| Gene | Gene Product | MAT-LyLu | AT-2 | PC-3 | LNCaP |
| SCN1A | RB1/HB1 | 5.3 ± 0.7 | 34.0 ± 13.3 | — | — |
| SCN2A | RB2/HB2 | — | 1.3 ± 0.7 | 11.0 ± 5.0 | 11.0 ± 7.0 |
| SCN3A | RB3/HB3 | — | — | 1.0 ± 1.0 | 1.0 ± 1.0 |
| SCN4A | rSkM1/hSkM1 | — | 34.0 ± 12.0 | — | — |
| SCN7A | SCL-11/hNa$_T$2.1 | 55.3 ± 7.3 | 10.7 ± 7.7 | — | — |
| SCN8A | rNaCh6/hNa6 | — | — | 41.0 ± 5.0 | 47.0 ± 15.0 |
| SCN9A | PN1/hNe—Na | 37.3 ± 8.7 | — | 45.0 ± 3.0 | — |
| SCN11A | NaN/— | — | 8.0 ± 2.0 | — | — |
| Non-VGSCα | | 2.0 ± 1.2 | 12.0 ± 2.0 | 2.0 ± 2.0 | 41.0 ± 7.0 |

Results are shown as the percentage of clones tested (n = 50 in each case). Each screen is the result of 2-3 extracts from each cell lines. Errors indicate standard errors. Dasshed lines (—) indicate the absence of clones with that particular VGSCα identity in the screens performed.

The degenerate primers were designed to amplify all the possible cDNA combinations which can code for two amino acid sequence motifs perfectly conserved in all thus far cloned and sequenced Na$_v$1 VGSCαs (YJ1=FWLIFSIM; YJ2C=QVATFKGW) and yield products of 225-237 bps. It was likely (at least for Na$_v$1 channels), therefore, that the proportion of clones representing each VGSCα type would approximately reflect the actual proportion of that VGSCα within the cellular VGSCα mRNA pool.

The sequence between the two highly conserved primer-binding regions is very different in all VGSCαs, allowing discrimination between VGSCα types by DNA sequenceing or by PCR (using VGSCα-specific primers which would only amplify products of one VGSCαtype).

Products of only one Na$_v$1 type VGSCα gene, SCN9A (PN1/hNe—Na), were found to be abundant in the screens of all strongly metastatic extracts (both rat- and human-derived): 37.3±8.7% and 45.0±3.0% for the MAT-LyLu and PC-3 cells, respectively. In contrast, no SCN9A gene products were found in the screens performed on the corresponding weakly metastatic cells. SCL-11 was also more frequent in the screens of the MAT-LyLu (55.3±7.3%) compared with the AT-2 cells (10.7±7.7%).

Numerous non-VGSCα clones were identified. As would be apparent to the skilled person, clones were classified as non-VGSCα if they could be matched to known GenBank DNA sequence entries not coding for VGSCαs, or if they represented previously unpublished cDNAs that did not possess sequences with conserved VGSCα sequence motifs in the degenerate primer delineated region. The percentage of clones with a non-VGSCα identity was greater in the weakly metastatic cells compared with the strongly metastatic counterpart (in both rat and human). Furthermore, the overall levels were greater in the human compared to the rat screens. hCytb$_5$R was the non-VGSCα found most often in the screens on the human cells (100% of non-VGSCα clones in PC-3 and 61% in LNCaP).

VGSCα-specific PCR tests These yielded products for all the VGSCαs found in the degenerate screens (SCN1A, SCN7A and SCN9A for MAT-LyLu-derived sscDNAs; SCN1A, SCN2A, SCN4A, SCN7A, SCN11A for AT-2-derived sscDNAs), indicating that all were indeed expressed as mRNA transcripts (and not derived from genomic DNA).

Additionally, rat VGSCαs found only in AT-2 screens were found to be expressed in the MAT-LyLu cells (RB2 (SCN2A), rSkM1 (SCN4A) and NaN(SCN11A)). VGSCαs (SCN9A) found only in the strongly metastatic cell screens (MAT-LyLu and PC-3) were expressed in some or all of the weakly metastatic cell extracts (PN1 detected in one of the three AT-2 extracts; hNe—Na in both LNCaP extracts).

Sequence analysis indicated that several splice forms of SCN2A, SCN3A, SCN8A and SCN9A were expressed in both strongly and weakly metastatic cells (FIG. 2). These splice forms consisted of both neonatal and adult forms for SCN2A, SCN3A and SCN8A but only the neonatal form for SCN9A (10 and 12 clones sequenced, respectively, for rat and human cells). Interestingly, neonatal forms were apparently more abundant than adult forms in both strongly and weakly metastatic human cell lines for SCN2A and SCN3A (8 vs 1 clone for both VGSCαs). In contrast, the adult form of SCN2A was more abundant in both MAT-LyLu and AT-2 cells (13 vs 2 clones).

Truncated splice forms (denoted Δ), missing whole exons due to the splicing out of both adult and neonatal exons from the mRNA transcript, were also amplified and sequenced from SCN2A (in the AT-2 cells), SCN8A and SCN9A (FIG. 2). ΔSCN9A was found only in the strongly metastatic cells (rat and human). Assuming the published open reading frame, the transcripts for SCN2A, SCN3A and SCN9A would code for VGSCα proteins truncated at D1:S3. In contrast, ΔhNa6 (from SCN8A) would code for a VGSCα protein only missing half of D3:S3 and all of D3:S4, as described before (48). Additionally, an RB2 (SCN2A) splice form containing both neonatal and adult exons was sequenced (from AT-2 extracts), representing a partially spliced RB2 transcript. This would translate into an RB2 protein truncated immediately after the neonatal D1:S3 (FIG. 2).

Four of the VGSCα (SCL-11, RB2, HB3 and hNa6) types differed slightly from the respective published sequences in the regions cloned. Partial sequence analysis also revealed that hNe—Na (in PC-3 and LNCaP cells) differed from the corresponding GenBank sequence in part of the 3' non-coding region. These changes are outlined in Table II. It is expected that other changes may also be present, particularly in the non-coding regions.

TABLE II

Nucleotide (nt) differences in the partially sequenced VGSCαs compared to GenBank sequences

| Nt difference | Nt position | Amino acid change | VGSCα Region | Sequence conservation |
|---|---|---|---|---|
| rSCN2A - 1 | 775 (A to G) | Asn to Asp (Asn 189) | D1:S3 | Asp in all VGSCαs |
| rSCN2A - 2 | 918 (T to C) | None (Thr 236) | D1:S4/S5 | — |
| hSCN3A-1 | 578 (T to C) | Val to Ala (Val 175) | D1:S2 | Ala in all VGSCαs |
| rSCN7A - 1 | 427 (C to T) | None (Asn 139) | D1:S1 | — |
| rSCN7A - 2 | 462 (— to T) | Cys to Leu (Cys 151) | D1:S2 | Leu in all Na$_v$2s |
| rSCN7A - 3 | 469 (A to —) | None (Gly 153) | D1:S2 | — |
| rSCN7A - 4 | 481 (C to T) | None (Phe 157) | D1:S2 | — |
| rSCN7A - 5 | 490 (G to T) | None (Leu 160) | D1:S2 | — |
| rSCN7A - 6 | 661 (C to T) | None (Ile 217) | D1:S4 | — |
| rSCN7A - 7 | 842 (G to A) | Ser to Asn (Ser 281) | D1:S5/S6 | Asn in all Na$_v$2s |
| hSCN8A-N1 | 493 (C to A) | None (after STOP) | D3:S3 | — |
| hSCN8A-N2 | 511 (N to A) | None (after STOP) | D3:S3 | — |
| hSCN9A-1 | 6230 (G to —) | None (after STOP) | — | — |
| hSCN9A-2 | 6231 (A to —) | None (after STOP) | — | — |
| hSCN9A-3 | 6232 (T to —) | None (after STOP) | — | — |
| hSCN9A-4 | 6233 (T to —) | None (after STOP) | — | — |

Deduced amino acid changes and the relative degree of conservation of changed residues in other VGSCαs are shown.

SQT-PCRs Typical electrophoresis results are illustrated in FIGS. 3 and 4 for rat and human VGSCαs, respectively. Assuming that the PCR reactions performed on strongly and weakly metastatic cell RNA extracts had similar efficiencies, differences in the calculated $CN_t$ and $CN_e$ values (derived from the gel images) reflect real differences in expression levels. Consistent with this assumption, the control amplicon (Cytb$_5$R) showed little or no difference in either rat ($CN_t$=18.3±0.2 vs. 17.3±0.4; $CN_e$=23.1±0.4 vs. 22.1±0.2) or human cell extracts ($CN_t$=19.2±0.3 vs. 19.5±0.4; $CN_e$=23.5±0.2 vs. 23.4±0.3).

Further, utilising the derived $CN_t$ and $CN^e$ values, it is possible to calculate approximate absolute differences in expression levels of the VGSCαs (assuming an 80% PCR efficiency (Bishop et al (1997) *Immunol Cell Biol* 75, 142-147)), as shown in Table III (a and b)

In MAT-LyLu versus AT-2 cells, only two VGSCαs (PN1 and SCL-11) required markedly less amplification to yield detectable products and reach $CN_e$, indicating a greater level of expression in MAT-LyLu cells. Importantly, the most striking difference was seen for PN1: $CN_t$=25.2±0.5; $CN_e$=29.2±0.4 (FIG. 3a). In fact, PN1 was never detected in the two AT-2 cell extracts extensively studied, even after 45 cycles; an apparently low level of PN1 was present in a third AT-2 extract ($CN_t$=35.7±0.3).

One other VGSCα (RB2) showed a notable cell-dependent difference in the amplification profile (FIG. 3e); however, the results indicated overall low levels of expression: $CN_t$=35.4±0.4 (MAT-LyLu) vs. 29.8±0.8 (AT-2). Minor cell-dependent differences were seen also for rSkM1 (FIG. 3d) and NaN/SNS2 (FIG. 3f), again the apparently greater level of expression occurring in the weakly metastatic cells. One VGSCα, RB1, showed no obvious difference in the expression levels between the two cell lines (FIG. 3c).

In PC-3 versus LNCaP extracts, the most striking cell-dependent difference was for hNe—Na (FIG. 4a), the orthologue of PN1: $CN_t$=25.7±0.8 (PC-3) vs. 37.7±0.3 (LNCaP). There were also differences between the expression levels of hNa6, HB2 and 1B3 across the two cell lines ($CN_t$=22.6±0.5 vs. 26.8±0.2; 26.8±0.5 vs. 30.7±0.5; 34.0±0.7 vs. 39.7±0.9, respectively), again with a greater level in the PC-3 cells, but these were much less than for hNe—Na.

The results of SQT-PCRs amplifying the neonatal (hNa6N) and adult (hNa6A) isoforms of hNa6 (FIGS. 4f and 4g) indicated that both forms were expressed at greater levels in the strongly metastatic than the weakly metastatic cells: $CN_t$=25.3±0.3 vs 28.0±0, $CN_e$=28.1±0.2 vs 31.8±0.3 for the neonatal form, and $CN_t$=36.7±0.3 vs >45.0 for the adult form, respectively. These $CN_t$ values would also suggest that the neonatal form was expressed at a much greater level than the adult form in both cell lines.

Initial SQT-PCRs for SCN2A, SCN3A, SCN8A and SCN9A that yielded multiple products are shown in FIG. 2. Therefore, the relative expression levels of scn2a, scn3a, scn8a and scn9a VGSCαs determined are comprised of different forms of these VGSCαs. Multiple product SQT-PCRs generally agreed with the results of the single-product SQT-PCRs; importantly, for example, VGSCα expression levels were greater in PC-3s than LNCaPs. The neonatal/adult isoforms consistently appeared to be the dominantly expressed splice variants of RB2, HB3, PN1 and hNe—Na, with products evident at a lower cycle number than other isoforms. For HB2, however, both the Δ and the neonatal/adult isoforms were apparently expressed at similar levels (FIG. 2a). In contrast, hNa6 expression appeared to be dominated by the neonatal form in LNCaP cells and by the neonatal and A forms in PC-3 cells (FIG. 2c).

Discussion

In this study we developed novel RT-PCR methods to investigate multiple VGSCα gene expression in prostate cancer cell lines and showed (i) that multiple VGSCαs and their splice variants were expressed in both strongly and weakly metastatic prostate cancer cell lines derived from rat and human sources; (ii) that the overall level of VGSCα expression was considerably greater in strongly metastatic compared to weakly metastatic cells; and (iii) that the expression of a particular functional VGSCα type—the product of SCN9A (PN1/hNe—Na)—was predominant, being greatly upregulated in the strongly metastatic cells of both rat and human models of prostate cancer.

The cell lines used were chosen for study due to their very different metastatic abilities. Rat AT-2 cells are weakly metastatic when inhected subcutaneously in Copenhagen rats (less than 10% of animals develop lung and lymph node metastases (Isaacs et al (1986) *Prostate* 9, 261-281); in constrast, MAT-LyLu cells are strongly metastatic (more than 80% of animals develop lung and lymph node metastases (Isaacs et al (1986)). Similarly, human PC-3 cells, when subcutaneously injected into athymic nude mice, readily metastasised, resulting in axillary lymph node metastases in 56% of animals (Shevrin et al (1989) *Prostate* 15, 187-194; Waters et al (1995) *Prostate* 26, 227-234), whereas LNCaP cells did not metastasise in athymic mice (Lee et al (1993) *Cancer Metastatsis Rev* 12, 21-28). Furthermore, upon orthotopic injection into the prostate of recipient nude mice metastatic variant PC-3 cells gave rise to lymph node metastases in 90% of animals, whilst LNCaP cells also displayed tumorigenicity but did not yield evident lymph node metastases (Stephenson et al (1992) *J Natl Cancer Inst* 84, 951-957).

Methodological aspects—The degenerate primer PCR screening technique enabled, initially, the determination of the VGSCαs expressed in these cells. Other techniques, including a degenerate PCR-restriction enzyme digest technique (Fjell, J et al (1997) *Mol. Brain. Res.* 50, 197-204), and northern blotting using common VGSCα probes (Beckh, S. (1990) *FEBS Letts.* 262, 317-322), have similarly been employed to sample VGSCα expression. However, unlike such methods, degenerate screens also yield quantitative information. Since our degenerate PCR primers were designed to two highly conserved regions of all published VGSCαs (in D3:S5 and D3:S5/S6), it is likely that all VGSCαs of the $Na_v1$ subfamily were amplified with essentially the same efficiency, ie the relative proportions of the VGSCαs in the screens broadly reflect their relative abundances in the cellular mRNA. This is supported by the SQT-PCR data, which agreed closely with the screening results, particularly when comparing estimated differences in expression levels of VGSCαs between strongly and weakly metastatic cells (Table IIIa and IIIb). Thus, although the screening and SQT-PCR results cannot directly be used to determine absolute levels of VGSCα expression, information concerning the VGSCα mRNA levels relative to each other were represented by the percentage of clones of each type in the screens.

Importantly, the most noticeable difference was for SCN9A, which was expressed at least 1000-fold higher in the strongly metastatic cells. SCN9A was also the predominant VGSCα in the strongly metastatic cell lines, representing about 80% of the "functional VGSCα" mRNA population in the MAT-LyLu and PC-3 cells.

The utility of PCR for quantitative analysis is limited by the loss of quantitation at a certain stage of amplification beyond which the reaction ceases to amplify exponentially and eventually reaches a plateau (Morrison, C. & Gannon, F. (1994) *Biochim. Biophys. Acta* 1219, 493-498). Consequently, most of the commonly used 'quantitative' PCR techniques (reviewed in Morrison & Gannon (1994)) require attention to this onset of non-exponential amplification. This point was readily determined with the novel SQT-PCR data analysis method introduced in the present study. Third-order polynomial data analysis was applied to a simple, time-saving SQT-PCR technique, based on kinetic observation, to determine the stage of the PCR (represented as the cycle number $CN_e$) at which exponential amplification ceased. $CN_e$ could then be used as a reference value for easy, direct comparison of VGSCα mRNA levels in different cell lines, in a similar manner to $CN_t$ comparisons. However, $CN_e$ is likely to be a more reliable parameter than $CN_t$ since (1) it is derived from several data points rather than the one $CN_t$ reading; and (2) it is a continuous rather than discrete value, and hence more accurate.

In conclusion, our novel degenerate screening and SQT-PCR techniques produced a consistent quantitative profile of the VGSCα expression in these cells. The level of confidence in this analysis was further strengthened by the robustness of the $Cytb_5R$ control data obtained from the different cell lines. Both methods, especially in combination, thus represent powerful new means of rapid, reliable, qualitative/quantitative analysis of VGSCα mRNA expression, particularly useful when comparing cells of different phenotype, or the same cell type under different conditions.

TABLE III

Calculated differences in the expression levels of each VGSCα between strongly and weakly metastatic (a) rat and (b) human cell lines.

a.

| VGSCa Gene | Gene Product | $CN_t$ | $CN_e$ | Screen |
|---|---|---|---|---|
| SCN1A | RB1 | −1.5 | +1.4 | std (1) |
| SCN2A | RB2 | −26.9 | −18.9 | −40 |
| SCN4A | rSkM1 | −3.1 | −3.4 | −4 |
| SCN7A | SCL-11 | +13.3 | +13.3 | +30 |
| SCN9A | PN1 | +100,000* | ND | ND |
| SCN11A | NaN | −3.2 | −2.4 | −3 |
| $rCytb_5R$ | $rCytb_5R$ | −1.8 | −1.8 | 1 | b.

| VGSCa | Gene | $CN_t$ | $CN_e$ | Screen |
|---|---|---|---|---|
| SCN2A | HB2 | +9.9 | ND | +13 |
| SCN3A | HB3 | +28.5 | ND | +13 |
| SCN8A | hNa6 | +11.8 | +18.9 | +11 |
| SCN9A | hNe-Na | +~1150 | ND | ND |
| $hCytb_5R$ | $hCytb_5R$ | +1.2 | +1.2 | std (1) |

Differences are shown for $CN_t$ values, $CN_e$ values (from SQT-PCR) and the screening data, and are stated as multiplication factors. Position and negative value indicate higher and lower expression levels, respectively, in the strongly versus weakly metastatic cells. $CN_t$ and $CN_e$ differences were calculated assuming 80% PCR efficiency in each case (similar to that reported in Bishop et al (1997) *Immunol Cell BIOI* 75, 142-147), according to the following eaquation: $1.8^{[MAT-LyLu\ value - AT-2\ value]}$ (45). Degenerate screen differences were calculated assuming an equivalent level of expression of designated standards (RB1 for the rat screens; $hCytb_5R$ for the human screens), denoted "std", in the strongly and weakly metastatic cells. "ND" indicates that the difference could not be determined.
* This was the minimum expression difference between strongly and weakly metastatic cells, determined from SQT-PCR data derived from the third AT-2 cell extract.

The screen results were consistent with the total level of VGSCα mRNAs being very different between the strongly and weakly metastatic cells. The SQT-PCR data suggested that the levels of expression of $Cytb_5R$ in cells of differing metastatic potential (both rat and human) were very similar. Accordingly, the increased incidence of this non-VGSCα clone in the degenerate screens of the weakly metastatic LNCaP and AT-2 cells (Table I) indicated a lower VGSCα target to noise ratio in these cells compared to their strongly metastatic counterpart (hence a lower level of VGSCα expression).

The results of this study show, therefore, that a basal level of VGSCα mRNA expression occurs in the weakly metastatic cells and that this is considerably upregulated in the strongly metastatic phenotype. Such a basal level of VGSCα mRNA expression in weakly metastatic cells concurs with previous flow cytometry results (38) which revealed a low level of VGSCα protein in LNCaP and AT-2 cells, despite the absence of electro-physiologically detectable VGS currents. VGSCα expression in non-cancerous prostate epithelial cells has not been investigated in this Example. Further work is required to determine whether basal VGSCα expression is associated with neoplasm or is characteristic of epithelial cells of normal prostate.

The screening and SQT-PCR results cannot directly be used to determine absolute levels of VGSCα expression. However, degenerate screen PCRs would amplify all VGSCαs of a given subfamily (e.g. $Na_v1s$) with approximately the same PCR efficiency, thus retaining information of the levels of expression of the VGSCαs relative to each other in the cellular mRNA. Thus, it should be possible to compare relative abundances of these in the screens and relate these abundances to relative proportions of particular VGSCαs in the cells' mRNA. The available data are consistent with the relative expression profiles of VGSCαs shown in FIG. 5. In this estimation, the SCN9A gene products represent some 80% of the "functional VGSCα" mRNA population in the MAT-LyLu and PC-3 cells. Multiplicity of VGSCα expression Although the level of expression of VGSCα mRNA was much higher in the strongly metastatic MAT-LyLu cells, and most VGSCα types were expressed at greater levels in strongly vs weakly metastatic cells, three lowly expressed VGSCα genes (SCN2A, SCN4A and SCN11A) were found to be present at slightly higher levels in the weakly metastatic AT-2 cells. This strongly indicates that these VGSCαs do not normally contribute to the VGS currents detected in the MAT-LyLu cells but the physiological significance, if any, and the mechanism(s) controlling this down-regulation of expression have yet to be determined. In contrast, in the human cell lines, all VGSCαs detected were expressed at higher levels in the strongly metastatic PC-3 cells.

Multiple VGSCα expression has previously been demonstrated in adult rat DRG cells (14), PC12 cells (49) and cultured spinal cord astrocytes (12). The prostate cancer epithelial cell lines studied here represent yet another cell type in which simultaneous expression of multiple VGSCαs has been shown to occur. In most of these instances, a wide range of VGSCα mRNA expression levels were found to exist within the cells. At present, the functional consequence(s) of this multiple expression within a single cell type is unclear. VGSCα expression in these cells may be dramatically and quickly up- or down-regulated in response to numerous stimuli, such as growth factors and axotomy (14, 17, 49), in a subtype-specific manner. This would strongly imply that different VGSCαs posess different functions, the relative importance of which can change quickly under different conditions. Fine-tuning of expression may occur rapidly in order to match the VGSCα expression profile of the cell to the required functional response. It is highly likely that such changes in the functional VGSC profile can only be achieved by the regulation of different VGSCαs already being expressed and not by the slower process of "switching on" VGSCα genes. Thus, multiple, low level VGSCα expression could enable cells to meet functional requirements necessitated by dynamic changes in their micro-environment.

VGSCs have been detected in numerous "non-excitable" tissues, including epithelial types such as retinal pigment, lens and corneal epithelium, where their functional role is mostly unknown (42, 50, 51). A functional role for VGSCs that does not involve the production of action potentials has been determined in spinal cord astrocytes in vitro (52). In these cells, VGSCs instead provide a return pathway for $Na^+$, maintaining $Na^+/K^+$-ATPase activity. Other roles for VGSCs in non-excitable cells may include the production of graded potentials involved in intercellular $Ca^{2+}$ homeostasis or activation of various intracellular signalling pathways (52).

High expression levels of "non-functional VGSCαs" in prostate cancer cells The ability of the SCN7A and SCN8A mRNA transcripts found in the MAT-LyLu and PC-3 cells to create functional VGSCs is doubtful. SCN7A codes for an $Na_x2$ VGSCα with no proven channel-forming capability. Although the SCN8A gene is known to be able to produce functional VGSC proteins, whether the specific SCN8A gene products expressed in the human prostate cancer cells can function as viable channels in these cells is questionable. hNa6N codes for a highly truncated VGSCα protein possessing only D1 and D2 (44). This variant was found in non-neuronal and neonate tissues and proposed to be incapable of forming functional VGSCs, acting instead as a "fail-safe" mechanism to prevent the synthesis of full-length, adult hNa6 VGSCα protein (44). Indeed, a highly truncated voltage-gated $K^+$ channel α-subunit has been successfully used to artificially suppress endogenous $K^+$ currents in rat anterior pituitary cells (53). The adult isoform of hNa6 was also found to be expressed in both strongly and weakly metastatic human cells at a very low level, but it is likely that the presence of the neonatal isoform prevents hNa6A functional expression. The ΔhNa6 variant, which has effectively lost the voltage-sensing S4 segment in D3, is similar to the ΔhNe—Na, ΔPN1, ΔHB2 and ΔRB2 splice forms found in the specific PCR tests. These transcripts are likely to represent mis-spliced, non-viable forms of SCN8A, SCN9A and SCN2A VGSCα genes (48). The occurrence of apparently non-functional VGSCαs could be an additional means of regulating effective VGSC expression in the prostate cancer cells.

Predominant expression of PN1/hNe—Na in strongly metastatic cells The results of the degenerate screens and the SQT-PCR demonstrated consistently that PN1/hNe—Na was the predominant VGSCα expressed in the strongly metastatic cells. Furthermore, sequence data indicated that most of the SCN9A transcripts were in the neonatal form. In fact, the adult splice form has only been found to date at very low levels in neonate rabbit Schwann cells (21), so it is presently unclear whether the D1:S3 alternative splicing of the SCN9A gene is developmentally regulated. It may be notable that all of the VGSCαs found to be alternatively spliced at D1:S3 in the prostate cancer cells, except for RB2, were also mainly expressed in the neonatal form.

The present study provides an example of the expression of the SCN9A gene in carcinoma, indicating that up-regulation of SCN9A gene expression could be a common carcinoma-associated phenomenon. hNe—Na was originally cloned and sequenced from the clonal C-cell line of a human medullary thyroid carcinoma (hMTC cells) and found to be expressed in human C-cell carcinoma tissue (54). The PN1 clone was obtained from $PCl_2$ cells, derived from a pheochromocytoma of the rat adrenal medulla (49). There is no suggestion of a link between hNe—Na or PN1 expression and carcinoma in these studies.

SCN9A products were previously found at high levels in the peripheral nervous system and at much lower levels in brain, spinal cord, Schwann cells, heart, and adrenal and thyroid glands (49, 54-56), particularly in neuroendocrine cells (54, 55). Neuroendocrine cells are also present in the prostate. Recent studies suggest that their proliferation and differentiation may predict prostate cancer progression (Cohen et al (1994) *Cancer* 74, 1899-1903; Anthony di Sant'Agnese, P. (1998) *Prostate Suppl.* 8, 74-79; Bonkhoff, H. (1998) *Prostate Suppl.* 8, 18-22). Prostatic neuroendocrine cells lack detectable nuclear androgen receptors (Bonkhoff, H et al (1993) *Virchows Arch. A. Pathol. Anat.* 423, 291-294; Krijnen, J et al (1993) *Histochemistry* 100, 393-398), suggesting that they are androgen-insensitive. This neuroendocrine insensitivity may play a role in the mechanisms responsible for the progression of prostatic adenocarcinomas to androgen insensitivity. Intriguingly, androgens can inhibit the activity of VGSCs (Tabb, J. S et al (1994) *J. Neurosci.* 14, 763-773) and may also decrease VGSCα mRNA expression as other steroid hormones have been found to do (Rich, M. M., Kraner, S. D. and Barchi, R. L. (1999) Neurobiol. Dis. 6, 515-522). Thus, it may be that a high level of VGSCα mRNA expression occurs in prostatic epithelial cells with the change to androgen-insensitivity.

Where comparisons can be made, the electro-physiological and pharmacological characteristics of PN1 and hNe—Na type VGSCs are very similar to those of the VGS currents observed in the strongly metastatic rat and human prostate cancer cells, (36, 37, 39, 49, 54, 56). This is consistent with the SCN9A products specifically being the source of the VGS currents recorded in these cells. Since this VGSCα has been shown to potentiate the invasion process (36-38), it may be expected to have a particular subcellular distribution pattern, interaction with the cytoskeleton and/or specialised electrophysiological properties which facilitate this activity. Indeed, a recent electro-physiological study has highlighted one apparently unique property of hNe—Na, a very slow rate of closed-state inactivation. This permits the production of "ramp currents" in response to slow but gradually increasing sub-threshold stimuli (Cummins et al (1998) *J. Neurosci.* 18, 9607-9619); VGSCαs with faster closed-state inactivation rates are incapable of responding to such stimuli.

PN1 protein also has a specific subcellular localization in nerve growth factor (NGF)-differentiated PC12 cells and cultured rat DRG neurons, being present specifically in neurite terminals and at the leading edges of growth cones (49). NGF upregulates PN1 expression in PC12 cells and this is followed by morphological differentiation from a round to a highly branched shape, indicating a role for this VGSCα in enhancing cellular morphology (57). Consistent with this, TTX treatment had the opposite effect on the morphology of the MAT-LyLu cells, causing them to retract their processes and become compact (58).

Determination of SCN9A gene products specifically as the origin of VGSC functional expression in strongly metastatic prostate cancer cells, in both rat and human models of the disease, now permits the use of more specific experiments to further elucidate all aspects of the metastatic mechanism: (1) elements up-stream of the SCN9A gene, which effect the increase in expression of this gene specifically, for example hormones, growth factors and transcription factors/repressors; (2) down-stream elements which allow SCN9A expression to potentiate invasion/metastasis.

Possible expression of other VGSC subunits in prostate cancer cells The present study only attempted to characterise VGSCα mRNA expression in the strongly and weakly metastatic cells, since VGSCαs alone are sufficient to encode functional VGSCs. The multiplicity of VGSC expression determined for the prostate cells may be further complicated by the possible expression at even lower levels of transcripts of other VGSCαs and by the expression of VGSCβs. SCN1A, SCN2A, SCN3A, SCN4A and SCN8A gene products have been found to commonly associate with one or more VGSCβs and so it is likely that some VGSCβ expression occurs in these cells. However, SCN9A gene products do not appear to associate with VGSCβs (54, 55), so it is unlikely that these auxiliary subunits would make a significant contribution to the mechanism(s) responsible for the high level of functional VGSC expression in the metastatic cells.

It is not certain that all the VGSCA genes found to be expressed in these cells are actually translated into proteins. If all expressed VGSCα genes can potentially be translated, such multiplicity in cells could enable rapid upregulation or downregulation of VGSCαs (potentially faster than "switching on" transcription of VGSCα genes), in a subtype-specific manner, in cells' response to various stimuli, such as growth factors and damage (Fjell et al (1999) *Molec Brain Res* 67, 267-282; Dib-Hajj et al (1996) *PNAS* 93, 14950-14954; Toledo-Aral et al (1997) *PNAS* 94, 1527-1532). This would imply that different VGSCαs subserve different functions, the relative importance of which can quickly change under diverse conditions. Thus, multiple, low level VGSCα expression could enable cells to meet functional requirements necessitated by dynamic changes in their microenvironment.

Concluding Remarks

The present study has two broad implications. First, the characterisation of the functionally distinct prostatic epithelial cells' VGSCα mRNA expression profiles now establishes these cells as a convenient model in which to study the patterns, regulation and functional consequences of (i) VGSC expression in non-excitable cells and (ii) the emerging concept of the multiplicity of VGSC expression, i.e. the expression of multiple VGSC subunits and multiple splice forms of these subunits in a single cell type. Second, as regards prostate cancer itself, a serious limitation in the current management methods is that the available markers for the metastatic phenotype (such as prostate specific antigen) are not reliable (59, 60). Thus, clinically important cancers cannot readily be distinguished from those which are clinically unimportant and do not require aggressive treatment (which is associated with high patient morbidity). The identification of SCN9A gene products as the predominant VGSCαs in both rat and human models of prostate cancer highlights the conservation of VGSCα expression in strongly metastatic prostate cancer cell lines. Consequently, the present study further supports the potential value of these ion channels in the possible diagnosis and therapy of the disease.

References
1. Catterall, W. A. (1986) Ann. Rev. Biochem. 55, 953-985
2. Goldin, A. L et al (1986). *Proc. Natl. Acad. Sci. USA* 83, 7503-7507
3. Isom, L. L., et al (1995) Cell 83, 433-442
4. Isom, L. L., et al (1992) Science 256, 839-842
5. Cannon, S. C., et al (1993) Pflugers Arch. 423, 155-157
6. Bonhaus, D. W., et al (1996) Neuropharmacol. 35, 605-613
7. Plummer, N. W. and Meisler, M. H. (1998) Genomics 57, 323-331
8. George, A. L., et al (1992) Proc. Natl. Acad. Sci. USA 89, 4893-4897
9. Akopian, A. N., et al (1997) FEBS Letts. 400, 183-187
10. Schlief, T., et al (1996) Eur. Biophys. J. 25, 75-91
11. Dib-Hajj, S. D, et al (1998) Proc. Natl. Acad. Sci. USA 95, 8963-8968
12. Black, J. A., et al (1994) Mol. Brain. Res. 23, 235-245
13. Dib-Hajj, S. D., et al (1996) FEBS Letts. 384, 78-82
14. Fjell, J., et al (1999) Mol. Brain. Res. 67, 267-282
15. Black, J. A., et al (1996) Molec. Brain Res. 43, 117-131
16. Sangameswaren, L., et al (1997) J. Biol. Chem. 272, 14805-14809
17. Dib-Hajj, S., et al (1996) Proc. Natl. Acad. Sci. USA 93, 14950-14954
18. Dib-Hajj, S. D., et al (1998) J. Neurophysiology 79, 2668-2676
19. Sarao, R., et al (1991) Nucleic Acids Res. 19, 5673-5679
20. Gustafson, T. A., et al (1993) J. Biol. Chem. 268, 18648-18653
21. Belcher, S. M et al (1995) Proc. Natl. Acad. Sci. USA 92, 11034-11038
22. Plummer, N. W., et al (1998) Genomics 54, 287-296
23. George, A. L., et al (1993) Genomics 15, 598-606
24. Wang, D. W., et al (1996) Biophys. J. 70, 238-245
25. Souslova, V. A., et al (1997) Genomics 41, 201-209
26. Dib-Hajj, S. D., et al (1999) Genomics 59, 309-318
27. Kallen, R. G., et al (1990) Neuron 4, 233-242
28. Catalano, S. M. and Shatz, C. J. (1998) Science 281, 559-562
29. Penn, A. A., et al (1998) Science 279, 2108-2112
30. Shatz, C. J. (1990) Neuron 5, 745-756
31. Zhou, J. and Hoffman, E. P. (1994) J. Biol. Chem. 269, 18563-18571.

32. Tanaka, M., et al (1998) NeuroReport 9, 967-972
33. Bartolomei, F., et al (1997) J. Neurocytol. 26, 667-678
34. Skaper, S. D., et al (1998) FASEB J. 12, 725-731
35. Kanazirska, M., et al (1997) Biochem. Biophys. Res. Comm. 232, 84-87
36. Grimes, J. A., et al (1995) FEBS Letts. 369, 290-294
37. Laniado, M., et al (1997) Am. J. Pathol. 150, 1213-1221
38. Smith, P., et al (1998) FEBS Letts 423, 19-24
39. Grimes, J. A. and Djamgoz, M. B. A. (1998) J. Cell. Physiol. 175, 50-58
40. Diss, J. K. J., et al (1998) FEBS Letts 427, 5-10
41. Chomczynski, P. and Sacchi, N. (1987) Ann. Biochem. 162, 156-159
42. Dawes, H., et al (1995) Vis. Neurosci. 12, 1001-1005
43. Okamura, Y., et al (1994) Neuron 13, 937-948
44. Plummer, N. W., et al (1997) J. Biol. Chem. 272, 24008-24015
45. Kohler, T. (1995). *Quantitation of mRNA by Polymerase Chain Reaction*, pp 3-14, eds. Kohler, T., Lassner, D., Rost, A.-K., Thamm, B., Pustowoit, B. and Remke, H. (Springer, Heidelberg).
46. Fitzsimmons, S. A., et al (1996) J. Natl. Cancer Inst. 88, 259-269
47. Marin, A., et al (1997) Br. J. Cancer 76, 923-929
48. Oh, Y. and Waxman, S. G. (1998) NeuroReport 9, 1267-1272
49. Toledo-Aral, J. J., et al (1997) Proc. Natl. Acad. Sci. USA 94, 1527-1532
50. Watsky, M. A., et al (1991) Pflugers Arch. 419, 454-459
51. Cooper, K., et al (1990) J. Memb. Biol. 117, 285-298
52. Sontheimer, H., et al (1994) J. Neurosci. 14, 2464-2475
53. Tu, L. W., et al (1995) Biophys. J. 68, 147-156
54. Klugbauer, N., et al (1995) EMBO J. 14, 1084-1090
55. Sangameswaren, L., et al (1996) J. Biol. Chem. 272, 14805-14809
56. Safo, P., et al (1998) Soc. Neurosci. Abstr. 24, 1324
57. Greene, L. A. and Tischler, A. S. (1976) Proc. Natl. Acad. Sci. USA 73, 2424-2428
58. Fraser, S. P., et al (1999) Cell Tissue Res. 295, 505-512
59. Mandelson, M. T., et al (1995) Ann. Rev. Public Health 16, 283-306
60. Chan, E. C. and Sulmasy, D. P. (1998) Am. J. Med. 105, 266-274

TABLE 1

PCR primers used in degenerate VGSCα primer screening of rat and human prostate cancer cell lines.

Degenerate VGSCα Primers

SEQ ID No 4  YJ1   -5' GCGAAGCTT(C/T)TGG(C/T)T IATITT(C/T)I(A/C/G/T)IAT(A/T/C)ATGGG 3'
SEQ ID No 5  YJ2C  -5' ATAGGATCCAICCI(A/C/G/T)I(A/G)AAIGC(A/C/G/T)AC(C/T)TG 3'

YJ1/YJ2C Specific Primers

SEQ ID No 6   MPN1   -5' ACGTTAGTGGAAATGTGCGA 3'  (Tm = 58° C.)
SEQ ID No 7   MSCL1  -5' ATTTAATGAATCAATGCCAT 3'  (Tm = 50° C.)
SEQ ID No 8   MhNe   -5' ATGTTAGTCAAAATGTGCGA 3'  (Tm = 54° C.)
SEQ ID No 9   MHB2   -5' ATTGCTCTCAATGAGAGCTT 3'  (Tm = 56° C.)
SEQ ID No 10  MRB1   -5' ATTTCTTTCTATTAGTTTTA 3'  (Tm = 46° C.)
SEQ ID No 11  NA29   -5' TGTATACAGGCCAGGTCCGC 3'  (Tm = 64° C.)
SEQ ID No 12  MHS6   -5' AACAATACAGAGATCAGATG 3'  (Tm = 54° C.)

Specific Primer PCR Tests

SEQ ID No 13  HNE1  -5' TATGACCATGAATAACCCGC 3'  (474-493)
SEQ ID No 14  HNE3  -5' TCAGGTTTCCCATGAACAGC 3'  (843-862)
SEQ ID No 15  2HB1  -5' TGTGCAGGATTCTTACCAAC 3'  (512-531)
SEQ ID No 16  2HB3  -5' AAGTAGTACCATTCCCATCC 3'  (1005-1024)
SEQ ID No 17  1RB   -5' ATGACAATGAGTAACCCTCC 3'  (684-703)
SEQ ID No 18  3RB   -5' TGTGCCGTTGTAATCCGTAG 3'  (1141-1160)
SEQ ID No 19  SC1   -5' ATTAGTGTTCTCACCGACAG 3'  (386-405)
SEQ ID No 27  SC3   -5' AGAATATGGTACTGGCTTCC 3'  (860-879)
SEQ ID No 28  R2A   -5' CCAACTGTGTGTTTATGACC 3'  (632-651)
SEQ ID No 29  R2C   -5' AGGCAGTACCATTCGAATGC 3'  (1110-1129)
SEQ ID No 20  SPN1  -5' TTCATGACCTTGAGCAACCC 3'  (424-443)
SEQ ID No 21  SPN4  -5' GAGTCCCATGATGCTGCTCC 3'  (1355-1374)
SEQ ID No 22  NAN1  -5' GTATCTCTGTCCATTCAGTC 3'  (423-442)
SEQ ID No 23  NAN2  -5' GAACAGCTGCTGACCGACCA 3'  (849-868)
SEQ ID No 24  H3A   -5' TTGAGCAACCCTCCTGACTG 3'  (493-512)
SEQ ID No 25  H3C   -5' GGGCCACTGCAAACATTTAT 3'  (878-897)
SEQ ID No 26  H6A   -5' TT(T/C)GA(A/G)GA(T/C)AT(A/T/C)TA(C/T)AT(A/T/C)GA 3'
SEQ ID No 30  H6B   -5' CATCTGATCTGTGTATTGTT 3'
SEQ ID No 31  H6C   -5' TGTCAAAGTTGATCTTGACG 3'
SEQ ID No 32  NA7   -5' CTGAGGACCTTCCGTGTGCT 3'  (632-651)
SEQ ID No 33  NA19  -5' TGCACACTTGTACCACCACG 3'  (1599-1618)

Primer annealing temperatures and primer annealing positions on published sequences are indicated in brackets.
Sequence accession numbers are: hNe-Na (X82835), HB2 (M94055), HB3 (AF035685), RB1 (X03638), RB2 (X03639), SCL-11 (Y09164), PN1 (U79568), rSkM1 (Y171S3), NaN (AF059030).

EXAMPLE 2

Design of Antisense Oligonucleotides for Suppressing VGSC Expression in Human Prostate Cancer 1. Alignment of all currently known VGSC types to identify potential sites for VGSC subtype-specific antisense oligonucleotide design.

```
SEQ ID No 34  Cons            agtgagtgtgaaagtcttatggag
                              agcaacaaaactg---tccgatgg
                              aaa SEQ ID No 35  hNav2.1         agtcggtgtgaaagccttctgt--
                              -ttaacgaatcca---tgctatgg
                              gaa SEQ ID No 36  hNe-Na          tccgaatgttttgcccttatgaAT
                              GTTAGTCAAAATG---TGCGAtgg
                              aaa SEQ ID No 37  Human brain 1   actgattgcctaaaactaatagaa
                              agaaatgagactg---ctcgatgg
                              aaa SEQ ID No 38  Human brain 2   agtgagtgcaAAGCTCTCATTGAG
                              AGCAATcaaactg---ccaggtgg
                              aaa SEQ ID No 39  Human brain 3   agtgactgtc--aggctcttggca
                              agcaa-------g---ctcggtgg
                              aaa SEQ ID No 40  Na6 (human)     actgaatgtgaaaagcttatggag
                              gggAACAATACAGAGATCAGATGg
                              aag SEQ ID No 41  hSkM1           aacaagtctgagtgcgagagCCTC
                              ATGCACACAGGCCAGGtccgctgg
                              ctc SEQ ID No 42  Human heart 1   aacaagagccagtgtgagtccttg
                              aacttgaccggagaattgtactgg
                              acc SEQ ID No 43  PN3/SNS (rat)   aacaagtccgagtgtcacaatcaa
                              aacagcaccggccacttcttctgg
                              gtc
```

In the above alignment the human VGSC equivalent has been used where possible. The alignment has been optimised by the introduction of sequence gaps indicated by a dash although gaps are not actually present in the real sequence or any oligonucleotide design. The most commonly occurring nucleotides are indicated in the consensus line (Cons). Potential sites for the design of 20mer antisense oligonucleotides are in bold case and underlined in the four human VGSC types that have been found in both the degenerate screens and specific PCR tests on the PC-3 and LNCaP cell lines. The most unconserved region of the fragment produced by the degenerate screen has been used to produce this line-up.

It would also be possible to design 20mer antisense oligos in the ¾ cytoplasmic linker (where VGSC sequence is highly conserved across all types) that are individually capable of 'silencing' simultaneously a number of VGSC types. For example, below the same 20 nucleotide sections of the ¾ linker from three VGSC types are shown aligned. In this section, the hNe—Na and the human brain 2 sequences are identical and the hSkM1 sequence differs at only two nucleotide positions. Therefore, in this region it is possible to design two antisense oligonucleotides that will knock-out at least three of the channels (possibly four when the Na6 (human) sequence has been confirmed for this region).

```
SEQ ID No 44  hNe-Naq         TTATGACAGAAGAACAGAAG

SEQ ID No 45  Human brain 2   TTATGACAGAAGAACAGAAG

SEQ ID No 46  hSkM1           TTATGACgGAgGAACAGAAG
```

TABLE 2

VGSCα degenerate primer screen results for (a) the rat-derived MAT-LyLu and AT-2, and (b) the human-derived PC-3 and LNCaP cell lines, expressed as percentage of clines tested.

(a)

| VGSCα Gene | Gene Product | MLL (1) n = 50 | MLL (2) n = 50 | MLL (3) n = 50 | AT-2 (1) n = 50 | AT-2 (3) n = 50 | AT-2 (4) n = 50 |
|---|---|---|---|---|---|---|---|
| SCN1A | RB 1 | 6 | 6 | 4 | 12 | 58 | 32 |
| SCN2A | RB 2 | 0 | 0 | 0 | 2 | 2 | 0 |
| SCN4A | rSkM 1 | 0 | 0 | 0 | 58 | 22 | 22 |
| SCN7A | SCL-11 | 70 | 48 | 48 | 2 | 4 | 26 |
| SCN9A | PN 1 | 20 | 44 | 48 | 0 | 0 | 0 |
| SCN11A | NaN | 0 | 0 | 0 | 12 | 6 | 6 |
| Non VGSCα | Identified | 4 | 2 | 0 | 4 | 2 | 12 |
| Non VGSCα | Unknown | 0 | 0 | 0 | 10 | 6 | 2 |

(b)

| VGSCα Gene | Gene Product | PC-3 (1) n = 50 | PC-3 (2) n = 50 | LNCaP (1) n = 50 | LNCaP (2) n = 50 |
|---|---|---|---|---|---|
| SCN2A | HB 2 | 6 | 6 | 4 | 18 |
| SCN3A | HB 3 | 0 | 2 | 0 | 2 |
| SCN8A | hNa6 | 46 | 50 | 62 | 32 |
| SCN9A | hNe-Na | 48 | 30 | 0 | 0 |
| Non VGSCα | Identified | 0 | 12 | 22 | 40 |
| Non CGSCα | Unknown | 0 | 0 | 12 | 8 |

TABLE 3

VGSCα splice variants found in the highly and lowly metastatic prostate cancer cell lines to date. Where adult and neonatal forms of the VGSCα type have been described, the form found in the prostate cancer cells is specified.

| VGSCα Type | Highly metastatic cells | Lowly metastatic cells |
|---|---|---|
| PN1 | Full-length | To be determined |
| SCL-11 | Full-length | To be determined |
| RB1 | Adult | Adult |
| RB2 | To be determined | To be determined |
| rSkM1 | Full-length | Full-length |
| NaN | To be determined | To be determined |
| hNe—Na | Full-length ΔhNe—Na Neonatal | Full-length |
| hNa6 | ΔnHa6 Full-length | ΔnHa6 Full-length |
| HB2 | ΔHB2 | ΔHB2 |
| HB3 | Neonatal | Adult |

Δ denotes splice variants with missing exons coding for the S4 segment of D1 or D3 (see section 4.3).

EXAMPLE 3

Voltage-gated Na+ Channel Expression Correlates with Pathological Progression in Human Prostate Cancer Previous electrophysiological studies have shown that functional voltage gated Na+ channels (VGSCs) are expressed selectively by highly metastatic cell lines of rat (MAT-LyLu) and human (PC-3) prostate cancer. Furthermore, blockage of these channels with tetrodotoxin significantly reduced the cells' invasion in vitro (Grimes et al. (1995) *FEBS Letts.* 369, 290-294; Laniado et al (1997) *Am. J. Pathol.* 150 1213-1221. Direct, positive correlation between invasiveness and Na+ channel protein expression by several different rat and human prostate cancer cell lines was subsequently demonstrated by Smith et al. (1998) *FEBS Lens.* 423, 19-24. However, it is not known whether VGSC expression occurs in human prostate cancer in vivo, and if so, whether the levels of expression relate to the metastatic profile of the constituent malignant epithelial cells.

Immunohistochemical localization of VGSC protein in tissue-sections of human prostate containing epithelial ducts of varying metastatic character, including in situ and invasive cancer cells, is illustrated in FIG. 6. A strong incremental increase in the intensity of staining was observed as the pathological character of the epithelial cells progressed from normal towards invasive neoplasia (FIG. 6A to E). In benign prostatic hyperplasia (BPH), the level of VGSC expression by constituent epithelial cells was very low and predominantly restricted to basal cells (FIG. 6A). In low-grade prostate intraepithelial neoplasia (low-grade PIN), the overall level of expression was increased with immunohistochemical staining of basal cells appearing slightly more intense (FIG. 6B).

For both BPH and low-grade PIN taken together, the apical:basal optical density ratio was 0.74±0.05 (n=450 ducts; 30 sections; 10 patients). A marked, step-wise increase in VGSC expression was associated with appearance of high-grade PIN recognised by the characteristic architecture and cytological features of multilayering, severe dyskaryosis and nucleolar enlargement (FIG. 6C). This trend was maintained both in ducts and acini containing in situ malignancy (InsM) where basal cells were absent (FIG. 6D), as well as in invasive cancer (InvC) cells (FIG. 6E). VGSC expression was prominent along the apical plasma membranes of luminal epithelial cells at the InsM stage (FIG. 6D). In InvC, staining was also intense along the plasma membranes of the cells (FIG. 6E). For high-grade PIN and InsM epithelial cells taken together, the apical:basal optical density ratio of VGSC staining was 1.57±0.19 (n=750 ducts; 30 sections; 10 patients). This ratio was significantly higher when compared to that for low-grade PIN ducts (P<0.01).

In conclusion, the enhanced level of VGSC expression we have previously identified as being associated with the metastatic phenotype of prostate cancer cells in vitro now has been confirmed to occur in vivo. Thus, it would appear that upregulation of functional VGSC expression occurs as an integral component of increased metastatic potential. VGSC activity could contribute to metastasis by enhancing cellular process extension (Fraser et al (1999) *Cell Tissue Res.* 295. 505-512), motility (Fraser et al (1998) *J. Physiol.* 513.P, 131P), invasiveness (Grimes et al, 1995; Laniado et al, 1997; Smith et al, 1998) or intracellular homeostasis (Foster et al (1999) *Br. J. Urol.* 83, 171-194). The cytological polarity of VGSC upregulation (apical vs. basal) could, in turn, enable directional invasion of adjacent tissues. The present observations translate fundamental information obtained previously in model systems of clonally-derived cell lines in vitro to unselected and non-clonal primary human tissues. These results suggest that VGSC expression might be a phenotypic requirement of metastatic prostate cancer cells and hence represent a valuable novel marker to identify potentially metastatic disease at the time of primary tissue diagnosis.

EXAMPLE 4

Regulation of VGSC Function in Prostate Cancer Cell Lines VGSC Functional Expression in Rodent MAT-LyLu Cells was Investigated Epidermal growth factor (EGF) upregulates VGSC functional expression. As shown in FIG. 9, exogenous EGF potentiates the functional VGSC expression. This effect is blocked by co-application of EGF receptor kinase inhibitor (AG1478; Calbiochem, San Diego, Calif., USA). Application of EGF receptor antibody (Oncogene, Cambridge, Mass., USA) also reduces the basal VGSC current implying that the phenomenon occurs endogenously.

Other growth factors (for example nerve growth factor) and hormones (including androgens) may have similar effects.

SEQUENCE LISTING

<160> NUMBER OF SEQ ID NOS: 71

<210> SEQ ID NO 1
<211> LENGTH: 15
<212> TYPE: PRT
<213> ORGANISM: Artificial Sequence

```
<220> FEATURE:
<223> OTHER INFORMATION: Description of Artificial Sequence: Designed
      peptide based on residues 446-460 of Homo sapiens hNe-Na

<400> SEQUENCE: 1

Glu Tyr Thr Ser Ile Arg Arg Ser Arg Ile Met Gly Leu Ser Glu
  1               5                  10                  15

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Designed
      peptide motif YJ1 based on Homo sapiens Nav1 VGSC?s

<400> SEQUENCE: 2

Phe Trp Leu Ile Phe Ser Ile Met
  1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Designed
      peptide motif YJ2C based on Homo sapiens Nav1 VGSC?s

<400> SEQUENCE: 3

Gln Val Ala Thr Phe Lys Gly Trp
  1               5

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Design

```
<221> NAME/KEY: modified_base
<222> LOCATION: (11)..(11)
<223> OTHER INFORMATION: n is inosine
<220> FEATURE:
<221> NAME/KEY: modified_base
<222> LOCATION: (14)..(14)
<223> OTHER INFORMATION: n is inosine
<220> FEATURE:
<221> NAME/KEY: misc_feature
<222> LOCATION: (15)..(15)
<223> OTHER INFORMATION: n is a or g or c or t.
<220> FEATURE:
<221> NAME/KEY: modified_base
<222> LOCATION: (16)..(16)
<223> OTHER INFORMATION: n is inosine
<220> FEATURE:
<221> NAME/KEY: modified_base
<222> LOCATION: (20)..(20)
<223> OTHER INFORMATION: n is inosine
<220> FEATURE:
<221> NAME/KEY: misc_feature
<222> LOCATION: (23)..(23)
<223> OTHER INFORMATION: n is a or g or c or t.

<400> SEQUENCE: 5
ataggatcca nccnnnraan gcnacytg                                      28

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Designed
      primer MPN1 based on Homo sapiens VGSC?

<400> SEQUENCE: 6
acgttagtgg aaatgtgcga                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Designed
      primer MSCL1 based on Homo sapiens VGSC?

<400> SEQUENCE: 7
atttaatgaa tcaatgccat                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Designed
      primer MhNe based on Homo sapiens VGSC?

<400> SEQUENCE: 8
atgttagtca aaatgtgcga                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Designed
      primer MHB2 based on Homo sapiens VGSC?

<400> SEQUENCE: 9
attgctctca atgagagctt                                               20
```

-continued

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Designed
      primer MRB1 based on Homo sapiens VGSC?

<400> SEQUENCE: 10
atttctttct attagtttta                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Designed
      primer NA29 based on Homo sapiens VGSC?

<400> SEQUENCE: 11
tgtatacagg ccaggtccgc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Designed
      primer MHS6 based on Homo sapiens VGSC?

<400> SEQUENCE: 12
aacaatacag agatcagatg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Designed
      primer HNE1 based on Homo sapiens VGSC?

<400> SEQUENCE: 13
tatgaccatg aataacccgc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Designed
      primer HNE3 based on Homo sapiens VGSC?

<400> SEQUENCE: 14
tcaggtttcc catgaacagc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Designed
      primer 2HB1 based on Homo sapiens VGSC?

<400> SEQUENCE: 15
tgtgcacgat tcttaccaac                                              20

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Designed
      primer 2HB3 based on Homo sapiens VGSC?

<400> SEQUENCE: 16
aagtagtacc attcccatcc                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Designed
      primer 1RB based on Homo sapiens VGSC?

<400> SEQUENCE: 17
atgacaatga gtaaccctcc                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Designed
      primer 3RB based on Homo sapiens VGSC?

<400> SEQUENCE: 18
tgtgccgttg taatccgtag                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Designed
      primer SC1 based on Homo sapiens VGSC?

<400> SEQUENCE: 19
attagtgttc tcaccgacag                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Designed
      primer SPN1 based on Homo sapiens VGSC?

<400> SEQUENCE: 20
ttcatgacct tgagcaaccc                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Designed
      primer SPN4 based on Homo sapiens VGSC?

<400> SEQUENCE: 21
gagtcccatg atcctgctcc                                                    20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Designed
      primer NAN1 based on Homo sapiens VGSC?

<400> SEQUENCE: 22
gtatctctgt ccattcagtc                                          20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Designed
      primer NAN2 based on Homo sapiens VGSC?

<400> SEQUENCE: 23
gaacagctgc tgaccgacca                                          20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Designed
      primer H3A based on Homo sapiens VGSC?

<400> SEQUENCE: 24
ttgagcaacc ctcctgactg                                          20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Designed
      primer H3C based on Homo sapiens VGSC?

<400> SEQUENCE: 25
gggccactgc aaacatttat                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Designed
      primer H6A based on Homo sapiens VGSC?

<400> SEQUENCE: 26
ttygargaya thtayathga                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Designed
      primer SC3 based on Homo sapiens VGSC?

<400> SEQUENCE: 27
agaatatggt actggcttcc                                          20

<210> SEQ ID NO 28

```
<211> LENGTH: 20
<212> TYPE: DNA
<213> ORGANISM: Artificial Sequence
<220> FEATURE:
<223> OTHER INFORMATION: Description of Artificial Sequence: Designed
      primer R2A based on Homo sapiens VGSC?

<400> SEQUENCE: 28
ccaactgtgt gtttatgacc                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Designed
      primer R2C based on Homo sapiens VGSC?

<400> SEQUENCE: 29
aggcagtacc attccaatcc                                            20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Designed
      primer H6B based on Homo sapiens VGSC?

<400> SEQUENCE: 30
catctgatct ctgtattgtt                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Designed
      primer H6C based on Homo sapiens VGSC?

<400> SEQUENCE: 31
tgtcaaagtt gatcttcacg                                            20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Designed
      primer NA7 based on Homo sapiens VGSC?

<400> SEQUENCE: 32
ctgaggacct tccgtgtgct                                            20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Designed
      primer NA19 based on Homo sapiens VGSC?

<400> SEQUENCE: 33
tgcacacttg taccaccacg                                            20

<210> SEQ ID NO 34
<211> LENGTH: 48
```

```
<212> TYPE: DNA
<213> ORGANISM: Homo sapiens

<400> SEQUENCE: 34
agtgagtgtg aaagtcttat ggagagcaac aaaactgtcc gatggaaa                48

<210> SEQ ID NO 35
<211> LENGTH: 45
<212> TYPE: DNA
<213> ORGANISM: Homo sapiens

<400> SEQUENCE: 35
agtcggtgtg aaagccttct gtttaacgaa tccatgctat gggaa                   45

<210> SEQ ID NO 36
<211> LENGTH: 48
<212> TYPE: DNA
<213> ORGANISM: Homo sapiens

<400> SEQUENCE: 36
tccgaatgtt ttgcccttat gaatgttagt caaaatgtgc gatggaaa                48

<210> SEQ ID NO 37
<211> LENGTH: 48
<212> TYPE: DNA
<213> ORGANISM: Homo sapiens

<400> SEQUENCE: 37
actgattgcc taaaactaat agaaagaaat gagactgctc gatggaaa                48

<210> SEQ ID NO 38
<211> LENGTH: 48
<212> TYPE: DNA
<213> ORGANISM: Homo sapiens

<400> SEQUENCE: 38
agtgagtgca aagctctcat tgagagcaat caaactgcca ggtggaaa                48

<210> SEQ ID NO 39
<211> LENGTH: 39
<212> TYPE: DNA
<213> ORGANISM: Homo sapiens

<400> SEQUENCE: 39
agtgactgtc aggctcttgg caagcaagct cggtggaaa                          39

<210> SEQ ID NO 40
<211> LENGTH: 51
<212> TYPE: DNA
<213> ORGANISM: Homo sapiens

<400> SEQUENCE: 40
actgaatgtg aaaagcttat ggaggggaac aatacagaga tcagatggaa g            51

<210> SEQ ID NO 41
<211> LENGTH: 51
<212> TYPE: DNA
<213> ORGANISM: Homo sapiens

<400> SEQUENCE: 41
aacaagtctg agtgcgagag cctcatgcac acaggccagg tccgctggct c            51

<210> SEQ ID NO 42
```

```
<211> LENGTH: 51
<212> TYPE: DNA
<213> ORGANISM: Homo sapiens

<400> SEQUENCE: 42
aacaagagcc agtgtgagtc cttgaacttg accggagaat tgtactggac c            51

<210> SEQ ID NO 43
<211> LENGTH: 51
<212> TYPE: DNA
<213> ORGANISM: Rattus norvegicus

<400> SEQUENCE: 43
aacaagtccg agtgtcacaa tcaaaacagc accggccact tcttctgggt c            51

<210> SEQ ID NO 44
<211> LENGTH: 20
<212> TYPE: DNA
<213> ORGANISM: Homo sapiens

<400> SEQUENCE: 44
ttatgacaga agaacagaag                                               20

<210> SEQ ID NO 45
<211> LENGTH: 20
<212> TYPE: DNA
<213> ORGANISM: Homo sapiens

<400> SEQUENCE: 45
ttatgacaga agaacagaag                                               20

<210> SEQ ID NO 46
<211> LENGTH: 20
<212> TYPE: DNA
<213> ORGANISM: Homo sapiens

<400> SEQUENCE: 46
ttatgacgga ggaacagaag                                               20

<210> SEQ ID NO 47
<211> LENGTH: 61
<212> TYPE: PRT
<213> ORGANISM: Rattus norvegicus

<400> SEQUENCE: 47

Val Asn Leu Phe Ala Gly Lys Phe Tyr Glu Cys Val Asn Thr Thr Asp
 1               5                  10                  15

Gly Ser Arg Phe Pro Thr Ser Gln Val Ala Asn Arg Ser Glu Cys Phe
            20                  25                  30

Ala Leu Met Asn Val Ser Gly Asn Val Arg Trp Lys Asn Leu Lys Val
        35                  40                  45

Asn Phe Asp Asn Val Gly Leu Gly Tyr Leu Ser Leu Leu
    50                  55                  60

<210> SEQ ID NO 48
<211> LENGTH: 61
<212> TYPE: PRT
<213> ORGANISM: Oryctolagus cuniculus

<400> SEQUENCE: 48

Val Asn Leu Phe Ala Gly Lys Phe Tyr Gln Cys Val Asn Thr Thr Asp
 1               5                  10                  15
```

Asp Ser Arg Phe Pro Thr Lys Gln Val Ser Asn Arg Ser Glu Cys Phe
            20                  25                  30

Ala Leu Met Asn Gly Ser Gln Asn Val Arg Trp Lys Asn Leu Lys Val
            35                  40                  45

Asn Phe Asp Asn Val Gly Leu Arg Tyr Leu Ser Leu Leu
            50                  55                  60

<210> SEQ ID NO 49
<211> LENGTH: 61
<212> TYPE: PRT
<213> ORGANISM: Homo sapiens

<400> SEQUENCE: 49

Val Asn Leu Phe Ala Gly Lys Phe Tyr Glu Cys Ile Asn Thr Thr Asp
 1               5                  10                  15

Gly Ser Arg Phe Pro Ala Ser Gln Val Pro Asn Arg Ser Glu Cys Phe
            20                  25                  30

Ala Leu Met Asn Val Ser Gln Asn Val Arg Trp Lys Asn Leu Lys Val
            35                  40                  45

Asn Phe Asp Asn Val Gly Leu Gly Tyr Leu Ser Leu Leu
            50                  55                  60

<210> SEQ ID NO 50
<211> LENGTH: 60
<212> TYPE: PRT
<213> ORGANISM: Electrophorus electricus

<400> SEQUENCE: 50

Val Asn Leu Phe Ala Gly Lys Phe Tyr Arg Cys Ile Asn Thr Thr Thr
 1               5                  10                  15

Asp Glu Ile Leu Pro Val Glu Glu Val Asn Asn Arg Ser Asp Cys Met
            20                  25                  30

Ala Leu Met Tyr Thr Asn Glu Val Arg Trp Val Asn Leu Lys Val Asn
            35                  40                  45

Tyr Asp Asn Ala Gly Met Gly Tyr Leu Ser Leu Leu
            50                  55                  60

<210> SEQ ID NO 51
<211> LENGTH: 60
<212> TYPE: PRT
<213> ORGANISM: Equus caballus

<400> SEQUENCE: 51

Val Asn Leu Phe Ala Ala Lys Ile Tyr Tyr Phe Ile Asn Thr Thr Thr
 1               5                  10                  15

Ser Glu Arg Phe Asp Ile Ser Gly Val Asn Asn Lys Ser Glu Cys Glu
            20                  25                  30

Ser Leu Ile His Thr Gly Gln Val Arg Trp Leu Asn Val Lys Val Asn
            35                  40                  45

Tyr Asp Asn Val Gly Leu Gly Tyr Leu Ser Leu Leu
            50                  55                  60

<210> SEQ ID NO 52
<211> LENGTH: 60
<212> TYPE: PRT
<213> ORGANISM: Homo sapiens

<400> SEQUENCE: 52

Val Asn Leu Phe Ala Gly Lys Phe Tyr Cys Ile Asn Thr Thr Thr
 1               5                  10                  15

-continued

```
Ser Glu Arg Phe Asp Ile Ser Glu Val Asn Asn Lys Ser Glu Cys Glu
            20                  25                  30

Ser Leu Asn His Thr Gly Gln Val Arg Trp Leu Asn Val Lys Val Asn
        35                  40                  45

Tyr Asp Asn Val Gly Leu Gly Tyr Leu Ser Leu Leu
    50                  55                  60

<210> SEQ ID NO 53
<211> LENGTH: 60
<212> TYPE: PRT
<213> ORGANISM: Rattus norvegicus

<400> SEQUENCE: 53

Val Asn Leu Phe Ala Gly Lys Phe Tyr Tyr Cys Val Asn Thr Thr Thr
1               5                   10                  15

Ser Glu Arg Phe Asp Ile Ser Val Val Asn Asn Lys Ser Glu Ser Glu
            20                  25                  30

Ser Leu Met Tyr Thr Gly Gln Val Arg Trp Met Asn Val Lys Val Asn
        35                  40                  45

Tyr Asp Asn Val Gly Leu Gly Tyr Leu Ser Leu Leu
    50                  55                  60

<210> SEQ ID NO 54
<211> LENGTH: 60
<212> TYPE: PRT
<213> ORGANISM: Mus musculus

<400> SEQUENCE: 54

Val Gln Leu Phe Ala Gly Lys Phe Tyr Glu Cys Ile Asp Pro Thr Lys
1               5                   10                  15

Gly Glu Arg Phe Pro Val Phe Glu Val Met Asn Lys Ser Gln Cys Glu
            20                  25                  30

Lys Leu Leu Phe Asn Glu Ser Met Pro Trp Glu Asn Ala Lys Leu Asn
        35                  40                  45

Phe Asp Asn Val Gly Asn Gly Phe Leu Ser Leu Leu
    50                  55                  60

<210> SEQ ID NO 55
<211> LENGTH: 60
<212> TYPE: PRT
<213> ORGANISM: Rattus norvegicus

<400> SEQUENCE: 55

Val Phe Leu Phe Ala Gly Lys Phe Tyr Glu Cys Thr Asp Pro Thr Arg
1               5                   10                  15

Gly Glu Arg Phe Ser Val Phe Glu Val Met Asn Lys Ser Gln Cys Glu
            20                  25                  30

Asn Leu Val Phe Asn Glu Ser Met Pro Trp Glu Asn Ala Lys Leu Asn
        35                  40                  45

Phe Asp Asn Val Gly Asn Gly Phe Leu Ser Leu Phe
    50                  55                  60

<210> SEQ ID NO 56
<211> LENGTH: 60
<212> TYPE: PRT
<213> ORGANISM: Homo sapiens

<400> SEQUENCE: 56

Val Asp Leu Phe Ala Gly Arg Phe Tyr Glu Cys Ile Asp Pro Thr Ser
```

```
                1               5                  10                  15
Gly Glu Arg Phe Pro Ser Ser Glu Val Met Asn Lys Ser Arg Cys Glu
                       20                  25                  30

Ser Leu Leu Phe Asn Glu Ser Met Leu Trp Glu Asn Ala Lys Met Asn
            35                  40                  45

Phe Asp Asn Val Gly Asn Gly Phe Leu Ser Leu Leu
        50                  55                  60

<210> SEQ ID NO 57
<211> LENGTH: 61
<212> TYPE: PRT
<213> ORGANISM: Rattus norvegicus

<400> SEQUENCE: 57

Val Asn Leu Phe Ala Gly Lys Phe Tyr His Cys Val Asn Thr Thr Thr
  1               5                  10                  15

Gly Asp Thr Phe Glu Ile Thr Glu Val Asn Asn His Ser Asp Cys Leu
                       20                  25                  30

Lys Leu Ile Glu Arg Asn Glu Thr Ala Arg Trp Lys Asn Val Lys Val
            35                  40                  45

Asn Phe Asp Asn Val Gly Phe Gly Tyr Leu Ser Leu Leu
        50                  55                  60

<210> SEQ ID NO 58
<211> LENGTH: 61
<212> TYPE: PRT
<213> ORGANISM: Homo sapiens

<400> SEQUENCE: 58

Val Asn Leu Phe Ala Gly Lys Phe Tyr His Cys Ile Asn Thr Thr Thr
  1               5                  10                  15

Gly Asp Arg Phe Asp Ile Glu Asp Val Asn Asn His Thr Asp Cys Leu
                       20                  25                  30

Lys Leu Ile Glu Arg Asn Glu Thr Ala Arg Trp Lys Asn Val Lys Val
            35                  40                  45

Asn Phe Asp Asn Val Gly Phe Gly Tyr Leu Ser Leu Leu
        50                  55                  60

<210> SEQ ID NO 59
<211> LENGTH: 58
<212> TYPE: PRT
<213> ORGANISM: Rattus norvegicus

<400> SEQUENCE: 59

Val Asn Leu Phe Ala Gly Lys Phe Tyr His Cys Val Asn Thr Thr Thr
  1               5                  10                  15

Gly Asn Met Phe Glu Ile Lys Glu Val Asn Asn Phe Ser Asp Cys Gln
                       20                  25                  30

Ala Leu Gly Lys Gln Ala Arg Trp Lys Asn Val Lys Val Asn Phe Asp
            35                  40                  45

Asn Val Gly Ala Gly Tyr Leu Ala Leu Leu
        50                  55

<210> SEQ ID NO 60
<211> LENGTH: 58
<212> TYPE: PRT
<213> ORGANISM: Homo sapiens

<400> SEQUENCE: 60
```

```
Val Asn Leu Phe Ala Gly Lys Phe Tyr His Cys Val Asn Met Thr Thr
 1               5                  10                  15

Gly Asn Met Phe Asp Ile Ser Asp Val Asn Asn Leu Ser Asp Cys Gln
             20                  25                  30

Ala Leu Gly Lys Gln Ala Arg Trp Lys Asn Val Lys Val Asn Phe Asp
         35                  40                  45

Asn Val Gly Ala Gly Tyr Leu Ala Leu Leu
     50                  55
```

<210> SEQ ID NO 61
<211> LENGTH: 61
<212> TYPE: PRT
<213> ORGANISM: Rattus norvegicus

<400> SEQUENCE: 61

```
Val Asn Leu Phe Ala Gly Lys Phe Tyr His Cys Ile Asn Tyr Thr Thr
 1               5                  10                  15

Gly Glu Met Phe Asp Val Ser Val Val Asn Asn Tyr Ser Glu Cys Gln
             20                  25                  30

Ala Leu Ile Glu Ser Asn Gln Thr Ala Arg Trp Lys Asn Val Lys Val
         35                  40                  45

Asn Phe Asp Asn Val Gly Leu Gly Tyr Leu Ser Leu Leu
     50                  55                  60
```

<210> SEQ ID NO 62
<211> LENGTH: 61
<212> TYPE: PRT
<213> ORGANISM: Homo sapiens

<400> SEQUENCE: 62

```
Val Asn Leu Phe Ala Gly Lys Phe Tyr His Cys Ile Asn Tyr Thr Thr
 1               5                  10                  15

Gly Glu Met Phe Asp Val Ser Val Val Asn Asn Tyr Ser Glu Cys Lys
             20                  25                  30

Ala Leu Ile Glu Ser Asn Gln Thr Ala Arg Trp Lys Asn Val Lys Val
         35                  40                  45

Asn Phe Asp Asn Val Gly Leu Gly Tyr Leu Ser Leu Leu
     50                  55                  60
```

<210> SEQ ID NO 63
<211> LENGTH: 62
<212> TYPE: PRT
<213> ORGANISM: Mus musculus

<400> SEQUENCE: 63

```
Val Asn Leu Phe Ala Gly Lys Tyr His Tyr Cys Phe Asn Glu Tyr Ser
 1               5                  10                  15

Glu Ile Arg Phe Glu Ile Asp Glu Val Asn Asn Lys Thr Asp Cys Glu
             20                  25                  30

Lys Leu Met Glu Gly Asn Asn Thr Glu Ile Arg Trp Lys Asn Val Lys
         35                  40                  45

Ile Asn Phe Asp Asn Val Gly Ala Gly Tyr Leu Ala Leu Leu
     50                  55                  60
```

<210> SEQ ID NO 64
<211> LENGTH: 62
<212> TYPE: PRT
<213> ORGANISM: Rattus norvegicus

<400> SEQUENCE: 64

Val Asn Leu Phe Ala Gly Lys Tyr His Tyr Cys Phe Asn Glu Thr Ser
1               5                   10                  15

Glu Ile Arg Phe Glu Ile Asp Ile Val Asn Asn Lys Thr Asp Cys Glu
            20                  25                  30

Lys Leu Met Glu Gly Asn Ser Thr Glu Ile Arg Trp Lys Asn Val Lys
        35                  40                  45

Ile Asn Phe Asp Asn Val Gly Ala Gly Tyr Leu Ala Leu Leu
    50                  55                  60

<210> SEQ ID NO 65
<211> LENGTH: 62
<212> TYPE: PRT
<213> ORGANISM: Homo sapiens

<400> SEQUENCE: 65

Val Asn Leu Phe Ala Gly Lys Tyr His Tyr Cys Phe Asn Glu Thr Ser
1               5                   10                  15

Glu Ile Arg Phe Glu Ile Glu Asp Val Asn Asn Lys Thr Glu Cys Glu
            20                  25                  30

Lys Leu Met Glu Gly Asn Asn Thr Glu Ile Arg Trp Lys Asn Val Lys
        35                  40                  45

Ile Asn Phe Asp Asn Val Gly Ala Gly Tyr Leu Ala Leu Leu
    50                  55                  60

<210> SEQ ID NO 66
<211> LENGTH: 62
<212> TYPE: PRT
<213> ORGANISM: Fugu rubripes

<400> SEQUENCE: 66

Val Asn Leu Phe Ala Gly Lys Tyr Tyr Phe Cys Phe Asn Glu Thr Ser
1               5                   10                  15

Glu Glu Met Phe Pro Val Asp Val Val Asn Asn Lys Thr Gln Cys Glu
            20                  25                  30

Ala Leu Ile His Gln Asn Phe Thr Glu Val Arg Trp Lys Asn Val Lys
        35                  40                  45

Ile Asn Phe Asp Asn Val Gly Ala Gly Tyr Leu Ala Leu Leu
    50                  55                  60

<210> SEQ ID NO 67
<211> LENGTH: 62
<212> TYPE: PRT
<213> ORGANISM: Mus musculus

<400> SEQUENCE: 67

Val Asn Leu Phe Ala Gly Lys Phe Ser Arg Cys Val Asp Thr Arg Ser
1               5                   10                  15

Asn Pro Phe Ser Val Val Asn Ser Thr Phe Val Asn Asn Lys Ser Asp
            20                  25                  30

Cys His Asn Gln Asn Asn Thr Gly His Phe Phe Trp Val Asn Val Lys
        35                  40                  45

Val Asn Phe Asp Asn Val Ala Met Gly Tyr Leu Ala Leu Leu
    50                  55                  60

<210> SEQ ID NO 68
<211> LENGTH: 62
<212> TYPE: PRT
<213> ORGANISM: Rattus norvegicus -continued

<400> SEQUENCE: 68

Val Asn Leu Phe Ala Gly Lys Phe Ser Lys Cys Val Asp Thr Arg Asn
1               5                   10                  15

Asn Pro Phe Ser Asn Val Asn Ser Thr Met Val Asn Asn Lys Ser Glu
                20                  25                  30

Cys His Asn Gln Asn Ser Thr Gly His Phe Phe Trp Val Asn Val Lys
            35                  40                  45

Val Asn Phe Asp Asn Val Ala Met Gly Tyr Leu Ala Leu Leu
        50                  55                  60

<210> SEQ ID NO 69
<211> LENGTH: 61
<212> TYPE: PRT
<213> ORGANISM: Homo sapiens

<400> SEQUENCE: 69

Val Asn Leu Phe Ala Gly Lys Phe Gly Arg Cys Ile Asn Gln Thr Glu
1               5                   10                  15

Gly Asp Leu Pro Leu Asn Tyr Thr Ile Val Asn Asn Lys Ser Gln Cys
                20                  25                  30

Glu Ser Leu Asn Leu Thr Gly Glu Leu Tyr Trp Thr Lys Val Lys Val
            35                  40                  45

Asn Phe Asp Asn Val Gly Ala Gly Tyr Leu Ala Leu Leu
        50                  55                  60

<210> SEQ ID NO 70
<211> LENGTH: 61
<212> TYPE: PRT
<213> ORGANISM: Rattus norvegicus

<400> SEQUENCE: 70

Val Asn Leu Phe Ala Gly Lys Phe Gly Arg Cys Ile Asn Gln Thr Glu
1               5                   10                  15

Gly Asp Leu Pro Leu Asn Tyr Thr Ile Val Asn Asn Lys Ser Glu Cys
                20                  25                  30

Glu Ser Phe Asn Val Thr Gly Glu Leu Tyr Trp Thr Lys Val Lys Val
            35                  40                  45

Asn Phe Asp Asn Val Gly Ala Gly Tyr Leu Ala Leu Leu
        50                  55                  60

<210> SEQ ID NO 71
<211> LENGTH: 57
<212> TYPE: PRT
<213> ORGANISM: Rattus norvegicus

<400> SEQUENCE: 71

Val Asn Leu Phe Ser Gly Lys Phe Gly Arg Cys Ile Asn Gly Thr Asp
1               5                   10                  15

Ile Asn Met Tyr Leu Asp Phe Thr Glu Val Pro Asn Arg Ser Gln Cys
                20                  25                  30

Asn Ile Ser Asn Tyr Ser Trp Lys Val Pro Gln Val Asn Phe Asp Asn
            35                  40                  45

Val Gly Asn Ala Tyr Leu Ala Leu Leu
        50                  55

The invention claimed is:

1. A method of evaluating a condition of a human patient with respect to prostate cancer comprising:
   (a) obtaining a sample containing nucleic acid and/or protein from the patient; and
   (b) determining the expression level of hNe—Na voltage-gated $Na^+$ channel nucleic acid or protein in said sample;
   wherein said evaluation is diagnosing prostate cancer in a human patient, wherein overexpression of the hNe—Na voltage-gated $Na^+$ channel nucleic acid or protein is detected.

2. A method according to claim 1 wherein said evaluation is diagnosing metastatic cancer in a human patient.

3. A method according to claim 1 wherein the sample contains nucleic acid and the level of hNe—Na voltage-gated $Na^+$ channel nucleic acid is measured by contacting the said nucleic acid with a nucleic acid which hybridises selectively to hNe—Na voltage-gated $Na^+$ channel nucleic acid.

4. A method according to claim 3 wherein the sample contains a mRNA and the nucleic acid as said selectively hybridises to hNe—Na voltage-gated $Na^+$ channel mRNA.

5. A method according to claim 3 wherein the nucleic acid which hybridises as said is selected from the group consisting of those that are single stranded, are suitable for use in the nucleic acid amplification reaction, or a combination thereof and is detectably labeled.

6. A method according to claim 4 wherein the nucleic acid which hybridises as said is selected from the group consisting of those that are single stranded, are suitable for use in a nucleic acid amplification reaction, or a combination thereof and is detectably labeled.

7. A method according to claim 1 wherein the sample contains protein and the level of hNe—Na voltage-gated $Na^+$ channel protein is measured.

8. A method according to claim 7 wherein the level of said protein is measured by contacting the protein with a molecule which selectively binds to hNe—Na voltage-gated $Na^+$ channel protein.

9. A method according to claim 7 wherein the selective binding molecule is selected from the group consisting of an antibody or an antibody fragment thereof.

10. A method according to claim 7 wherein the selective binding molecule comprises a detectable label.

11. A method according to claim 8 wherein the selective binding molecule comprises a detectable label.

12. A method according to claim 1 wherein the sample is a sample of prostate tissue selected from tissue in which cancer is suspected or in which cancer may be or has been found, or contains cells from said tissue.

13. A method according to claim 12 wherein the sample is selected from the group consisting of urine, semen, blood or lymphatic circulation.

* * * * *